United States Patent
Frenette et al.

(10) Patent No.: US 9,757,451 B2
(45) Date of Patent: Sep. 12, 2017

(54) USE OF RANK/RANKL ANTAGONISTS FOR TREATING MUSCULAR DYSTROPHY

(71) Applicant: UNIVERSITÉ LAVAL, Québec (CA)

(72) Inventors: Jérôme Frenette, Québec (CA); Josef Penninger, Vienna (AT)

(73) Assignee: UNIVERSITÉ LAVAL, Québec (CA)

( * ) Notice: Subject to any disclaimer, the term of this patent is extended or adjusted under 35 U.S.C. 154(b) by 174 days.

(21) Appl. No.: 14/356,579

(22) PCT Filed: Nov. 6, 2012

(86) PCT No.: PCT/CA2012/050788
§ 371 (c)(1),
(2) Date: May 6, 2014

(87) PCT Pub. No.: WO2013/067639
PCT Pub. Date: May 16, 2013

(65) Prior Publication Data
US 2014/0302023 A1    Oct. 9, 2014

Related U.S. Application Data

(60) Provisional application No. 61/556,508, filed on Nov. 7, 2011.

(51) Int. Cl.
*A61K 39/395* (2006.01)
*A61K 31/00* (2006.01)
(Continued)

(52) U.S. Cl.
CPC ........ *A61K 39/3955* (2013.01); *A61K 31/137* (2013.01); *A61K 31/167* (2013.01);
(Continued)

(58) Field of Classification Search
None
See application file for complete search history.

(56) References Cited

U.S. PATENT DOCUMENTS

| 7,700,574 B2 | 4/2010 | Baker et al. |
| 7,744,886 B2 | 6/2010 | Anderson |

(Continued)

FOREIGN PATENT DOCUMENTS

| WO | WO 00/01817 A2 | 1/2000 |
| WO | WO 02/092016 A2 | 11/2002 |

(Continued)

OTHER PUBLICATIONS

Wust et al., Factors contributing to muscle wasting and dysfunction in COPD patients, Int'l. J. COPD, 2(3):289-300, 2007.*

(Continued)

*Primary Examiner* — Claire Kaufman
(74) *Attorney, Agent, or Firm* — Knobbe, Martens, Olson & Bear, LLP

(57) ABSTRACT

The present invention relates to uses and methods comprising one or more RANK/RANKL antagonists or of a pharmaceutical composition comprising one or more RANK/RANKL antagonists and a pharmaceutically acceptable carrier for treating neuromuscular disorders, non-genetic myopathies, or genetic myopathies; maintaining and/or preserving the excitation:contraction:relaxation coupling; reducing loss of muscle strength associated with neuromuscular disorders, non-genetic myopathies or genetic myopathies; reducing the loss of muscular strength associated with skeletal or cardiac muscle disuse, diseases and aging; or regulating skeletal or cardiac muscle disuse, diseases and/or aging in a patient in need thereof. The present invention also relates to combinations and compositions comprising one or more RANK/RANKL antagonists and to methods for identifying candidate compounds.

20 Claims, 26 Drawing Sheets

(51) Int. Cl.
| | |
|---|---|
| *A61K 38/17* | (2006.01) |
| *A61K 31/7105* | (2006.01) |
| *G01N 33/68* | (2006.01) |
| *A61K 45/06* | (2006.01) |
| *C12N 15/113* | (2010.01) |
| *A61K 38/27* | (2006.01) |
| *A61K 38/30* | (2006.01) |
| *A61K 31/568* | (2006.01) |
| *A61K 31/137* | (2006.01) |
| *A61K 31/167* | (2006.01) |
| *A61K 31/401* | (2006.01) |
| *A61K 31/403* | (2006.01) |
| *A61K 31/405* | (2006.01) |
| *A61K 31/417* | (2006.01) |
| *A61K 31/472* | (2006.01) |
| *A61K 31/55* | (2006.01) |
| *A61K 31/573* | (2006.01) |
| *A61K 31/675* | (2006.01) |

(52) U.S. Cl.
CPC .......... *A61K 31/401* (2013.01); *A61K 31/403* (2013.01); *A61K 31/405* (2013.01); *A61K 31/417* (2013.01); *A61K 31/472* (2013.01); *A61K 31/55* (2013.01); *A61K 31/568* (2013.01); *A61K 31/573* (2013.01); *A61K 31/675* (2013.01); *A61K 31/7105* (2013.01); *A61K 38/1793* (2013.01); *A61K 38/27* (2013.01); *A61K 38/30* (2013.01); *A61K 45/06* (2013.01); *C12N 15/1136* (2013.01); *G01N 33/6863* (2013.01); *G01N 2333/7151* (2013.01); *G01N 2800/2878* (2013.01)

(56) References Cited

U.S. PATENT DOCUMENTS

| | | |
|---|---|---|
| 2002/0086312 A1 | 7/2002 | Dougall |
| 2003/0021785 A1 | 1/2003 | Dougall |
| 2005/0031583 A1 | 2/2005 | Grewal |
| 2008/0200389 A1 | 8/2008 | Bird et al. |

FOREIGN PATENT DOCUMENTS

| | | |
|---|---|---|
| WO | WO 03/080671 A1 | 10/2003 |
| WO | WO 2005/028633 A2 | 3/2005 |
| WO | WO 2005/121316 A1 | 12/2005 |
| WO | WO 2007/059136 A2 | 5/2007 |

OTHER PUBLICATIONS

Schwarz et al., Review: Clinical development of anti-RANKL therapy, Arth. Res. Ther. 9(Suppl. 1):57, 2007.*

Panizo et al., RANKL increases vascular smooth muscle cell calcification through a RANK-BMP4-dependent pathway, Circ. Res. 104:1041-1048, 2009.*

G. Lutz and D. Stevenson, The Writer's Digest Grammar Desk Reference, Ed. K. Nickell, Writer's Digest Books: Ohio, pp. 102-103, 2005.*

Gallagher, J.C. 2008 "Advances in bone biology and new treatments for bone loss" *Maturitas* 60; 65-69.

Resch, H. 2010 "Osteoporosis: New-generation Drugs" *Breast Care* 5; 313-319.

Lefkowitz, et al. 2012 "Treatment of facioscapulohumeral muscular dystrophy with Denosumab" *American Journal of Case Reports* 13: 66-68.

Miller 2009 "Denosumab: Anti-RANKL antibody" *Current Osteoporosis Reports* 7(7): 18-22.

Supplementary European Search Report in corresponding European Application No. EP 12847546, dated Mar. 23, 2015.

Anderson, D.M. et al. 1997 "A homologue of the TNF receptor and its ligand enhance T-cell growth and dendritic-cell function" *Nature* 390: 175-179.

DuFresne, S. et al. 2015 "Ostoprotegerin protects against muscular dystrophy" *Am J Pathol* 185: 920-926.

Genbank Accession No. AAB86811, Nov. 21, 1997.

* cited by examiner

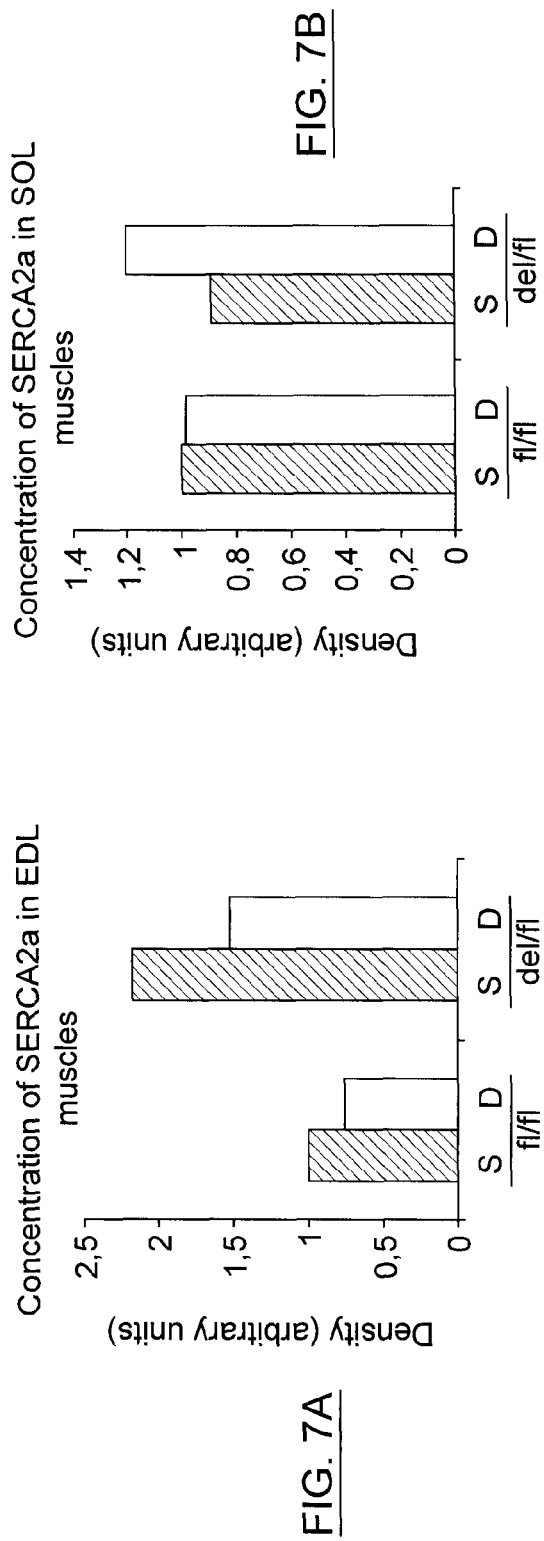
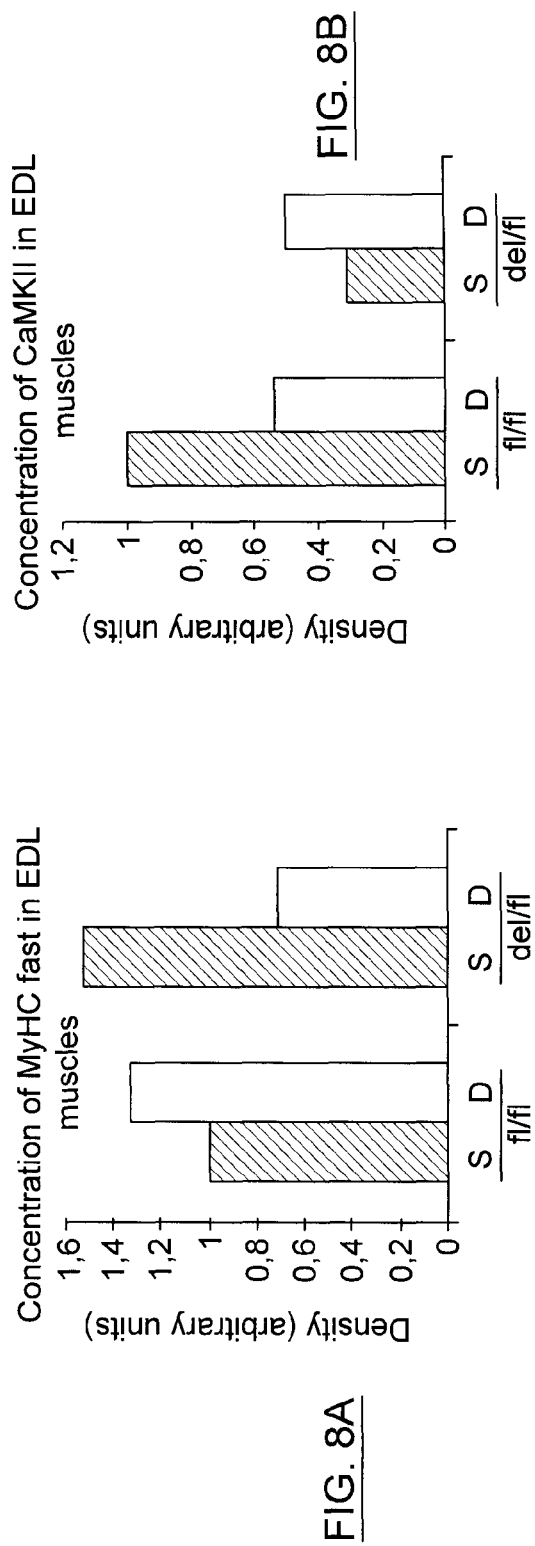
FIG. 7A
FIG. 7B
FIG. 8A
FIG. 8B

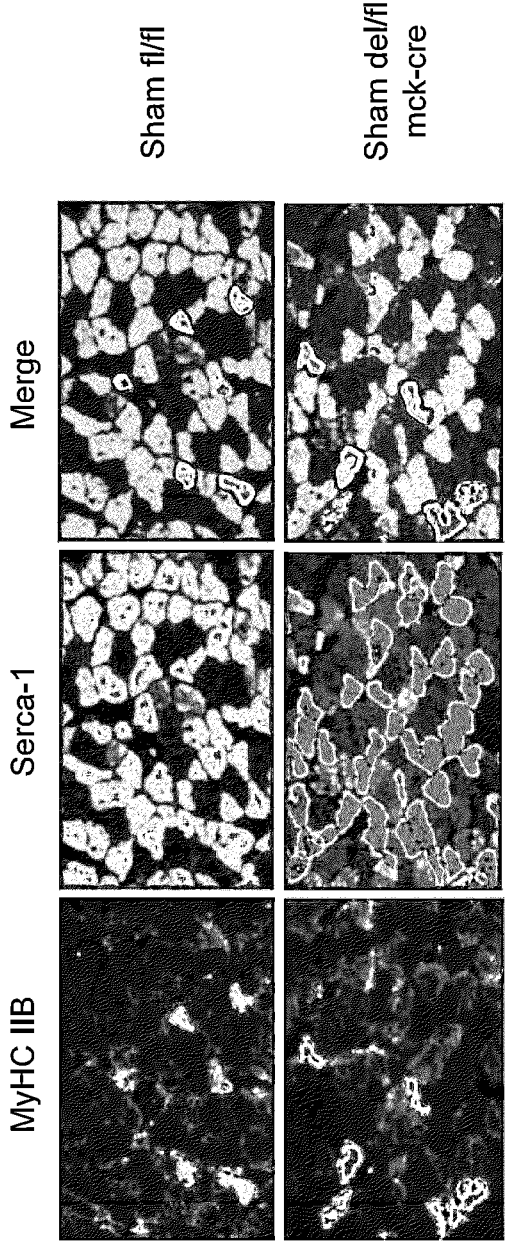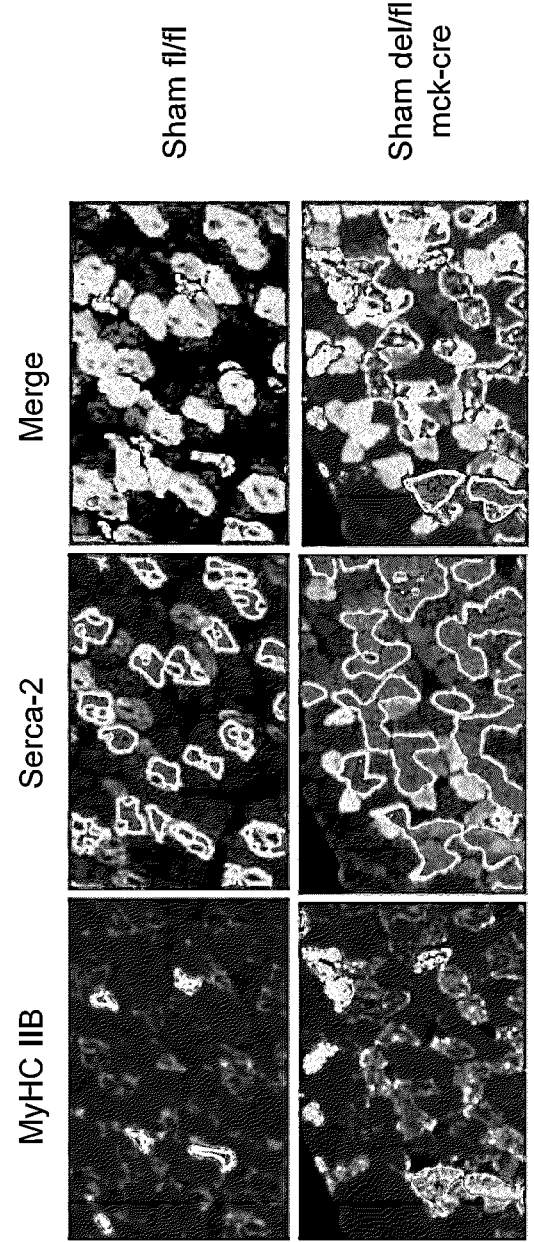

SEQUENCE LISTING

```
<160> NUMBER OF SEQ ID NOS: 1

<210> SEQ ID NO 1
<211> LENGTH: 317
<212> TYPE: PRT
<213> ORGANISM: Homo sapiens

<400> SEQUENCE: 1

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Tyr Tyr Leu Tyr Ala Asn Ile Cys Phe Arg His
        210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255
```

-continued

```
Lys Gly Gly Ser Thr Lys Tyr Trp Ser Gly Asn Ser Glu Phe His Phe
            260                 265                 270
Tyr Ser Ile Asn Val Gly Gly Phe Phe Lys Leu Arg Ser Gly Glu Glu
            275                 280                 285
Ile Ser Ile Glu Val Ser Asn Pro Ser Leu Leu Asp Pro Asp Gln Asp
    290                 295                 300
Ala Thr Tyr Phe Gly Ala Phe Lys Val Arg Asp Ile Asp
305                 310                 315
```

USE OF RANK/RANKL ANTAGONISTS FOR TREATING MUSCULAR DYSTROPHY

REFERENCE TO RELATED APPLICATIONS

This application is U.S. National Phase of International Application PCT/CA2012/050788, filed Nov. 6, 2012 designating the U.S., and published in English as WO 2013/067639 A1 on May 16, 2013, which claims priority to U.S. 61/556,508 filed Nov. 7, 2011 which is herein incorporated by reference.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 24621259_1.TXT, the date of creation of the ASCII text file is Nov. 11, 2016, and the size of the ASCII text file is 3.24 KB.

BACKGROUND

Bones and skeletal muscles make up approximately 20 and 45%, respectively, of the weight of the human body. They have several vital functions. For example, locomotion, breathing, postural support, physical protection, blood glucose disposal, thermogenesis, $Ca^{2+}$ homeostasis, production of blood cells, and energy storage are all under the control of bones and skeletal muscles. Musculoskeletal diseases are a major burden on individuals and the health and social care systems, with major indirect costs[1]. The prevalence of many musculoskeletal problems increases markedly with age, obesity, and lack of physical activity[1]. These three risk factors are expected to increase steadily over the next decade, putting people at increasingly higher risk for musculoskeletal diseases. The United States Health Examination Survey indicated that 30% of the population aged between 25-74 had musculoskeletal symptoms[2]. More importantly, in Canada, the estimated number of people with disabling musculoskeletal disorders is more than twice that for all cancers combined[3]. Clinical studies have shown the worsening of osteoporosis and muscle atrophy/dysfunction occurs in parallel[4].

Skeletal muscles and bones remain plastic, work in synchrony, and have the ability to adjust their structures in response to their mechanical, hormonal, and metabolic environments[5]. This is best exemplified by professional tennis players, whose dominant arm has stronger muscles and greater bone mass. Skeletal muscle and bone atrophy (loss of muscle and bone mass) occur with aging, prolonged bed rest, strokes, spinal cord injuries, burns, neurodegenerative diseases, space flight, immobilization, arthritis, osteoarthritis, denervation, and a number of other debilitating conditions[6,7,8,9,10,11,12,13,14,15,16]. In addition, long-term glucocorticoid administration (e.g., dexamethasone), which is an anti-inflammatory and immunosuppressant, induces osteoporosis and muscle atrophy/dysfunction[17], while local and systemic alterations in hormone and pro-inflammatory cytokine levels stimulate muscle and bone atrophy[18,19]. Changes in intracellular $Ca^{2+}$ concentrations also regulate the physiological activities and expression of specific bone and muscle genes[20,21]. Physical exercise and mechanical stimuli, on the other hand, promote increased bone density and skeletal muscle hypertrophy[22,23].

Osteoblasts in bone produce the extracellular matrix, cytokines, and growth factors. They are also involved in the regulation of bone formation and resorption in response to hormonal and local factors. Like macrophages, osteoclasts originate from myeloid cells and play key roles in bone degradation and remodelling. One advance in bone biology and disease was the discovery of the receptor-activator of nuclear factor κβ (RANK), receptor-activator of nuclear factor κβ ligand (RANKL), and osteoprotegerin (OPG) triad (RANK/RANKL/OPG). RANK/RANKL triggers a network of TRAF-mediated kinase cascades that promote osteoclast differentiation. RANKL is expressed on osteoblast cells and its receptor, Rank, on pre-osteoclastic cells. RankL production is stimulated by IL-1, IL-6, IL-11, IL-17, TNF-α, vitamin D, $Ca^{2+}$, parathyroid, glucocorticoids, prostaglandin E2, and immunosuppressive drugs, and is down-regulated by TGF-$\alpha$[24]. The RANK/RANKL interaction induces the differentiation and formation of multinucleated mature osteoclasts, causing bone resorption. The third protagonist, OPG, is also produced by osteoblasts and exerts an inhibitory effect on the pre-osteoclastic differentiation process. OPG, by binding to RankL, inhibits the RANK/RANKL interaction and subsequent osteoclastogenesis. OPG is thus a very efficient anti-resorptive agent. It also serves as a decoy receptor for the tumour necrosis factor-related apoptosis-inducing ligand (TRAIL) and increases cell survival by blocking the apoptotic effects of this ligand. The fact that the overexpression of OPG in mice results in severe osteoporosis and that OPG-null mice are osteoporotic is testimony to the physiological importance of OPG[25,26,27]. The lack of RANK or RANKL induces osteoporosis in mice[28,29].

Muscle wasting/dysfunction is a hallmark of diverse catabolic conditions, including muscle disuse, burn injuries, cancers, renal failure, AIDS, chronic obstructive pulmonary disease, and aging[31,32,33,34]. While calpain and the inhibition of the autophagy/lysosome system can induce muscle protein degradation, the ubiquitin/proteasome pathway appears to be the most important system involved in muscle proteolysis[35]. For example, the ubiquitin ligase muscle atrophy F-box (MAFbx or atrogin-1) and muscle ring finger 1 (MuRF1), which target muscle-specific proteins for degradation by the proteasome, are up-regulated and are two of the genes most affected by various types of muscle atrophy[36,37]. Conversely, hypertrophy is in part mediated by IGF-1 via the stimulation of the phosphatidylinositol-3-kinase (PI3K)/Akt pathway[38]. In transgenic mice, the overexpression of IGF-1 or the active form of Akt is sufficient to induce skeletal muscle hypertrophy[39,40]. Akt downstream targeting of glycogen synthase kinase (GSK)-3beta, the mammalian target of rapamycin (mTOR), p70 ribosomal protein S6 kinase (p70S6K), and the phosphorylation of forkhead family transcription factor Forkhead box 0 (FOXO) prevent the transcription and activation of MAFbx and MuRF1[41,42].

Bone resorption is regulated through the expression of OPG and RANKL by osteoblastic cells and is altered by various osteotropic factors, such as vitamin D, that regulate $Ca^{2+}$ influx. Vitamin D changes the functional properties of L-type voltage sensitive $Ca^{2+}$ channels (L-type VSCC) and alters the expression and activity of protein kinases[43,44,45]. L-type VSCC is the primary site for $Ca^{2+}$ influx into proliferating osteoblasts[48]. Once $Ca^{2+}$ accumulates intracellularly, calmodulin (CaM), a major intracellular $Ca^{2+}$ receptor, can interact with and regulate various proteins, including $Ca^{2+}$ channels, $Ca^{2+}$/calmodulin-dependent protein kinase (CaMK), and calcineurin, all of which can control transcriptional expression[46]. The transient elevation of intracellular $Ca^{2+}$ directly or indirectly influences the expression and activity of intracellular protein kinases, including c-AMP dependent protein kinase A (PKA), CaMK, and MAPK[45,47], which can potentially phosphorylate L-type VSCC and alter channel function. More importantly, there is a clear feedback loop between OPG and RANKL that serves as a major regulatory mechanism for controlling osteoclastogenesis and L-type VSCC, thus modulating $Ca^{2+}$ influx into osteoblasts. This is best exemplified by the fact that OPG secretion by osteoblasts is regulated through CaMK signalling, which depends on the activity of L-type VSCC[48]. L-type VSCC is so important that blocking its function inhibits osteogenesis, produces vertebral defects, and decreases mineral apposition[49].

In skeletal muscle, the sequence of events that converts an electrical stimulus (alpha motor neurons and action potential) to a mechanical response (muscle contraction) is defined as excitation:contraction coupling (ECC). This essential sequence of events in muscle physiology involves the depolarization of the transverse-tubular (t) system, which activates dihydropyridine receptors (DHPRs), also called L-type voltage dependent $Ca^{2+}$ channels, an analogous to L-type VSCC. The activation of DHPRs opens ryanodine receptor/$Ca^{2+}$ release channels (RYR1) adjacent to the sarcoplasmic reticulum (SR) membrane, resulting in the rapid efflux of large of amounts of $Ca^{2+}$ into the cytoplasm and the binding of $Ca^{2+}$ to troponin C and then actin and myosin to form cross bridges, shortening the sarcomere and decreasing force development[50]. To avoid permanent muscle contraction, $Ca^{2+}$ is pumped back into the sarcoplasmic reticulum by sarcoplasmic endoplasmic reticulum $Ca^{2+}$ ATPase (SERCA). Calsequestrin can then bind free $Ca^{2+}$ in the SR so that SERCA does not have to pump against a high concentration gradient. It is important to mention that the $Ca^{2+}$ concentration is 10,000 times higher in the SR than in intracellular compartment under basal and resting conditions. The release of $Ca^{2+}$ by RYR1 and the reuptake of $Ca^{2+}$ by SERCA are also tightly regulated by several binding proteins. Calstabin1, PKA, and protein phosphatase 1 (PP1) control the open and closed state of the RYR1 channel. PKA mediates the phosphorylation of RYR1 at Ser2844, increases the sensitivity of the channel to cytoplasmic $Ca^{2+}$, reduces the binding affinity of calstabin1 for the RyR1 complex, and destabilizes the closed state of the channel, leading to $Ca^{2+}$ leakage[51,52]. The rate at which SERCA moves $Ca^{2+}$ across the SR membrane can be controlled by phospholamban under β-adrenergic stimulation. For instance, the movement of $Ca^{2+}$ is reduced when phospholamban is associated with SERCA while the dissociation of phospholamban increases SERCA activity and $Ca^{2+}$ movement. From a physiological point of view, SERCA works at sub-maximal levels in resting cardiac and skeletal muscles, which allows intense physical performance (increased muscle force and speed) as needed when phospholamban is phosphorylated and dissociated from SERCA. This phenomenon is tightly linked to the well-known fight or flight response, which is under the control of the sympathetic nervous system (catecholamine hormones; adrenaline and noradrenaline). Under pathological and chronic stress conditions, constant $Ca^{2+}$ leakage and dysfunctional $Ca^{2+}$ mobilization impair muscle force development and may activate $Ca^{2+}$-dependent proteases, including calpain, leading to a detrimental effect on cell viability.

Skeletal muscles are primarily composed of four muscle fibre types: type I fibres (slow and oxidative), type IIa fibres (fast and oxidative), and type IIb fibres (fast and glycolytic). Type I fibres play an important role in maintaining body posture, while type IIb and IIx fibres are responsive during physical activity. Type IIa fibres are a hybrid between type I and type IIb fibres and can perform short or prolonged exercises. Specific muscle diseases, mechanical stress, and drug treatments affect all four muscle fibre phenotypes to different degrees. For example, a decrease in mechanical load and neuromuscular activity favours muscle atrophy and a conversion of muscle fibre phenotypes from slow to fast[53]. Functional overloads cause a gain in muscle mass while prolonged exercises lead to the transformation of pre-existing fast-twitch muscle fibres to a slow-twitch oxidative phenotype[54]. Additionally, sarcopenia (progressive loss of skeletal muscle mass and strength during aging) affects oxidative and glycolytic muscle fibres differently. For example, type II muscle fibres begin to atrophy in humans during the fifth decade while type I muscle fibres maintain their size for most of a human's lifetime. Prolonged glucocorticoid treatments mainly affect fast twitch muscle fibres, leaving slow twitch muscle fibres intact. Type IIb fibres are converted to oxidative phenotype fibres (type I or IIa) or disappear first through a necrotic process in mdx mice and DMD patients. The accumulated evidence indicates that type IIb fibres, which are essential for brief and powerful contractions (i.e., standing up from a chair), are the most vulnerable muscle fibres in several types of myopathy.

Proinflammatory cytokines TNF-α and IL-1 activate transcription factor NF-kB, which can abrogate muscle proliferation, differentiation, and growth in several chronic and inflammatory diseases. While there is strong evidence that NF-kB regulates muscle mass, other transcription factors also play an important role in the regulation of muscle mass. In cancer cachexia, myostatin-induced muscle atrophy is regulated through FOXO-1 and the E3 ubiquitin ligase gene MAFBx/atrogin-1, a process that is independent of the NF-kB/MuRF1 mechanism[55]. Furthermore, sepsis results in a sustained increase in the expression and activity of AP-1 and C/EBP[56,57], which are, in part, regulated by glucocorticoids[58]. Other observations indicate that $Ca^{2+}$ concentrations and the expression of muscle m-, μ-calpain are important in muscle atrophy and dysfunction in septic muscle[59]. Furthermore, treating septic rats with dantrolene, a substance that inhibits the release of $Ca^{2+}$ from intracellular stores, prevents the sepsis-induced release of myofilaments[59]. $Ca^{2+}$ also regulates phosphorylation and dephosphorylation by activating CaMK and calcineurin[60], leading to an increase in proteasome activity[61]. Muscle atrophy/dysfunction is thus clearly under the control of several signalling pathways.

There is a need for new therapy for treating neuromuscular disorders, non-genetic myopathies, genetic myopathies and/or for regulating skeletal or cardiac muscle disuse, diseases and aging.

SUMMARY OF THE INVENTION

In one aspect, there is provided the use of one or more RANK/RANKL antagonists or of a pharmaceutical composition comprising one or more RANK/RANKL antagonists and a pharmaceutically acceptable carrier for:
  treating neuromuscular disorders, non-genetic myopathies, or genetic myopathies;
  maintaining and/or preserving the excitation:contraction:relaxation coupling;
  reducing loss of muscle strength associated with neuromuscular disorders, non-genetic myopathies or genetic myopathies;
  reducing the loss of muscular strength associated with skeletal or cardiac muscle disuse, diseases and aging; or regulating skeletal or cardiac muscle disuse, diseases and/or aging;
in a patient in need thereof.

In one aspect there is provided a method for:
- treating neuromuscular disorders, non-genetic myopathies, or genetic myopathies;
- maintaining and/or preserving the excitation:contraction:relaxation coupling;
- reducing loss of muscle strength associated with neuromuscular disorders, non-genetic myopathies or genetic myopathies;
- reducing the loss of muscular strength associated with skeletal or cardiac muscle disuse, diseases and aging; or
- regulating skeletal or cardiac muscle disuse, diseases and/or aging;

comprising administering of one or more RANK/RANKL antagonists or of a pharmaceutical composition comprising one or more RANK/RANKL antagonists and a pharmaceutically acceptable carrier to a patient in need thereof.

In one aspect there is provided pharmaceutical combinations for:
- treating neuromuscular disorders, non-genetic myopathies, or genetic myopathies;
- maintaining and/or preserving the excitation:contraction:relaxation coupling;
- reducing loss of muscle strength associated with neuromuscular disorders, non-genetic myopathies or genetic myopathies;
- reducing the loss of muscular strength associated with skeletal or cardiac muscle disuse, diseases and aging; or
- regulating skeletal or cardiac muscle disuse, diseases and/or aging;
- said combination comprising one or more RANK/RANKL antagonists and a further therapeutic agent active against neuromuscular disorders and genetic myopathies.

In one aspect there is provided pharmaceutical composition for:
- treating neuromuscular disorders, non-genetic myopathies, or genetic myopathies;
- maintaining and/or preserving the excitation:contraction:relaxation coupling;
- reducing loss of muscle strength associated with neuromuscular disorders, non-genetic myopathies or genetic myopathies;
- reducing the loss of muscular strength associated with skeletal or cardiac muscle disuse, diseases and aging; or
- regulating skeletal or cardiac muscle disuse, diseases and/or aging;
- said composition comprising one or more RANK/RANKL antagonists and a pharmaceutically acceptable carrier.

In one aspect, there is provided the use or a method comprising the use or administration of one or more RANK/RANKL antagonists or of a pharmaceutical composition comprising one or more RANK/RANKL antagonists and a pharmaceutically acceptable carrier for maintaining and/or preserving the excitation:contraction:relaxation coupling for treating neuromuscular disorders, non-genetic myopathies, genetic myopathies, and/or for regulating skeletal or cardiac muscle disuse, diseases and aging in a patient in need thereof.

In one aspect the said one or more RANK/RANKL antagonists or of a pharmaceutical composition is used in combination with one or more further therapeutic agent indicated for the treatment of neuromuscular disorders and genetic myopathies.

In one aspect, there is provided a method for identifying a candidate compound useful for:
- treating neuromuscular disorders, non-genetic myopathies, or genetic myopathies;
- maintaining and/or preserving the excitation:contraction:relaxation coupling;
- reducing loss of muscle strength associated with neuromuscular disorders, non-genetic myopathies or genetic myopathies;
- reducing the loss of muscular strength associated with skeletal or cardiac muscle disuse, diseases and aging; or
- regulating skeletal or cardiac muscle disuse, diseases and/or aging;

the method comprising the steps of:
a) contacting the candidate compound with a biological system comprising a RANK polypeptide or fragment thereof or a RANKL polypeptide or fragment thereof,
b) measuring the ability of the candidate compound to bind to the RANK polypeptide or fragment thereof or to the RANKL polypeptide, and
c) determining if the candidate compound is useful for:
- treating neuromuscular disorders, non-genetic myopathies, or genetic myopathies;
- maintaining and/or preserving the excitation:contraction:relaxation coupling;
- reducing loss of muscle strength associated with neuromuscular disorders, non-genetic myopathies or genetic myopathies;
- reducing the loss of muscular strength associated with skeletal or cardiac muscle disuse, diseases and aging; or
- regulating skeletal or cardiac muscle disuse, diseases and/or aging;
based on the result of step b).

In one aspect, there is provided a method for identifying a candidate compound useful for:
- treating neuromuscular disorders, non-genetic myopathies, or genetic myopathies;
- maintaining and/or preserving the excitation:contraction:relaxation coupling;
- reducing loss of muscle strength associated with neuromuscular disorders, non-genetic myopathies or genetic myopathies;
- reducing the loss of muscular strength associated with skeletal or cardiac muscle disuse, diseases and aging; or
- regulating skeletal or cardiac muscle disuse, diseases and/or aging;

the method comprising the steps of:
a) contacting the candidate compound with a biological system comprising a RANK polypeptide or fragment thereof or a RANKL polypeptide
b) measuring the ability of the candidate compound to reduce or inhibit the interaction between the RANK polypeptide or fragment thereof or the RANKL polypeptide, and
c) determining if the candidate compound is useful for:
- treating neuromuscular disorders, non-genetic myopathies, or genetic myopathies;
- maintaining and/or preserving the excitation:contraction:relaxation coupling;
- reducing loss of muscle strength associated with neuromuscular disorders, non-genetic myopathies or genetic myopathies;

reducing the loss of muscular strength associated with skeletal or cardiac muscle disuse, diseases and aging; or regulating skeletal or cardiac muscle disuse, diseases and/or aging;

based on the result of step b).

BRIEF DESCRIPTION OF THE DRAWINGS

FIG. 7. The concentrations of SERCA2a double in EDL muscles from RANK$^{del/fl}$ mice. Sham (S) or denervated muscles (D) from EDL (A) and SOL (B) muscles were dissected and homogenized for Western blotting as described in the proposal. SERCA pumps back Ca$^{2+}$ into the SR and plays a key role in muscle relaxation and performance. The increase in SERCA concentration is particularly visible in sham and denervated EDL muscles from RANK ko mice (del/fl). The concentration of SERCA dose not increase significantly in SOL muscles, (n=1).

FIG. 8. The concentration of MyHC fast increases while CaMKII decreases in sham RANK$^{del/fl}$ mice. These results are consistent with the evidence supporting a role for the Ca$^{2+}$ calmodulin-dependent kinase (CaMK) pathway in the fast-to-slow fibre transformation. A repression of CaMKII expression would thus favours a fast-twitch phenotype. Western blots were performed as described in the proposal and fils were scanned and analysed with Quantity One software.

Figure 1:
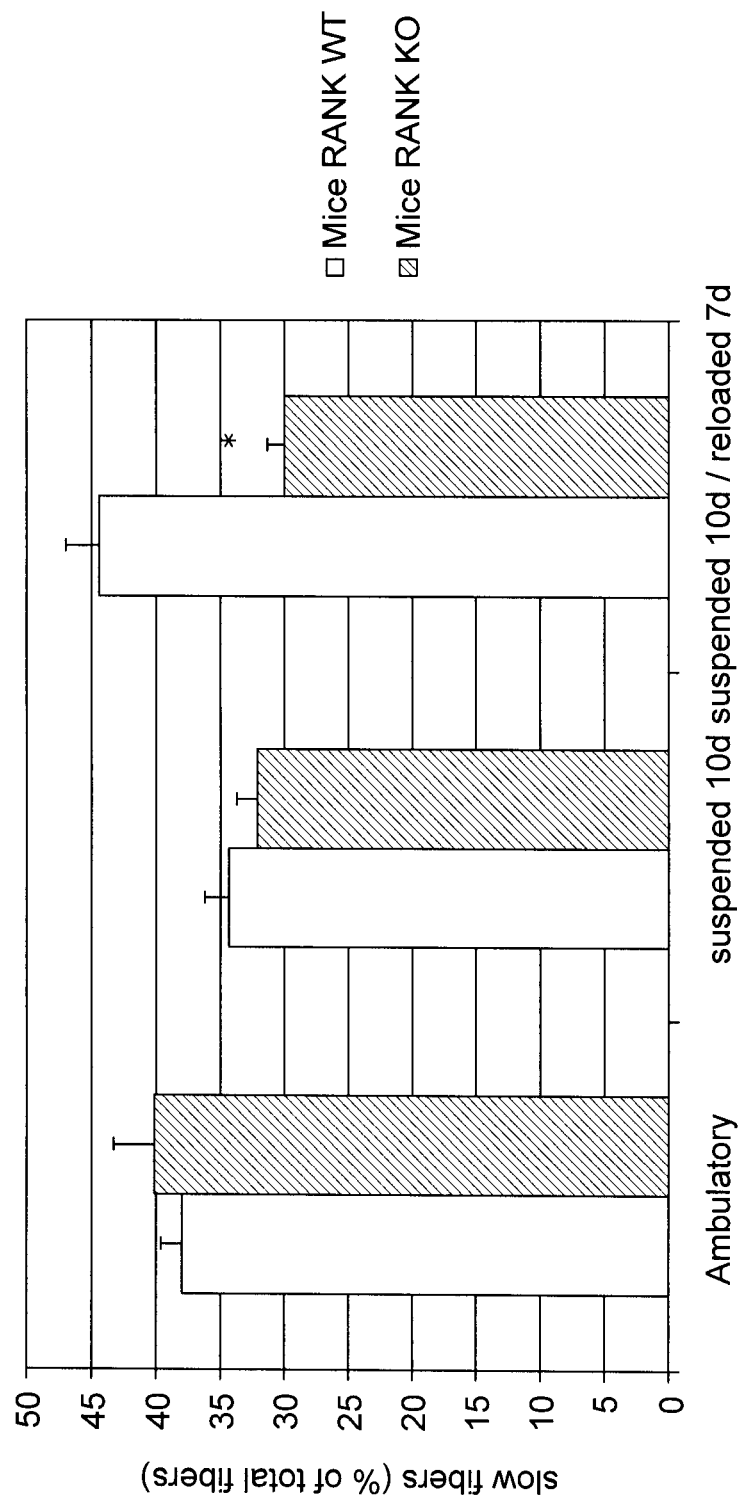
FIG. 1: RANK deletion prevents the reconversion from fast to slow myofiber phenotype in soleus muscle during the reloading period. Mice were unloaded and suspended by their tail for 10 days to induce muscle atrophy and changes from slow to fast twitch muscle fiber phenotype. The reloading period induces muscle regrowth and reconversion from fast to slow twitch muscle fiber phenotype. The absence of RANK prevents the reconversion of fast toward slow twitch fiber indicating that RANK can modulate muscle phenotype.

(A) PCR analysis of RANK floxed allele and RANK delta allele in soleus, EDL, heart, liver spleen and kidney. RANK floxed allele is deleted specifically in the SOL and EDL of RANK$^{del/fl}$ mck-cre mice (B) Western Blot of SOL and EDL muscles from RANK$^{fl/fl}$ and RANK$^{del/fl}$ mck-cre mice sham or denervated indicate that the increase in RANK protein expression observed in denervated EDL is absent in RANK$^{del/fl}$ mck-cre mice. (C) Immunohistochemistry with RANK antibody on SOL and EDL muscles from RANK$^{fl/fl}$ and RANK$^{del/fl}$ mck-cre mice sham or subjected to sciatic denervation for 14 days, 200× magnification.

FIG. 16: RANK regulates muscle function and fiber typing.

(A and B) Ex vivo contractile properties (100 Hz, 200 ms, 35V) of sham and denervated RANK$^{fl/fl}$ and RANK$^{del/fl}$ muscles revealed that the decrease in specific muscle force induced by 14 days of sciatic denervation is partially prevented by RANK depletion in EDL but not in SOL muscles (n=5-6). (C and D) Specific muscle force preservation is also observed in EDL muscles of young mdx mice (28 days) injected with OPG (0.3 mg/kg/day, i.p.) for 10 days compare to PBS. (E and F) Ex vivo muscles were stimulated with cyclic contractions (50 Hz, 200 ms stimulation every 1 s, 35V) until a reduction of 50% of initial force for EDL and 30% for SOL muscles. The shorter time to reach 50% of initial force in RANK$^{del/fl}$ denervated EDL indicate a higher fatigability compared to their wild type littermates (n=1-4). (G) Immunofluorescence staining of the different type of myosin (slow I, fast oxidative IIA, fast glycolytic IIX and IIB) on SOL of mice, ambulatory, unloaded for 10 days, or reloaded for 7 days (n=1-6). Values are expressed as a difference relative to the ambulatory RANK$^{fl/fl}$ control. * significantly different from sham RANK$^{fl/fl}$ or C57BL/10j PBS. # significantly different from RANK$^{fl/fl}$ or mdx PBS, p<0.05 (ANOVA with a post-hoc Tukey test). Data are presented as mean+/−sem.

FIG. 17: RANK/RANKL interaction influences Ca$^{2+}$ homeostasis and activates different cell signaling pathways. (A) Addition of RANKL (100 ng/ml) to C2C12 myotubes (5 days in differentiation medium) increased mean fluorescence intensity of fluo-4, an indicator of Ca$^{2+}$ concentration (n=5). (B) (Spectrofluorimetric analysis demonstrated an increase in SERCA activity in sham and denervated RANK$^{del/fl}$ compared to sham and denervated RANK$^{fl/fl}$ EDL muscles (n=1-4). (C and D) Double immunofluorescence with the MyHC isoforms (green) and SERCA isoforms (red) demonstrated that RANK$^{del/fl}$ MyHC type IIB fibers express SERCA-1 and SERCA-2 (yellow) whereas RANK$^{fl/fl}$ MyHC IIB fibers were rigourously limited to SERCA-1 in SOL muscles. (E) Graph representing the difference in the expression of SERCA isoforms for each fiber type for SOL and EDL muscles compared to sham RANK$^{fl/fl}$ mice. (F-K) Western blot images illustrating the protein expressions and phosphorylated states of PKA, IKB, p65, ERK1/2 and CaMKII expression at different time points following the addition of RANKL (100 ng/ml) into C2C12 myotubes. * significantly different from RANK$^{fl/fl}$, # significantly different from denervated RANK$^{fl/fl}$, p<0.05 (ANOVA with a post-hoc Tukey test). Data are presented as mean+/−sem.

FIG. 18: RANK depletion modifies expression of contractile, Ca$^{2+}$ regulatory, Ca$^{2+}$ signaling proteins and other cell signaling pathways. (A) Representative images of immunoblots and (B) mean fold change in contractile and regulatory protein expression in sham and denervated SOL (left) and EDL (right) muscles from RANK$^{fl/fl}$ and RANK$^{del/fl}$ mice. Data are represented as fold increase or decrease relative to sham RANK$^{fl/fl}$ muscles. Results indicate more important changes in protein expression in EDL than SOL muscles. (C) Representative images of immunoblots and (D) mean fold change in Ca$^{2+}$ Ca$^2$+ signaling protein expression in sham and denervated SOL (left) and EDL (right) muscles from RANK$^{fl/fl}$ and RANK$^{del/fl}$ mice. (E) Representative images of immunoblots and (F) mean fold change in the phosphorylation ratio of different signaling pathways in sham and denervated SOL (left) and EDL (right) muscles from RANK$^{fl/fl}$ and RANK$^{del/fl}$ mice. Results indicate an activation of the NF-kB pathway following the denervation (G) Representative images of immunoblots and (H) mean fold change in regulatory protein expression in sham and denervated SOL (left) and EDL (right) muscles from RANK$^{fl/fl}$ and RANK$^{del/fl}$ mice. The present findings showed a decrease in Ca$^{2+}$ channel proteins that control the rise in [Ca$^{2+}$]$_i$ (RyR, DHPR) and an increase in Ca$^{2+}$ proteins that favour Ca$^{2+}$ reuptake (SERCA-2, p-PLB) in RANK$^{del/fl}$ EDL muscles. One interesting finding is the phosphorylation of p-PLB on serine16. This phosphorylation of serine 16 by PKA is known to disinhibit and to improve SERCA function (I) Graphic representing the mean fold change in Ca$^{2+}$ protein ratios in sham and denervated SOL (left) and EDL (right) muscles from RANK$^{fl/fl}$ and RANK$^{del/fl}$ mice. Lastly, our results demonstrated an increase in protein ratios that favours Ca$^{2+}$ captation (SERCA-2/PLB, p-PLB/PLB, Serca-2/DHPR, SERCA-2/RyR) and a switch from SERCA-1 to SERCA-2 isoform in RANK$^{del/fl}$ EDL muscles. Data are presented as mean+/−sem * significantly different from sham RANK$^{fl/fl}$, # significantly different from denervated RANK$^{fl/fl}$, p<0.05 (ANOVA with a post-hoc Tukey test).

Figure 19A:
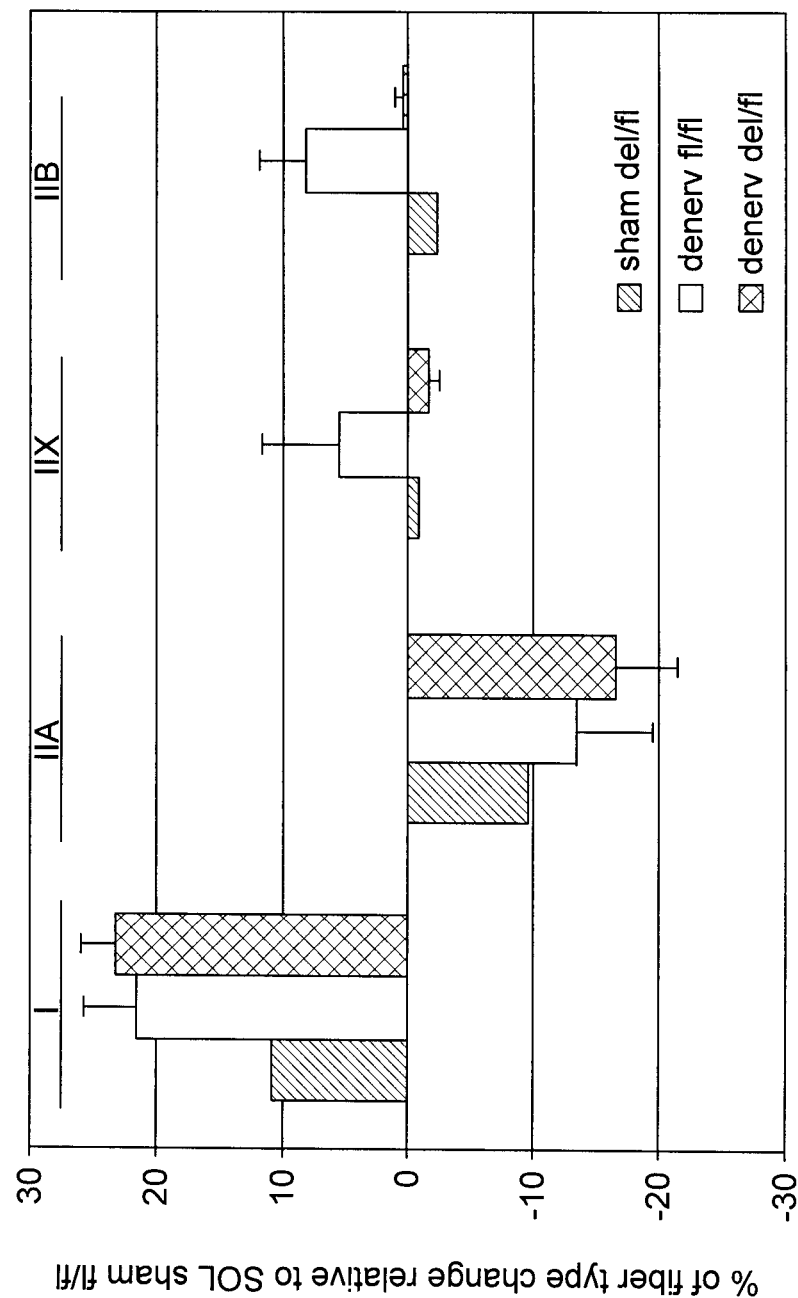
Figure 19B:
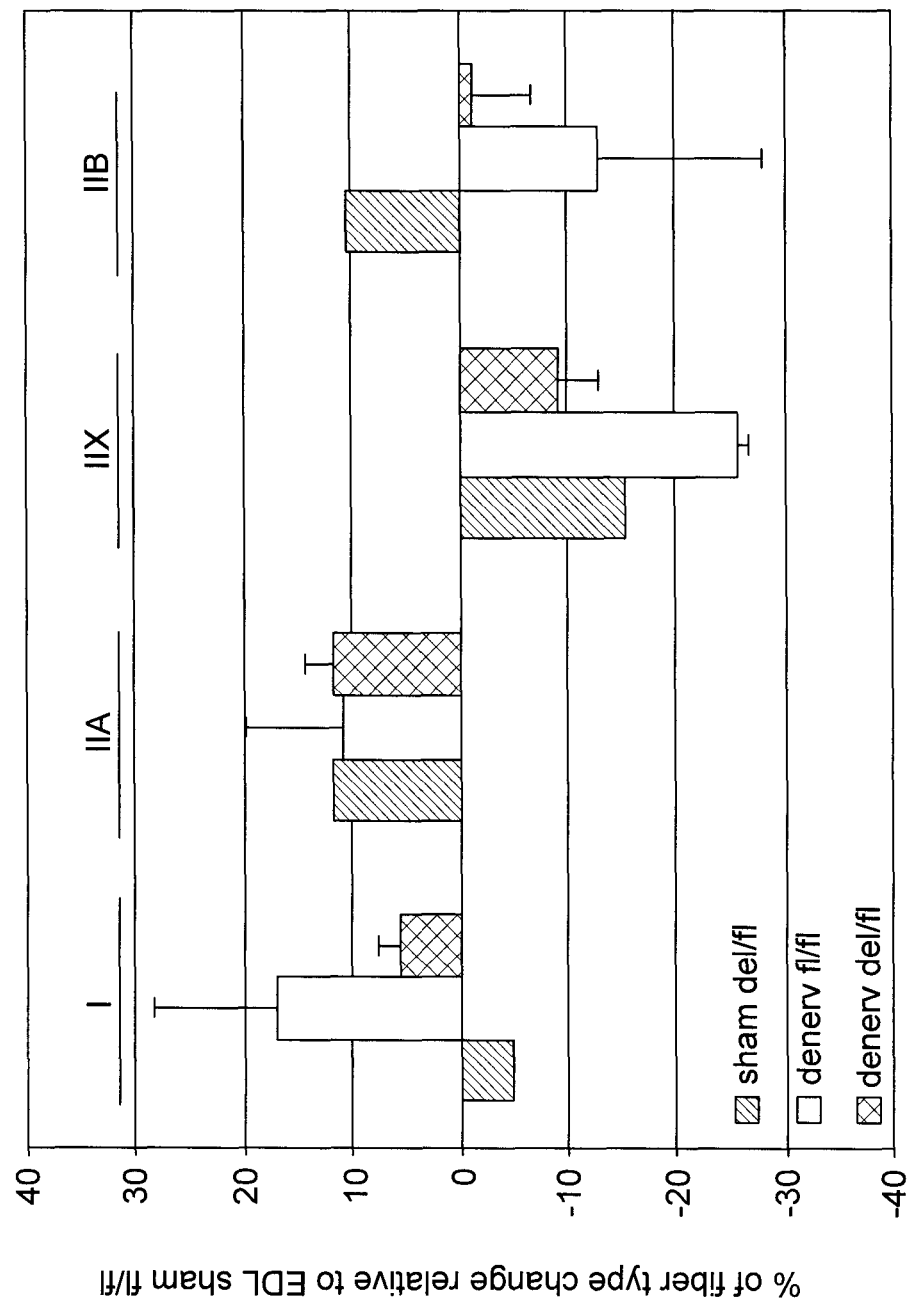

FIG. 19: The effect of RANK depletion on fiber type modification following denervation. (A and B) Immunohistochemical analysis for the different MyHC isoforms (I, IIA, IIX, IIB) were measured in sham and denervated SOL and EDL muscles from RANK$^{fl/fl}$ and RANK$^{del/fl}$ mice. (n=4-6). Data are presented as mean+/−sem. * significantly different from sham RANK$^{fl/fl}$, p<0.05 (ANOVA with a post-hoc Tukey test).

DETAILED DESCRIPTION

Without being bound to any specific theory, the present inventor(s) believe that the RANK/RANKL/OPG pathway impairs muscle function and that RANK depletion preserves excitation:contraction:relaxation coupling and improves Ca$^{2+}$ mobilization, particularly in the fast twitch muscle phenotype.

Based on the following six models: (1) the well-established model of hindlimb unloading and reloading, (2) the model of sciatic denervation (3) the model of dexamethasone induced muscle atrophy (4) the model of critical illness myopathy (5) the model of dystrophic mice (mdx) and (6) an in vitro model of myotube atrophy with dexamethasone, the present inventor(s) have found that, the reconversion from fast to slow twitch fibers is impaired following unloading and reloading in Rank ko mice whereas the lack of Rank in skeletal muscles preserves the contraction and relaxation processes, increases SERCA expression and activity, and dramatically improves muscle force in all models used. Muscle force improvement in mice specifically deficient in Rank is particularly significant in EDL muscles that are mainly composed of fast twitch fibres.

The present inventor(s) have assessed muscle force, contraction and relaxation functions, and muscle atrophy/dysfunction using various approaches, including denervation, in RANK knock-out ("ko") and wild-type mice. The present inventor(s) have studied the involvement of the RANK/RANKL/OPG pathway in muscle cell atrophy induced by dexamethasone in vitro and in vivo. The present inventor(s) have studied how the modulation of the RANK/RANKL/OPG pathway influences muscle integrity and function in a mouse model of critical illness myopathy. The present inventor(s) have also assessed the impact of daily OPG injection on muscle force in myopathic and dystrophic mdx mice.

The present inventor(s) have also found that: OPG protects against while RANKL exacerbates DEX-induced myotube atrophy. In addition the present inventor(s) have found that specific-muscle Rank deletion and OPG preserve muscle mass or function in the presence of dexamethasone or denervation or muscle dystrophy (mdx mouse). The present inventor(s) have found that the modulation of the RANK/RANKL/OPG pathway influences muscle integrity and function in a mouse model of critical illness myopathy.

In one aspect, the present invention relates to the use of one or more RANK/RANKL antagonists for treating neuromuscular disorders, non-genetic myopathies, genetic myopathies, and/or for regulating skeletal or cardiac muscle disuse, diseases and aging.

In one aspect, the present invention relates to the maintaining and/or preserving the excitation:contraction:relaxation coupling by blocking RANK/RANKL function.

In one aspect, the present invention relates to the use of one or more RANK/RANKL antagonists to maintain and/or preserve the excitation:contraction:relaxation coupling for treating neuromuscular disorders, non-genetic myopathies, genetic myopathies, and/or for regulating skeletal or cardiac muscle disuse, diseases and aging.

In one aspect, the present invention relates to the use of one or more RANK/RANKL antagonists to reduce loss of muscle strength associated with neuromuscular disorders, non-genetic myopathies or genetic myopathies.

In one aspect, the present invention relates to the use of one or more RANK/RANKL antagonists to reduce loss of muscle strength associated with skeletal or cardiac muscle disuse, diseases and aging.

The present invention relates to the use of RANK/RANKL antagonists for regulating skeletal or cardiac muscle disuse, diseases and aging.

The present invention relates to RANK/RANKL as a new pathway for regulating fast-to-slow twitch fibre transformation.

In one aspect the present invention relates to a method for treating neuromuscular disorders, non-genetic myopathies, genetic myopathies, and/or for regulating skeletal or cardiac muscle disuse, diseases and aging comprising administering of one or more RANK/RANKL antagonists to a patient in need thereof.

In one aspect, the present invention relates to a method for maintaining and/or preserving the excitation:contraction:relaxation coupling comprising the step of administering one or more RANK/RANKL RANKL antagonists to a patient in need thereof.

The present invention relates to a method for regulating skeletal or cardiac muscle disuse, diseases and aging comprising the step of administering one or more RANK/RANKL RANKL antagonists to a patient in need thereof.

In one aspect, there is provided the use of one ore more RANK/RANKL antagonists for the treatment of neuromuscular disorders, non-genetic myopathies, genetic myopathies, muscle disuse, muscle atrophy associated with drugs in which skeletal muscles are directly or indirectly affected.

In one aspect the present invention relates to the use of one or more RANK/RANKL antagonists for treating skeletal muscle pathologies and underlying processes where excitation:contraction:relaxation coupling and mobilization are impaired which lead to muscle dysfunction and/or progressive muscle degeneration.

In one aspect the present invention relates to the one ore more RANK/RANKL antagonists to reduce loss of strength following muscle disuse.

In one aspect the present invention relates to the one ore more RANK/RANKL antagonists to reduce loss of strength associated with muscle atrophy.

In one aspect, the muscle disease or pathology is a skeletal or cardiac muscle disease or pathology.

In one aspect:
the RANK/RANKL antagonist is an OPG (osteoprotegerin) variant or an anti RANKL antibody;
the RANK/RANKL antagonist is a monoclonal anti-RANKL antibody; or
the RANK/RANKL antagonist is small interfering RNA, a microRNA, a precursor molecule, a ribozyme, an antisense, or an aptamer targeting RANKL.

In one aspect the RANK/RANKL antagonist is a humanized monoclonal anti-RANKL antibody.

In one aspect the RANK/RANKL antagonist is Denosumab.

In one aspect the RANK/RANKL antagonist is OPG.

In one aspect the RANK/RANKL antagonist is small interfering RNA, a microRNA, a precursor molecule, a ribozyme, an antisense, or an aptamer targeting RANKL.

In one aspect,
the RANKL antagonist is an OPG (osteoprotegerin) variant or an anti RANKL antibody;
the RANKL antagonist is a monoclonal anti-RANKL antibody;
the RANKL antagonist is a humanized monoclonal anti-RANKL antibody;
the RANKL antagonist is Denosumab; or
the RANKL antagonist is OPG.

In a further aspect the neuromuscular disorders, non-genetic myopathies and/or genetic myopathies include Duchenne muscular dystrophy, Berker muscular dystrophy, channelopathies, congenital myopathies (central core disease, multicore disease), Brody disease (SERCA1), amyotrophic lateral sclerosis, malignant hyperthermia, myopathy, muscle pain and rhabdomyolysis associated with drugs (ex. lipid lowering drugs named statin or rapamycin and FK506 (both immunosuppressive drugs), muscle dysfunction and fatigue associated with aging, muscle dysfunction and weakness following renal failure, muscle dysfunction and weakness following heart failure, muscle dysfunction associated with diabetes, muscle dysfunction and weakness following chronic obstructive pulmonary disease (COPD), muscle atrophy and dysfunction following AIDS, muscle dysfunction following sepsis (septicemia), muscle weakness, atrophy and fatigue associated with Cushing's syndrome or prolonged administration of glucocorticoid drugs (e.g asthma, rheumatoid arthritis or another inflammatory diseases) muscle dysfunction following cast immobilization and prologed bed rest and denervation, muscle dysfunction and cachexia associated with cancer, muscle dysfunction following ischemia/reperfusion, muscle dysfunction following prolonged muscular activity (e.g. running a marathon), myositis ossificans, muscle damage following eccentric contraction as well as cardiac diseases and dysfunction.

In one aspect, Excitation-contraction-relaxation cycle/coupling (E-C-R) comprises the following major events: (1) initiation and propagation of an action potential along the sarcolemma and transverse (T)-tubular system; (2) detection of the T-system depolarization signal and signal transmission from the T-tubule to the sarcoplasmic reticulum (SR) membrane; (3) $Ca^{2+}$ release from the SR; (4) transient rise of myoplasmic $[Ca^{2+}]_i$; (5) transient activation of the $Ca^{2+}$-regulatory system and of the contractile apparatus; (6) $Ca^{2+}$ reuptake by the SR $Ca^{2+}$ pump and $Ca^{2+}$ binding to myoplasmic sites.

In a further aspect, the E-C-R involves ryanodine receptor/$Ca^{2+}$ release channels, ryanodine, calstabin, L-type voltage dependent channels, dihydropyridine and cytosolic mobilization, sarco/endoplasmic reticulum $Ca^{2+}$ ATPase, SERCA/phospholamban.

In one aspect, the present invention relates to use and methods for the treatment of several myopathies and chronic diseases in which skeletal muscles are directly or indirectly affected, including neuromuscular disorders and/or genetic or non genetic myopathies, sepsis, aging, and critical illness myopathies, muscle dysfunction associated with drug prescriptions, muscle dysfunction associated with various chronic diseases, muscle disuse as well as cardiac diseases and dysfunctions.

In a further embodiment, the invention relates to a method of treating neuromuscular disorders and genetic myopathies, comprising administering to the animal a combination which comprises (a) at least one RANK/RANKL antagonist or a pharmaceutically acceptable salt thereof or composition comprising same and (b) at least one compound selected from compounds indicated for the treatment of neuromuscular disorders and or genetic myopathies, sepsis, aging, and critical illness myopathies, muscle dysfunction associated with drug prescriptions, muscle dysfunctions associated with various chronic diseases, muscle disuse as well as cardiac diseases and dysfunction; a combination comprising (a) and (b) as defined above and optionally at least one pharmaceutically acceptable carrier for simultaneous, separate or sequential use, in particular for the treatment of neuromuscular disorders and or genetic myopathies, sepsis, aging, and critical illness myopathies, muscle dysfunction associated with drug prescriptions, muscle dysfunction associated with various chronic diseases, muscle disuse as well as cardiac diseases and dysfunctions; a pharmaceutical composition comprising such a combination; the use of such a combination for the preparation of a medicament for neuromuscular disorders and or genetic myopathie, sepsis, aging, and critical illness myopathies, muscle dysfunction associated with drug prescriptions, muscle dysfunction associated with various chronic diseases, muscle disuse as well as cardiac diseases and dysfunctions; and to a commercial package or product comprising such a combination.

In one aspect the compound indicated for the treatment of neuromuscular disorders and or genetic myopathies, sepsis, aging, and critical illness myopathies, muscle dysfunction associated with drug prescriptions, muscle dysfunctions associated with various chronic diseases, muscle disuse as well as cardiac diseases and dysfunction is one or more of:
  angiotensin converting enzyme (ACE) inhibitors (Sulfhydryl-containing agents (e.g. Captopril or Zofenopril); Dicarboxylate-containing agents (e.g. Enalapril, Ramipril, Quinapril, Perindopril, Lisinopril, Benazepril, Imidapril, Zofenopril or Trandolapril); Phosphonate-containing agents (e.g. Fosinopril);
  hormonal therapies (e.g. testosterone, growth hormones, insulin growth factor, glucocorticoids (e.g. prednisolone, prednosol, deflazacort);
  β2 agonists (e.g. clenbuterol or formoterol);
  proteolytic inhibitors for calpain;
  lysosomal enzymes and ubiquitin-proteasome system;
  antimyostatin therapy; or
  nutritional supplement therapies (e.g. vitamin D, proteins, branched chain amino acids).

In one aspect the at least one RANK/RANKL antagonist or a pharmaceutically acceptable salt thereof or composition comprising same can be used in combination with therapy indicated for the treatment of neuromuscular disorders and or genetic myopathies, sepsis, aging, and critical illness myopathies, muscle dysfunction associated with drug prescriptions, muscle dysfunctions associated with various chronic diseases, muscle disuse as well as cardiac diseases and dysfunction such as electric stimulation.

Administration "in combination with" one or more further therapeutic agents includes simultaneous (concurrent) and consecutive administration in any order.

In one aspect said one or more RANK/RANKL antagonists or said pharmaceutical composition and said further therapeutic active agent are administered simultaneous.

In one aspect said one or more RANK/RANKL antagonists or said pharmaceutical composition and said further therapeutic active agent are administered consecutively.

When the combination partners employed in the combinations as disclosed herein are applied in the form as marketed as single drugs, their dosage and mode of administration can take place in accordance with the information provided on the package insert of the respective marketed drug in order to result in the beneficial effect described herein, if not mentioned herein otherwise.

The terms "RANKL" or "RANK Ligand" or "RANK Ligand polypeptide" when used herein encompass "native sequence RANKL polypeptides" and "RANKL variants". "RANKL" is a designation given to those polypeptides which are encoded by the nucleic acid molecules comprising the polynucleotide sequences shown in WO98/28426 published Jul. 2, 1998 (and referred to therein as RANK ligand) and variants thereof, nucleic acid molecules comprising the sequence shown in WO98/28426, and variants thereof as well as fragments of the above which have the biological activity of the native sequence RANKL. A "native sequence" RANKL polypeptide comprises a polypeptide having the same amino acid sequence as the corresponding RANKL polypeptide derived from nature. Such native sequence RANKL polypeptides can be isolated from nature or can be produced by recombinant and/or synthetic means. The term "native sequence RANKL polypeptide" specifically encompasses naturally-occurring truncated or secreted forms (e.g., an extracellular domain sequence), naturally-occurring variant forms (e.g., alternatively spliced forms) and naturally-occurring allelic variants of the polypeptide. The term "RANKL" includes those polypeptides described in Anderson et al., Nature, 390:175-179 (1997); Lacey et al., Cell, 93:165-176 (1998); Wong et al., J. Exp. Med., 186: 2075-2080 (1997); Yasuda et al., PNAS, 95:3597-3602 (1998); U.S. Pat. No. 6,242,213 issued Jun. 5, 2001; WO99/29865 published Jun. 17, 1999 (referred to as TRANCE). Recombinant human RANK Ligand is also commercially available from Enzo Life Sciences.

"RANK Ligand variant" means an RANK Ligand polypeptide having at least about 80% amino acid sequence identity—with the amino acid sequence of a native sequence RANK Ligand or RANK Ligand ECD. Preferably, the RANK Ligand variant binds OPG receptor or RANK receptor. Optionally, the RANK Ligand variant will have at least one activity identified herein for a native sequence RANK Ligand polypeptide or agonist or antagonist molecule. Such RANK Ligand variant polypeptides include, for instance, RANK Ligand polypeptides wherein one or more amino acid residues are added, or deleted, at the N- and/or C-terminus, as well as within one or more internal domains, of the full-length amino acid sequence. RANK Ligand variant polypeptides do not encompass the native RANK Ligand polypeptide sequence.

The terms "OPG" or "osteoprotegerin" or "OPG receptor" when used herein encompass "native sequence OPG polypeptides" and "OPG variants" (which are further defined herein). "OPG" is a designation given to those polypeptides which are encoded by the nucleic acid molecules comprising the polynucleotide sequences shown in Simonet et al., Cell, 89:309 (1997) and variants thereof, nucleic acid molecules comprising the sequence shown in Simon et. al., supra and variants thereof as well as fragments of the above. The OPG polypeptides of the invention may be isolated from a variety of sources, such as from human tissue types or from another source, or prepared by recombinant and/or synthetic methods. A "native sequence" OPG polypeptide comprises a polypeptide having the same amino acid sequence as the corresponding OPG polypeptide derived from nature. Such native sequence OPG polypeptides can be isolated from nature or can be produced by recombinant and/or synthetic means. The term "native sequence OPG polypeptide" specifically encompasses naturally-occurring truncated or secreted forms (e.g., an extracellular domain sequence), naturally-occurring variant forms (e.g., alternatively spliced forms) and naturally-occurring allelic variants of the polypeptide. The OPG polypeptides of the invention include the polypeptides described as "FDCR-1" and "OCIF" in Yasuda et al., Endocrinology, 139:1329 (1998) and Yun et al., J. Immunol., 161:6113-6121 (1998).

"OPG variant" means an OPG polypeptide having at least about 80% amino acid sequence identity with the amino acid sequence of a native sequence OPG or OPG ECD. Preferably, the OPG variant binds RANKL, and more preferably, binds to the full length RANK Ligand.

The terms "RANK" "Rank" or "RANK receptor" when used herein encompass "native sequence RANK polypeptides" and "RANK variants". "RANK" is a designation given to those polypeptides which are encoded by the nucleic acid molecules comprising the polynucleotide sequences shown in WO98/28426 published Jul. 2, 1998 and variants thereof, nucleic acid molecules comprising the sequence shown in WO98/28426 and variants thereof as well as fragments of the above. The RANK polypeptides of the invention may be isolated from a variety of sources, such as from human tissue types or from another source, or prepared by recombinant and/or synthetic methods. A "native sequence" RANK polypeptide comprises a polypeptide having the same amino acid sequence as the corresponding RANK polypeptide derived from nature. Such native sequence RANK polypeptides can be isolated from nature or can be produced by recombinant and/or synthetic means. The term "native sequence RANK polypeptide" specifically encompasses naturally-occurring truncated or secreted forms (e.g., an extracellular domain sequence), naturally-occurring variant forms (e.g., alternatively spliced forms) and naturally-occurring allelic variants of the polypeptide. The RANK polypeptides of the invention include the polypeptides described in Anderson et al., Nature, 390:175-179 (1997); U.S. Pat. No. 6,017,729 issued Jan. 25, 2000; and Lacey et al., Cell, 93:165-176 (1998).

Anderson et al., Nature, 390:175-179 (1997) reports the amino acid sequence of human RANKL protein (Genbank Accession No. AAB86811.1; SEQ ID NO: 1):

MRRASRDYTK YLRGSEEMGG GPGAPHEGPL HAPPPPAPHQ PPAASRSMFV ALLGLGLGQV VCSVALFFYF RAQMDPNRIS EDGTHCIYRI LRL-HENADFQ DTTLESQDTK LIPDSCRRIK QAFQ-GAVQKE LQHIVGSQHI RAEKAMVDGS WLD-LAKRSKL EAQPFAHLTI NATDIPSGSH KVSLSSWYHD RGWAKISNMT FSNGKLIVNQ DGFYYLYANI CFRHHETSGD LATEYLQLMV YVTK-TSIKIP SSHTLMKGGS TKYWSGNSEF HFYSINVGGF FKLRSGEEIS IEVSNPSLLD PDQDATYFGA FKVRDID

"RANK variant" means a RANK polypeptide having at least about 80% amino acid sequence identity with the amino acid sequence of a native sequence RANK or RANK ECD. Preferably, the RANK variant binds RANKL, and more preferably, binds to full length RANK Ligand polypeptide. Such RANK variant polypeptides include, for instance, RANK polypeptides wherein one or more amino acid residues are added, or deleted, at the N- and/or C-terminus, as well as within one or more internal domains, of the full-length amino acid sequence.

An "extracellular domain" or "ECD" refers to a form of the polypeptide which is essentially free of the transmembrane and cytoplasmic domains. Ordinarily, an ECD form of a polypeptide will have less than about 1% of such transmembrane and/or cytoplasmic domains and preferably, will have less than about 0.5% of such domains. It will be understood that any transmembrane domain(s) identified for the polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified. In a preferred embodiment, the ECD will consist of a soluble, extracellular domain sequence of the polypeptide which is free of the transmembrane and cytoplasmic or intracellular domains (and is not membrane bound).

"Percent (%) amino acid sequence identity" with respect to the ligand or receptor polypeptide sequences identified herein is defined as the percentage of amino acid residues in a candidate sequence that are identical with the amino acid residues in such a ligand or receptor sequence identified herein, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software.

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5λSSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42.degree. C., with washes at 42° C. in 0.2×SSC (sodium chloride/sodium citrate) and 50% formamide at 55° C., followed by a high-stringency wash consisting of 0.1×SSC containing EDTA at 55° C.

The term "RANK/RANKL antagonist" is used in the broadest sense, and includes any molecule that partially or fully blocks, inhibits, or neutralizes one or more biological activities of RANKL or RANK, in vitro, in situ, or in vivo. Examples of such biological activities of RANKL polypeptides include binding of RANKL to RANK. Examples of such biological activities of RANK polypeptides include binding of RANK to RANKL. An antagonist may function in a direct or indirect manner. For instance, the antagonist may function to partially or fully block, inhibit or neutralize one or more biological activities of RANKL or RANK, in vitro, in situ, or in vivo as a result of its direct binding to RANKL, or RANK. The antagonist may also function indirectly to partially or fully block, inhibit or neutralize one or more biological activities of RANKL or RANK, in vitro, in situ, or in vivo as a result of, e.g., blocking or inhibiting another effector molecule.

The term "RANKL antagonist" refers to any molecule that partially or fully blocks, inhibits, or neutralizes a biological activity of RANKL and includes, but are not limited to, soluble forms of OPG receptor or RANK receptor such as an extracellular domain sequence of OPG or RANK, OPG receptor immunoadhesins, RANK receptor immunoadhesins, OPG receptor fusion proteins, RANK receptor fusion proteins, covalently modified forms of OPG receptor, covalently modified forms of RANK receptor, OPG variants, RANK variants, OPG receptor antibodies, RANK receptor antibodies, and RANKL antibodies. To determine whether an RANKL antagonist molecule partially or fully blocks, inhibits or neutralizes a biological activity of RANKL, assays may be conducted to assess the effect(s) of the antagonist molecule on, for example, binding of RANKL to OPG or to RANK, or by determining the effect on muscle function and/or on SERCA activity by the RANKL. Such assays may be conducted in known in vitro or in vivo assay formats, for instance, in cells expressing OPG and/or RANK. Preferably, the RANKL antagonist employed in the methods described herein will be capable of blocking or neutralizing at least one type of RANKL activity, which may optionally be determined in assays such as described herein (and in the Examples). Optionally, an antagonist will be capable of reducing or inhibiting binding of RANKL to OPG and/or to RANK by at least 50%, preferably, by at least 90%, more preferably by at least 99%, and most preferably, by 100%, as compared to a negative control molecule, in a binding assay. In one embodiment, the antagonist will comprise antibodies which will competitively inhibit the binding of RANKL to OPG or RANK. Methods for determining antibody specificity and affinity by competitive inhibition are known in the art [see, e.g., Harlow et al., Antibodies: A Laboratory Manual, Cold Spring Harbor Laboratory Press, Cold Spring Harbor, N.Y. (1998); Colligan et al., Current Protocols in Immunology, Green Publishing Assoc., NY (1992; 1993); Muller, Meth. Enzym., 92:589-601 (1983)].

In one aspect the RANKL antagonist is an OPG variant or an anti-RANKL antibody. In a further aspect the RANKL antagonist is a monoclonal anti-RANKL antibody. In a further aspect the RANKL antagonist is a humanized monoclonal anti-RANKL antibody. In a further aspect the RANKL antagonist is Denosumab. Denosumab is a full human antibody that shares the pharmalogical attributes of OPG but has a significant longer half-life allowing less frequent administration (current Opinion in Pharmalogy 2005 5: 618-625). In a further aspect the RANKL antagonist is OPG.

The term "antibody" is used in the broadest sense and specifically covers, for example, single monoclonal antibodies which specifically bind RANKL or RANK, antibody compositions with polyepitopic specificity, single chain antibodies, and fragments of antibodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed ?as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Methods of making chimeric antibodies are known in the art.

"Humanized" forms of non-human (e.g., murine) antibodies are chimeric immunoglobulins, immunoglobulin chains or fragments thereof (such as Fv, Fab, Fab', F(ab')₂ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992). The humanized antibody includes a PRIMATIZED™ antibody wherein the antigen-binding region of the antibody is derived from an antibody produced by immunizing macaque monkeys with the antigen of interest. Methods of making humanized antibodies are known in the art.

Human antibodies can also be produced using various techniques known in the art, including phage-display libraries. Hoogenboom and Winter, J. Mol. Biol., 227:381 (1991); Marks et al., J. Mol. Biol., 222:581 (1991). The techniques of Cole et al. and Boerner et al. are also available for the preparation of human monoclonal antibodies. Cole et al., Monoclonal Antibodies and Cancer Therapy, Alan R. Liss, p. 77 (1985); Boerner et al., J. Immunol., 147(1):86-95 (1991).

"Antibody fragments" comprise a portion of an intact antibody, preferably the antigen binding or variable region of the intact antibody. Examples of antibody fragments include Fab, Fab', F(ab').sub.2, and Fv fragments; diabodies; linear antibodies (Zapata et al., Protein Eng. 8(10): 1057-1062); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab').sub.2 fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the V.sub.H-V.sub.L dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')₂ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the V.sub.H and V.sub.L domains of antibody, wherein these domains are present in a single polypeptide chain. Preferably, the Fv polypeptide further comprises a polypeptide linker between the V.sub.H and V.sub.L domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (V.sub.H) connected to a light-chain variable domain (V.sub.L) in the same polypeptide chain (V.sub.H-V.sub.L). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the protein natural environment will not be present. Ordinarily, however, isolated protein will be prepared by at least one purification step.

A "liposome" is a small vesicle composed of various types of lipids, phospholipids and/or surfactant which is useful for delivery of a drug (such as a polypeptide or antibody thereto) to a mammal. The components of the liposome are commonly arranged in a bilayer formation, similar to the lipid arrangement of biological membranes.

Small interfering RNA (short interfering RNA, silencing RNA, siRNA) is a class of double-stranded RNA-molecules, which are 19-30 nucleotides, preferably 20-25 nucleotides long. siRNAs are involved in the RNA-interference of the expression of a specific gene. siRNAs are cut from long double-stranded RNAs by the RNase III Dicer. They can also be derived by chemical synthesis. They also play a role in antiviral mechanisms or in shaping the chromatin structure of a genome. In molecular research, synthetic siRNAs can also be used in RNA-interference (RNAi) to regulate down the expression of specific target genes. With their ability to knock down essentially any gene of interest, siRNAs can been used to knock down RANK or RANKL.

MicroRNAs (miRNAs) are posttranscriptional regulators that bind to complementary sequences in the 3'UTR of mRNA transcripts, usually resulting in gene silencing. They are short RNA molecules which are about 22 nucleotides long.

Precursor molecules, e.g. precursor molecules of siRNA and/or miRNA may be a substrate for the siRNA/miRNA-biogenesis-apparatus of the target cell. This comprises, for example, RNA precursor molecules such as double-stranded RNA (dsRNA) or short hairpin RNA-molecules (shRNA), which are processed by endonucleases such as Drosha and/or Pasha to siRNA-molecules or miRNA-molecules, respectively. For this reason, for example dsRNA-molecules or short hairpin RNA-molecules (shRNA) having a length of more than 27 nucleotides, preferably more than 30 up to 100 nucleotides or longer, and mostly preferred dsRNA-molecules having a length of 30-50 nucleotides, can be used.

Further precursor molecules according to the invention may be DNA constructs encoding dsRNA, shRNA, siRNA and/or miRNA, whereby the coding elements are controlled by regulatory elements allowing an expression of dsRNA, shRNA, siRNA and/or miRNA in the target cell. Examples for such control elements are polymerase II promoters or polymerase III promoters such as, for example, U6 or H1.

Ribozymes are catalytic RNAs which possess a well defined structure that enables them to catalyze a chemical reaction. Apart from naturally occurring ribozymes they can be made artificially and be tailored to interact with nucleic acids and proteins.

Antisense oligonucleotides are single strands of DNA or RNA that are complementary to a chosen sequence. They are between 10 and 35 nucleotides long, preferably about 20-25 nucleotides. Antisense DNA oligonucleotides can target specific, complementary RNA, and upon binding DNA/RNA hybrids are formed. Antisense RNA oligonucleotides can bind to mRNA by binding to mRNA strands.

Aptamers are oligonucleic acid (DNA or RNA aptamers) or peptide molecules (peptide aptamers) that bind to a specific target molecule. Aptamers can be used for therapeutic purposes as macromolecular drugs. Aptamers can be created by selecting them from a large random sequence pool.

In one aspect, a "small molecule" as defined herein has a molecular weight below about 500 Daltons.

In one aspect, an effective amount and or a therapeutically effective amount of one or more RANK/RANKL antagonists is used in the uses and methods described herein. The term "effective amount" is a concentration or amount of an antagonist which results in achieving a particular stated purpose. An "effective amount" of an antagonist thereof may be determined empirically. Furthermore, a "therapeutically effective amount" is a concentration or amount of an agonist/antagonist which is effective for achieving a stated therapeutic effect. This amount may also be determined empirically.

"Treatment" "treating" or "therapy" refer to both therapeutic treatment and prophylactic or preventative measures.

It is noted in that the present invention when the RANK/RANKL antagonist is a small molecule it is intended to encompass all pharmaceutically acceptable ionized forms (e.g., salts) and solvates (e.g., hydrates) of the RANK/RANKL antagonists, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers.

It is noted in that the present invention when the RANK/RANKL antagonist is a small molecule, there is also provided pharmaceutically acceptable salts of the RANK/RANKL antagonist. By the term pharmaceutically acceptable salts are meant those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, trifluoroacetic, citric, methanesulphonic, formic, benzoic, malonic, naphthalene-2-sulphonic and benzenesulphonic acids. Salts derived from amino acids are also included (e.g. L-arginine, L-Lysine). Salts derived from appropriate bases include alkali metals (e.g. sodium, lithium, potassium) and alkaline earth metals (e.g. $Ca^{2+}$, magnesium).

With regards to pharmaceutically acceptable salts, see also the list of FDA approved commercially marketed salts listed in Table I of Berge et al., Pharmaceutical Salts, J. of Phar. Sci., vol. 66, no. 1, January 1977, pp. 1-19.

It is noted in that the present invention when the RANK/RANKL antagonist is a small molecule, it will be appreciated by those skilled in the art that the small molecule can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It is noted in that the present invention when the RANK/RANKL antagonist is a small molecule, it will further be appreciated by those skilled in the art that the small molecule can exist in different solvate forms, for example hydrates. Solvates of the RANK/RANKL antagonist small molecule may also form when solvent molecules are incorporated into the crystalline lattice structure of the compound molecule during the crystallization process.

It will be appreciated that the amount of a RANK/RANKL antagonist required for use in treatment will vary not only with the particular antagonist selected but also with the route of administration, the nature of the condition for which treatment is required and the age and condition of the patient and will be ultimately at the discretion of the attendant physician.

When RANK/RANKL antagonist or pharmaceutically acceptable salts thereof are used in combination with a further therapeutic agent or therapy indicated for the treatment of neuromuscular disorders and genetic myopathies the dose of each compound may be either the same as or differ from that when the compound is used alone. Appropriate doses will be readily appreciated by those skilled in the art.

While it is possible that, for use in therapy, the RANK/RANKL antagonist may be administered as the raw chemical it is preferable to present the active ingredient as a pharmaceutical composition. The invention thus further provides a pharmaceutical composition comprising the RANK/RANKL antagonist or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The compositions may, where appropriate, be conveniently presented in discrete dosage units and may be prepared by any of the methods well known in the art of pharmacy. All methods include the step of bringing into association the active with liquid carriers or finely divided solid carriers or both and then, if necessary, shaping the product into the desired composition.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The RANK/RANKL antagonist may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the RANK/RANKL antagonist may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are for example presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration, the compounds or combinations may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds or combinations are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds or combinations may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

As used herein, the expression "an acceptable carrier" means a vehicle for containing the compounds obtained by the method of the invention that can be administered to a subject without adverse effects. Suitable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

In one aspect, there is provided methods for identifying candidate compounds. Compounds capable of modulating, preventing or reducing binding of RANK to RANKL may be useful for treating neuromuscular disorders, non-genetic myopathies, genetic myopathies, and/or for regulating skeletal or cardiac muscle disuse, diseases and aging or for maintaining and/or preserving the excitation:contraction:relaxation coupling.

The methods of the present invention are also useful for screening libraries of compounds in order to identify compounds that may be used as compounds for treating neuromuscular disorders, non-genetic myopathies, genetic myopathies, and/or for regulating skeletal or cardiac muscle disuse, diseases and aging or for maintaining and/or preserving the excitation:contraction:relaxation coupling.

The expression "candidate compound" includes compounds such as small molecules (as defined earlier), nucleic acids, antibodies or polypeptides capable of interacting with a biological target molecule, in particular with a protein, in such a way as to modify, block or modulate the biological activity thereof. The expression includes compounds capable of interacting with RANK or RANKL in such a way that the RANK/RANKL/OPG pathway is modified. In one aspect the compounds are capable of increasing SERCA expression and activity and $Ca^{2+}$ mobilization.

The expression "biological system" refers to a suitable biological assay or biological model. The biological assay can be an in vitro assay wherein the interaction between RANK and RANKL is measured, or the activity or expression of SERCA is measured. The biological model can be any suitable model allowing the evaluation of the interaction between RANK and RANKL is measured, or the activity or expression of SERCA is measured.

The ability of the compound to modulate, reduce and/or inhibit the interaction between RANK and RANKL or to increase the activity or expression of can be measured by method well known in the art such as ELISA assay, immunoprecipitation assay, coimmunoprecipitation assay, Western Blot assay, immunostaining or radioimmunoassay.

The present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, the preferred methods and materials are described. The issued patents, published patent applications, and references that are cited herein are hereby incorporated by reference to the same extent as if each was specifically and individually indicated to be incorporated by reference. In the case of inconsistencies, the present disclosure will prevail.

EXAMPLES

Example 1: A Role for OPG/RANK/RANKL Pathway in Fast to Slow Twitch Muscle Fiber Conversion Rationale:

Numerous studies demonstrated slow-to-fast conversion followed by a fast-to-slow reconversion in soleus (SOL) muscle during unloading and reloading, respectively. The mechanisms that trigger gene expression changes during this process remain unclear. However, it is clear that $Ca^{2+}$ ion exerts a pivotal role in regulating fast to slow transition. For example, the in vitro application of a $Ca^{2+}$ ionophore to rabbit fast skeletal muscle cells induces an increase in resting $[Ca^{2+}]_i$ and conversion from fast to slow fiber type, which was reversible[62].

Experimental Design:

Mice were subjected to hindlimb unweighing using an apparatus similar to that described by Morey-Holton and Globus (2002)[63]. Briefly, hindlimb unloading (HU) were achieved by using the tail to lift the pelvis so that the hindlimbs did bear weight. The suspension harness was attached to a tail cast and linked to a 360° swivel at the top of the cage. The 10 d period of HU has been shown to be sufficient to produce changes in muscle mass, contractile properties, and myosin isoform type[64]. Among the muscles displaying changes in these characteristics during HU, the most dramatic differences were observed with the SOL. The level of atrophy in the SOL muscle after 10 d of HU resembles changes observed in human muscle following prolonged stays in space or cast immobilization, making it a good model to test muscle atrophy and regrowth.

Figure 15A:
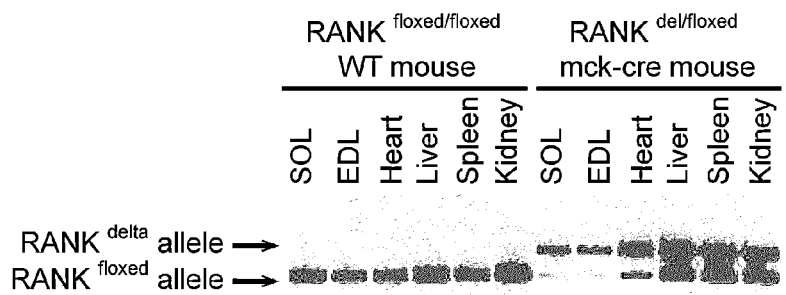
FIG. 15: RANK/RANKL/OPG triad in skeletal muscle.
Figure 15B:
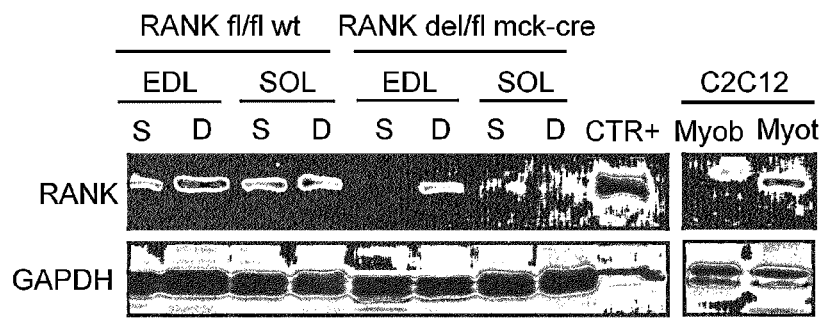
Figure 15C:
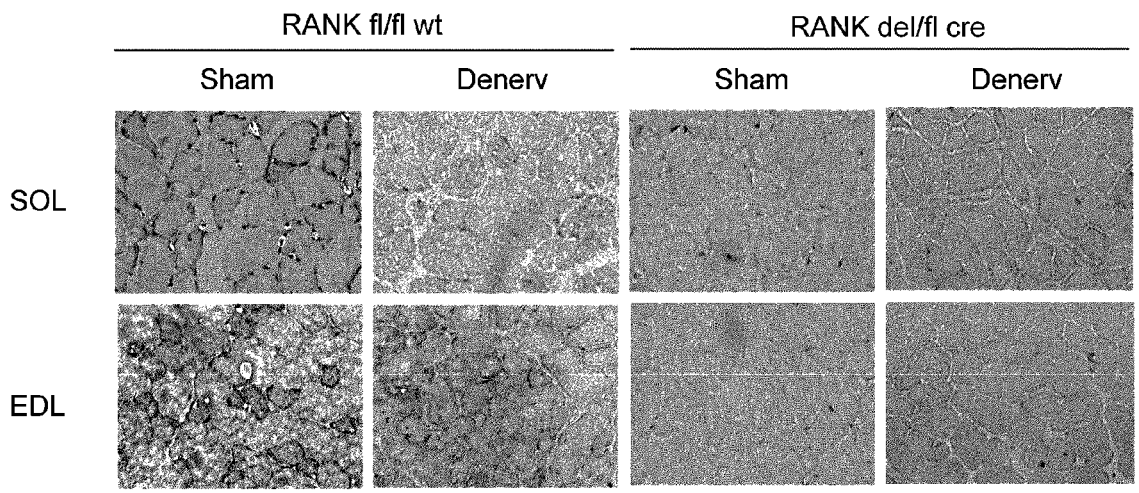
Figure 16A:
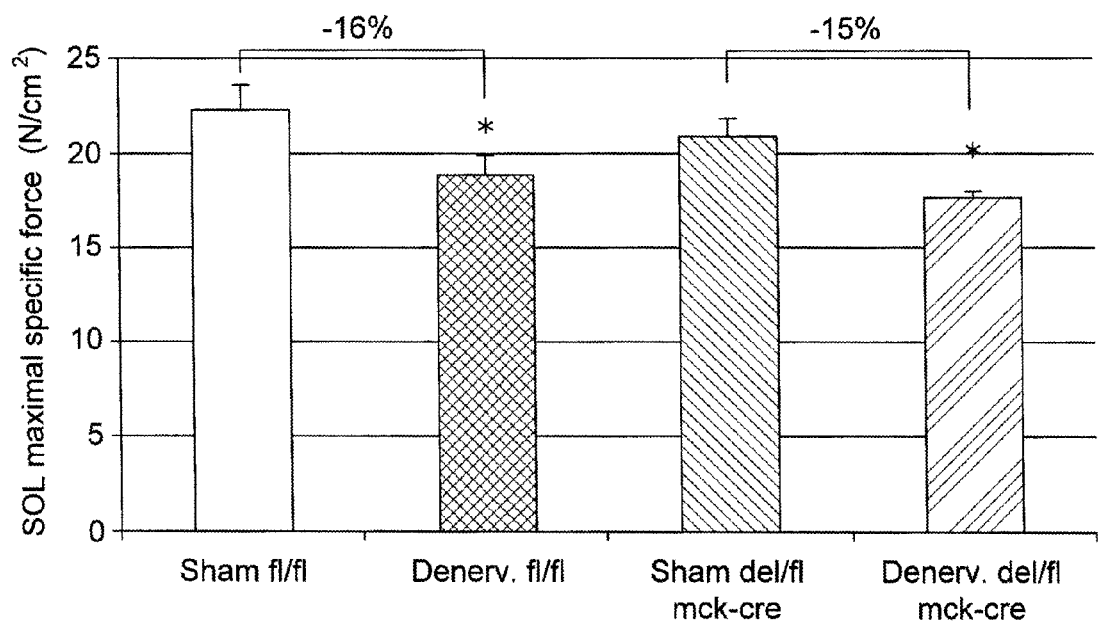
Figure 16B:
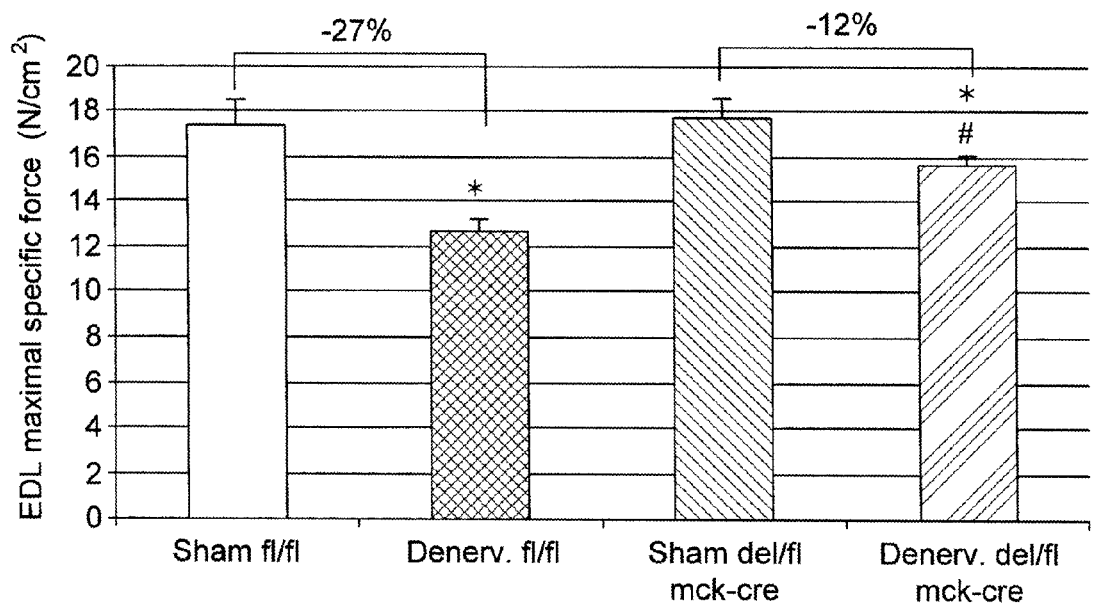
Figure 16C:
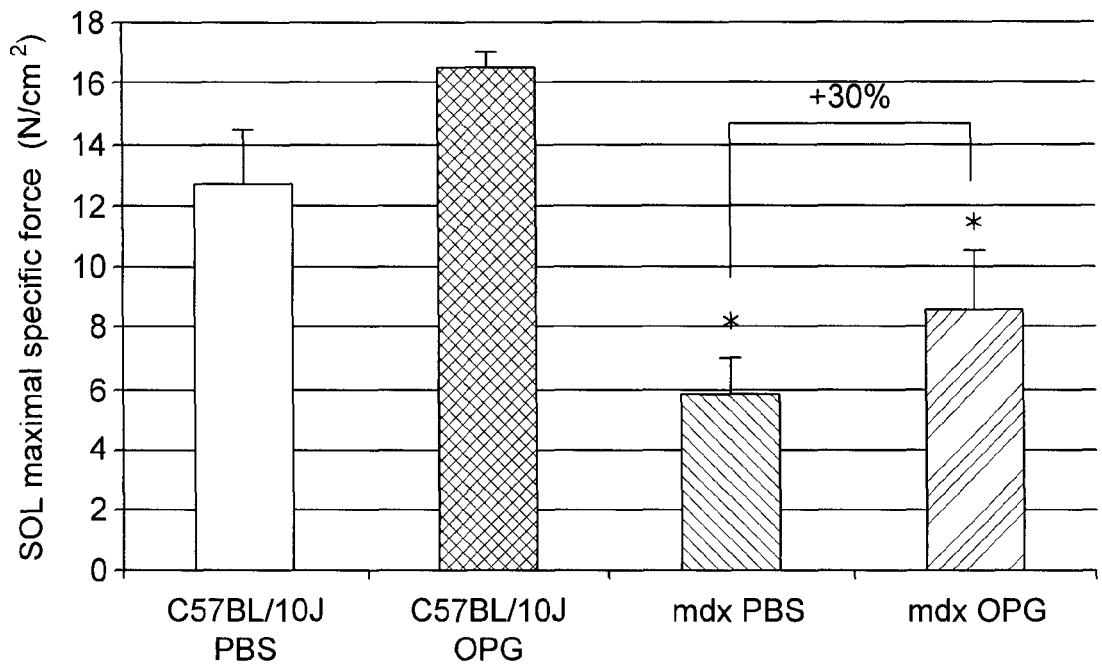
Figure 16D:
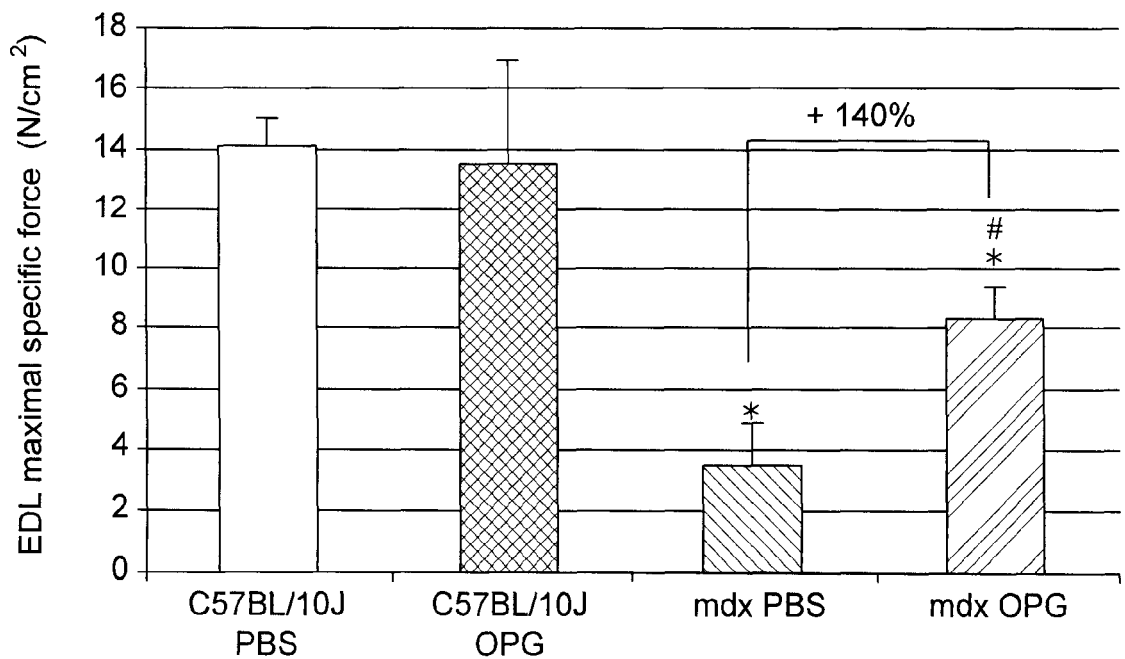
Figure 16E:
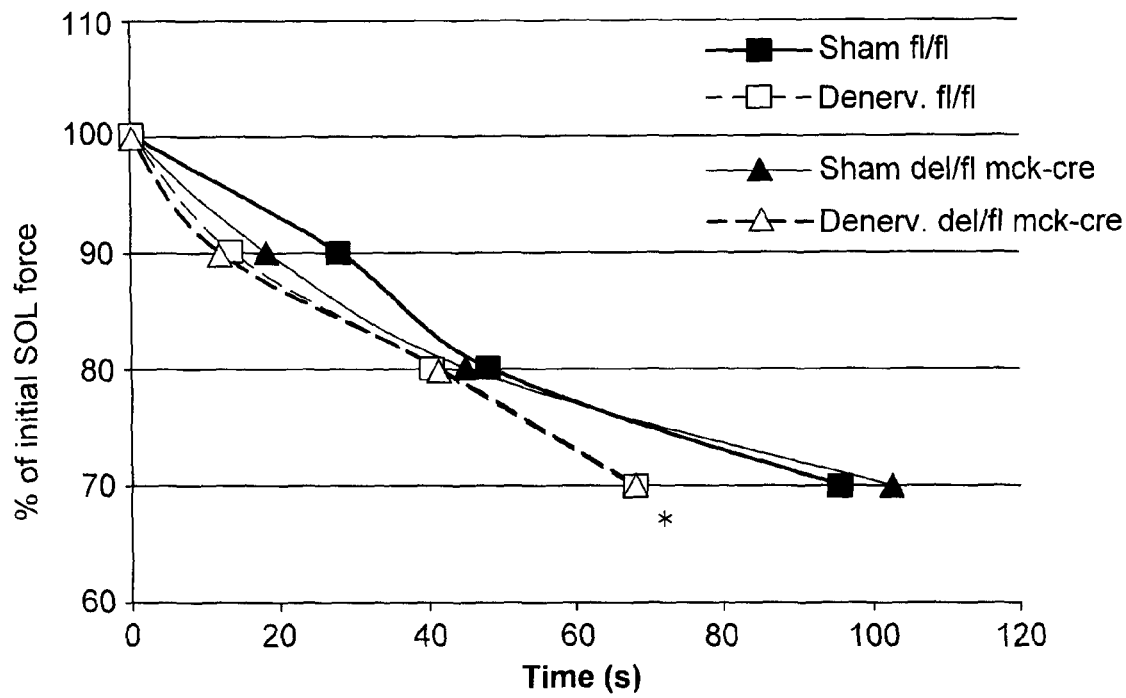
Figure 16F:
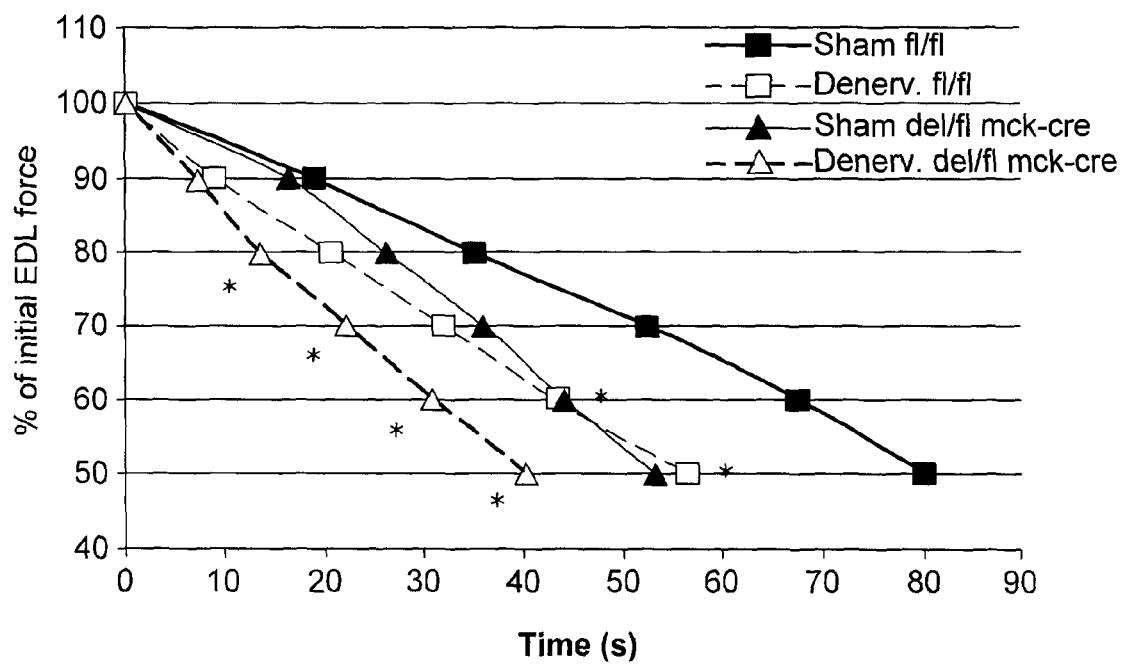
Figure 16G:
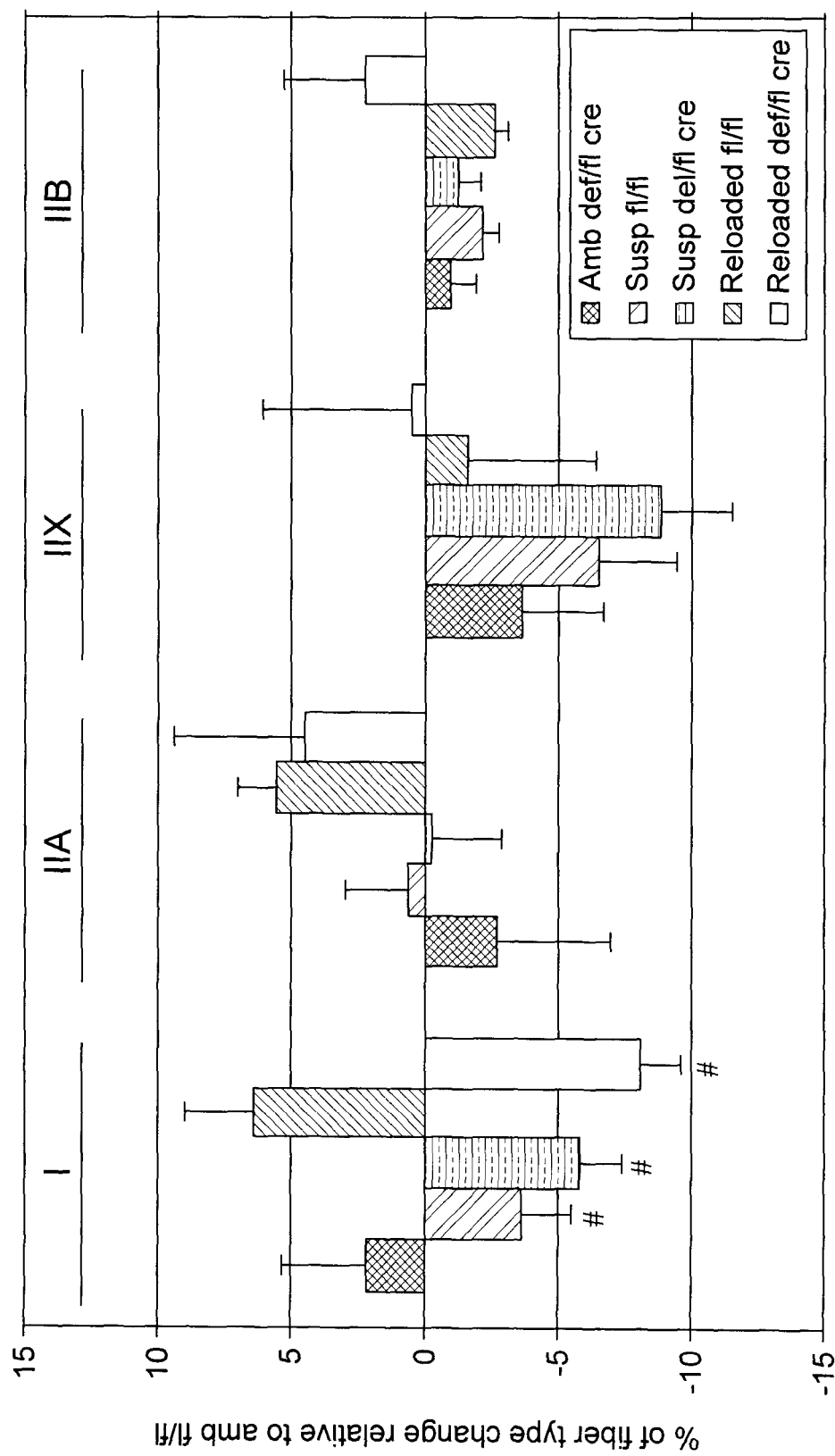

To investigate the role of RANK in skeletal muscle, we generated and crossed Rank$^{fl/fl}$ mice with muscle creatine kinase (MCK)-Cre mice in which Cre-mediated recombination occurs in postmitotic myofibres[67]. These mice were selectively deficient in RANK in skeletal muscle (FIGS. 15A, 15B, 15C).

Direct genetic approaches with knock-out mice will be used to study the role of RANK in muscle fiber reconversion: RANK$^{fl/fl}$, and RANK$^{del/fl}$ were assigned to the following groups: (1) ambulatory controls, (2) 10 d HU only, (3) 10 d HS followed by 7 d of reloading. These periods of suspension and reloading have been selected because they allow us to sample at times when conversion from slow-to-fast and reconversion from fast-to-slow twitch muscle fibers occur. Following the procedures, all mice from all experimental groups were anesthetized with sodium pentobarbital (50 mg/kg), and SOL muscles were excised with the tendons intact for immunohistochemical and functional analyses.

TABLE 1

Table 1: Contractile and physical properties of SOL muscle following hindlimb unloading and reloading.

| | SOL | | | | | |
|---|---|---|---|---|---|---|
| | Amb fl/fl | Susp 10 d fl/fl | Reloaded 7 d fl/fl | Amb del/fl | Susp 10 d del/fl | Reloaded 7 d del/fl |
| TPT (ms) | 55 ± 2.34 | 44 ± 2.95 * | 52.75 ± 2.9 | 48.75 ± 2.17 | 42.2 ± 1.66 * | 38 ± 1.87 # |
| ½ RT (ms) | 53.75 ± 3.2 | 40.4 ± 2.6 * | 54.75 ± 1.75 | 51.25 ± 2.72 | 44.6 ± 1.96 * | 52.25 ± 3.09 |
| Pt (g) | 6.31 ± 0.8 | 3.99 ± 0.26 * | 5.39 ± 0.33 | 5.42 ± 0.17 | 3.27 ± 0.23 * | 4.81 ± 0.86 |
| Po (g) | 25.92 ± 0.94 | 15.75 ± 0.45 * | 21.35 ± 1.05 | 26.14 ± 0.87 | 14.73 ± 0.63 * | 20.59 ± 1.73 |
| Po (N/cm2) | 24.32 ± 2.71 | 20.77 ± 0.78 | 20.27 ± 0.52 | 26.85 ± 1.66 | 17.99 ± 0.68 | 20.33 ± 2.75 |

TABLE 1-continued

Table 1: Contractile and physical properties of SOL muscle following hindlimb unloading and reloading.

| | SOL | | | | | |
|---|---|---|---|---|---|---|
| | Amb fl/fl | Susp 10 d fl/fl | Reloaded 7 d fl/fl | Amb del/fl | Susp 10 d del/fl | Reloaded 7 d del/fl |
| Muscle weight (mg) | 7.89 ± 1.02 | 5.54 ± 0.21 | 7.82 ± 0.32 | 7.03 ± 0.26 | 5.82 ± 0.26 | 7.51 ± 0.59 |

RANK$^{fl/fl}$ and RANK$^{del/fl}$ mice were submitted to 10 days of hindlimb unloading followed by 0 or 7 days of reloading. Ambulatory mice were used as controls. SOL muscles were incubated ex vivo and stimulated (1, 10, 50, 100 Hz at 35 V) to measure time to peak tension (TPT), half relaxation time (½ RT), maximal twitch tension (Pt), maximal absolute force (Po) and maximal specific force (sPo). Muscle weight was determined thereafter. RANK$^{del/fl}$ SOL muscles exhibit a shorter TPT after 7 days of reloading indicating that the fast-to slow reconversion does not occur (n = 4-6). Data are presented as mean +/− sem.
\* significantly different from ambulatory RANK$^{fl/fl}$,
significantly different from reloaded RANK$^{fl/fl}$, p < 0.05 (ANOVA with a post-hoc Tukey test).

Findings:

The signaling pathways involved in myofiber conversion are of particular interest for several human disorders, including muscle dystrophy, metabolic disorders, disuse induced muscle atrophy and aging. For example, the increase in abundance of slow oxidative fiber in mdx mouse model of Duchenne muscular dystrophy reduces the severity of the disease[65]. Furthermore, skeletal muscles also play an important metabolic role and the increase in the number of type I fiber enhances insulin mediated glucose uptake and protects against glucose intolerance[66]. On the other hand, fast glycolytic fibers are the first to disappear following myopathies, dystrophies, neuromuscular diseases. Our findings showed that fast to slow twitch fiber conversion did not occur in SOL muscles from Rank ko mice during the reloading period (FIGS. 1 and 16G) indicating that OPG/RANK/RANKL played a role in the regulation of muscle phenotype.

Example 2: Specific-Muscle Rank Deletion Preserves Muscle Force and Contraction:Relaxation Processes, Following Denervation Rationale:

Muscle atrophy/dysfunction is clearly under the control of several signalling pathways. Since calpain-, lysosomal-, and ubiquitin-mediated proteolysis are activated in skeletal muscle in several atrophic conditions and since atrophic signalling pathways are controlled in part by $Ca^{2+}$ concentrations, the roles of the RANK/RANKL/OPG pathway in muscle wasting and dysfunction are highly relevant following denervation.

Experimental Design:

To investigate the role of Rank in skeletal muscle, we generated and crossed a RANK$^{fl/fl}$ mice with muscle creatine kinase (MCK)-Cre mice in which Cre-mediated recombination occurs in postmitotic myofibres[67]. For the sciatic denervation, 12-16-week old, adult male RANK$^{fl/fl}$ and RANK$^{del/fl}$ mice weighing approximately 25 g were anesthetized with isoflurane and experimentally treated to produce the pathological conditions. Because food consumption may vary during illnesses, the mice were weighed and food intake was measured for all the experiments described. The mice were divided into four groups: 1—RANK$^{fl/fl}$ sham mice, 2—RANK$^{del/fl}$ sham mice, 3—RANK$^{fl/fl}$ experimental mice, and 4—RANK$^{del/fl}$ experimental mice. RANK$^{fl/fl}$ and RANK$^{del/fl}$ mice reproduce easily.

Sciatic Denervation:

The right leg were shaved, and a 5-mm incision were made on the lateral side of the thigh. The quadriceps and hamstring muscles were separated, and sciatic nerve exposed and sectioned 5 mm apart to avoid any possible reconnection. Sham mice underwent the same surgical procedures except that the sciatic nerve remained intact. The sham and experimental mice were sacrificed on day 14 post-surgery. Results showed that muscle denervation induces 40% muscle atrophy for both SOL and EDL muscles 14 d post-denervation.

Functional Analyses

Figure 2:
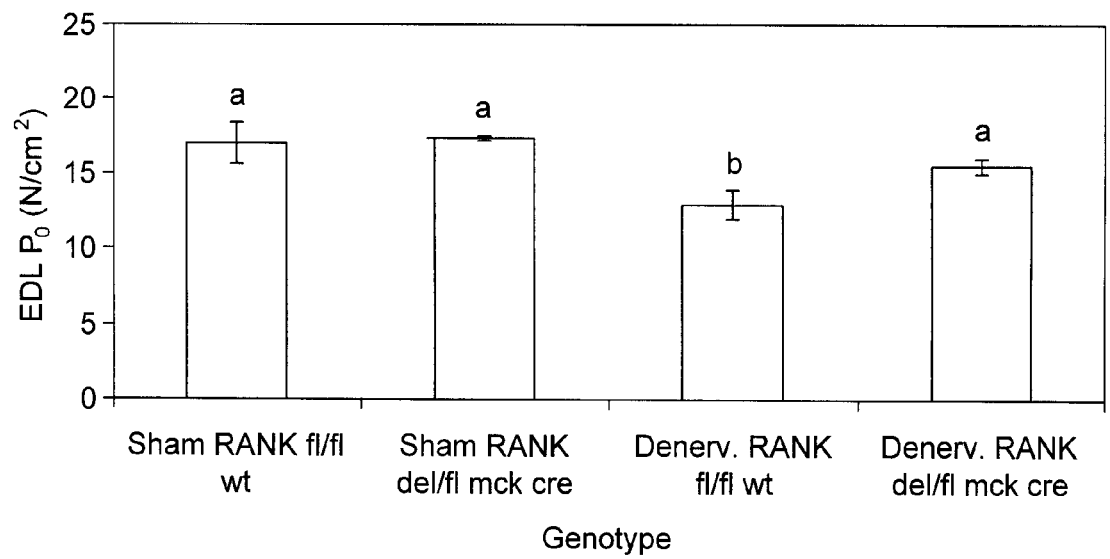
FIG. 2. RANK deletion (RANK del/fl mck cre) prevents the loss in specific force of EDL muscles from male mice following denervation. Male mice underwent sciatic denervation and contractile properties of EDL muscles were performed at 14 d post denervation (maximum specific tetanic tension; N/cm$^2$). Sham procedure consisted of exposing the nerve without transection. The deletion of RANK (RANK del/fl mck cre genotype) protects significantly against denervation-induced muscle disuse/dysfunction. When values in a column are followed by different letters, they are significantly different (n=3-4, P≤0.05; ANOVA and a Tukey's a posteriori test).
Figure 3:
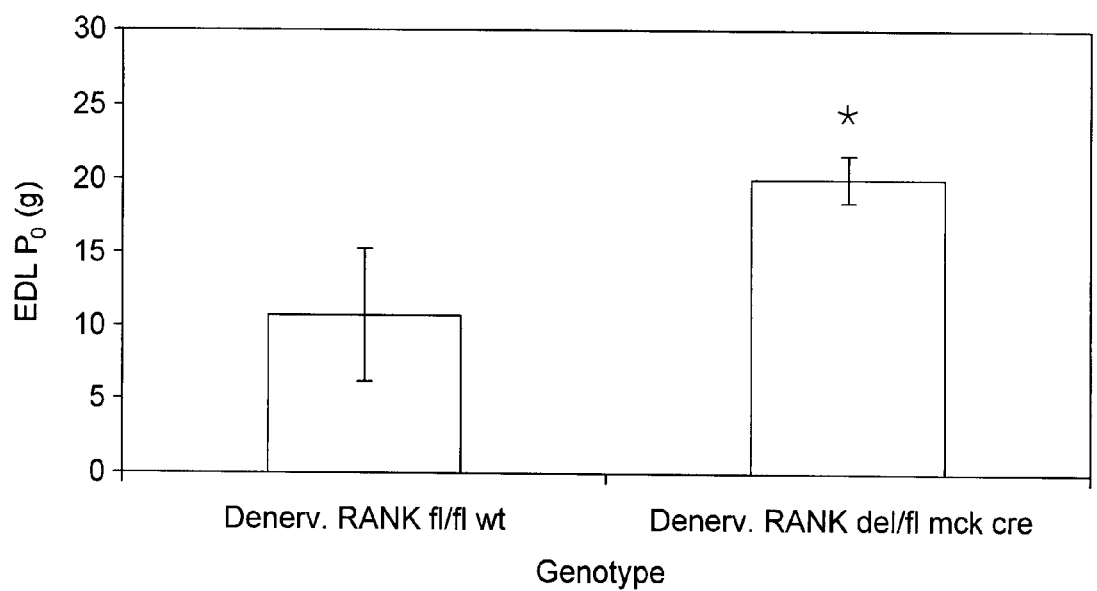
FIG. 3. RANK deletion (RANK del/fl mck cre) prevents the loss in absolute force of EDL muscles from female mice following denervation. Female mice underwent sciatic denervation and contractile properties of EDL muscles were performed at 14 d post denervation (maximum absolute tetanic tension; $P_0$ g). Sham procedure consisted of exposing the nerve without transection. Force production was twice as much in Rank ko compared to wildtype indicating that the deletion of RANK (RANK del/fl mck cre genotype) protects significantly against denervation-induced muscle disuse/ dysfunction. * Indicates a significant difference (n=2-3, P≤0.05; ANOVA and a Tukey's a posteriori test).
Figure 4:
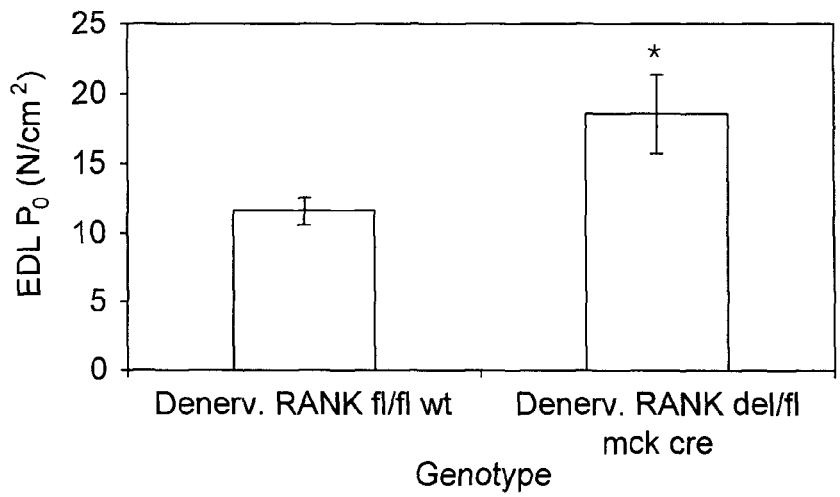
FIG. 4. RANK deletion (RANK del/fl mck cre) prevents the loss in specific force of EDL muscles from female mice following denervation. Female mice underwent sciatic denervation and contractile properties of EDL muscles were performed at 14 d post denervation (maximum specific tetanic tension; N/cm$^2$). Sham procedure consisted of exposing the nerve without transection. When muscle force is normalized by surface area, the deletion of RANK (RANK$^{del/fl}$ mck cre genotype) still protects significantly against denervation-induced muscle disuse/dysfunction * Indicates a significant difference (n=2-3, P≤0.05; ANOVA and a Tukey's a posteriori test).
Figure 5:
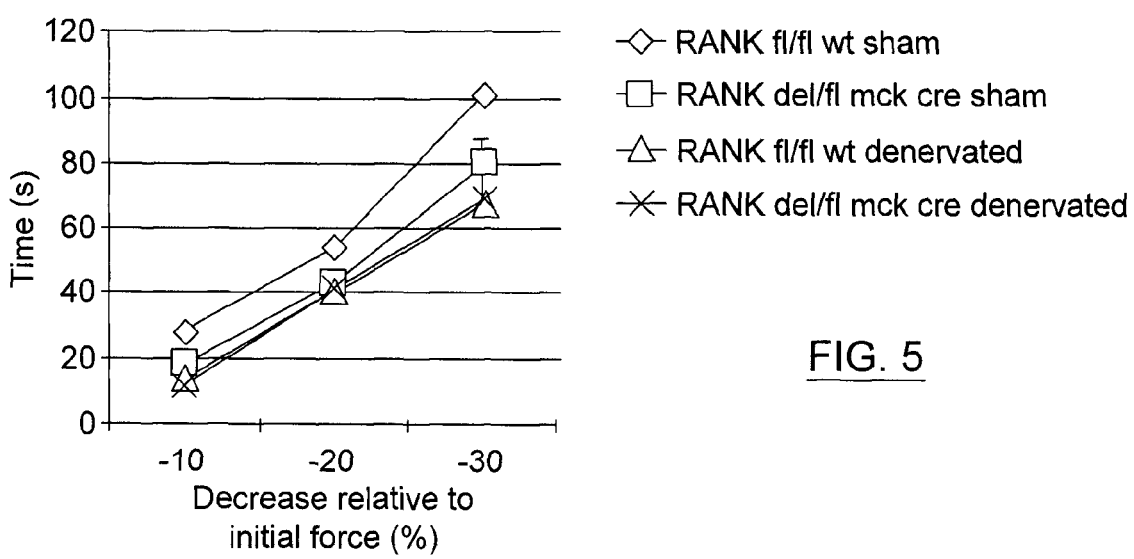
FIG. 5. The deletion of RANK muscle (RANK del/fl mck cre genotype) increases the fatigue in sham and denervated SOL muscles. To assess muscle fatigue, SOL muscles from Rank$^{fl/fl}$ and Rank$^{del/fl}$ mice were stimulated at 1 train/s at 50 Hz, and the time to the loss of 30% of their initial force was recorded. Because Rank del/fl can reprogram adult muscles from the slow-twitch phenotype into the fast twitch phenotype, it is not surprising to observe that these muscles are less resistant to fatigue than their wild type muscle counterparts, n=1.
Figure 6:
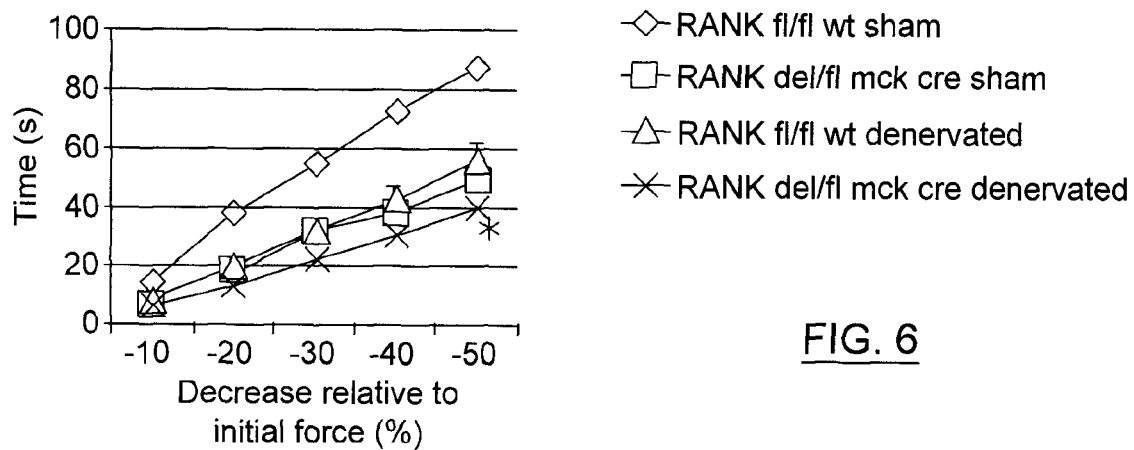
FIG. 6. The deletion of RANK muscle (RANK del/fl mck cre genotype) increases the fatigue in sham and denervated EDL muscles. To assess muscle fatigue, EDL muscles from Rank$^{fl/fl}$ and Rank$^{del/fl}$ mice were stimulated at 1 train/s at 50 Hz, and the time to the loss of 30% of their initial force was recorded. Because Rank del/fl can reprogram adult muscles from the slow-twitch phenotype into the fast twitch phenotype, it is not surprizing to observe that these muscles are less resistant to fatigue than their wild type counterparts. * Indicates a significant difference between RANK$^{fl/fl}$ denervated and RANK$^{del/fl}$ denervated (n=2, P≤0.05; Student's t-test).

Muscle contractility measurements were used to test the involvement of the RANK/RANKL pathway in muscle dysfunction. In vitro measurements of muscle contractility are the gold standard for assessing muscle function and were be performed as described previously[68,69]. SOL (predominantly slow) and EDL (predominantly fast) muscles that possess the most extreme and distinctive phenotypes in skeletal muscles were incubated in vitro in Krebs-Ringer bicarbonate buffer supplemented with glucose (2 mg/ml) and were continuously bubbled with carbogen at 25° C. Twitch and tetanic contractions were elicited, and the following measurements recorded: maximum twitch tension (Pt), time to peak tension (TPT), one-half relaxation time (RT 1/2), and maximum tetanic tension (Po). To assess muscle fatigue, EDL and SOL muscles from RANK$^{fl/fl}$ and RANK$^{del/fl}$ mice were stimulated at 1 train/s at 50 Hz, and the time to the loss of 30% of their initial force recorded. As depicted on FIGS. 2,3 and 4, the data indicate that EDL muscles from RANK$^{del/fl}$ mice are protected against denervation-induced muscle disuse. Consistent with this observation that RANK$^{del/fl}$ mice expressed a faster muscle phenotype than wild type, SOL and EDL muscles from these mice were less resistant to a fatigue protocol (FIGS. 5,6). The muscles were weighed without their tendons to quantify muscle mass and to allow the calculation of the maximum specific Po ($N/cm^2$).

TABLE 2

Table 2: Contractile and physical properties of SOL and EDL muscles following denervation.

| | SOL | | | | EDL | | | |
|---|---|---|---|---|---|---|---|---|
| | Sham fl/fl | Denerv fl/fl | Sham del/fl | Denerv del/fl | Sham fl/fl | Denerv fl/fl | Sham del/fl | Denerv del/fl |
| TPT (ms) | 55.4 ± 3.28 | 59.14 ± 3.32 | 56.29 ± 3.19 | 60 ± 3.12 | 28.6 ± 2.56 | 36 ± 2.78 | 28.33 ± 3.93 | 32.83 ± 1.35 |
| ½ RT (ms) | 49.4 ± 2.93 | 57.57 ± 3.34 * | 47.57 ± 2.94 | 63.29 ± 5.03 * | 22.6 ± 2.25 | 25.67 ± 1.65 | 20.67 ± 1.36 | 26 ± 1.79 |
| Pt (g) | 4.29 ± 0.18 | 4.19 ± 0.31 | 4.31 ± 0.39 | 4.9 ± 0.4 | 7.51 ± 0.76 | 5.56 ± 0.55 | 5.77 ± 0.83 | 6.21 ± 0.38 |
| Po (g) | 26.12 ± 0.64 | 19.56 ± 0.42 * | 25.57 ± 1.38 | 18.09 ± 0.99 * | 33.08 ± 1.63 | 21.31 ± 1.4 * | 33.5 ± 1.31 | 22.1 ± 1.42 * |
| CSA (μm2) | 1172 | 807 ± 99 | 1467 | 752 ± 69 | 984 | 651 ± 80 | 1254 | 641 ± 71 |
| Muscle weight (mg) | 7.74 ± 0.25 | 6.40 ± 0.41 | 8.39 ± 0.60 | 6.44 ± 0.34 | 8.98 ± 0.43 | 7.86 ± 0.40 | 9.40 ± 0.66 | 6.84 ± 0.40 |

Sham and denervated RANK$^{fl/fl}$ and RANK$^{del/fl}$ SOL and EDL muscles were incubated ex vivo and electrically stimulated (1, 10, 50, 100 Hz at 35 V) to measure time to peak tension (TPT), half relaxation time (½ RT), maximal twitch tension (Pt) and maximal absolute force (Po). Muscle weight and mean fiber CSA was determined thereafter. Data are presented as mean +/− sem.
* significantly different from sham RANK$^{fl/fl}$,
significantly different from denervated RANK$^{fl/fl}$, p < 0.05 (ANOVA with a post-hoc Tukey test).

Protein Concentrations and Western Blotting

To determine how Rank influences muscle function, the present inventor(s) have studied proteins involved in muscle degradation, contraction, relaxation, and regulation. It is important to mention that all of these functions require $Ca^{2+}$. The present inventor(s) have first investigated by Western blotting the concentrations of SERCA2a, CaMKII and fast myosin heavy chain following denervation in RANK$^{fl/fl}$ and RANK$^{del/fl}$ mice. To do so, 50 μg of SOL and EDL muscle extract were separated on 6, 10, or 12% SDS-PAGE gels. The separated proteins were transferred to PVDF membranes (Bio-Rad) and incubated with primary antibodies directed against SERCA, CaMK and fast myosin heavy chain. Because band intensities for GAPDH or α-tubulin vary in sham and denervated muscles, the present inventor(s) normalized with the absolute quantification of proteins and expressed in arbitrary units where sham SOL or EDL muscles from Rank$^{fl/fl}$ mice equal 1. Western blotting data showed that the concentrations of SERCA2a and fast MyHC increased while the concentration of CaMKII, which may promote slow-twitch phenotype, decreased in EDL muscles from RANK$^{del/fl}$ mice (FIGS. 7,8).

SERCA Activity in Rank-Deficient Skeletal Muscles

SERCA activity were investigated in denervated EDL muscles in which significant changes in contractile properties (TPT, 1/2RT, Pt, Po) are observed. To assess SERCA activity sham and experimental SOL and EDL muscles were dissected, frozen in liquid nitrogen, and stored at −80° C. until processed. Frozen EDL and SOL muscles were homogenized in 5 volumes of 10 mM Tris/HCl (pH 8.4) supplemented with 0.3 M sucrose. SERCA activity were measured by following the oxidation of NADH at 340 nm in assay buffer containing 1 mM EGTA (pH 7.5), 10 mM phosphoenolpyruvate, 18 U/mL of pyruvate kinase and lactate dehydrogenase, 0.2 mM NADH, 20 mM Hepes, 200 mM KCl, 15 mM $MgCl_2$, 10 nM $NaN_3$, and 0.005% Triton X-100. The reaction started by the addition of 4 mM MgATP. $CaCl_2$ (0.5-0.8 mM) (low $Ca^{2+}$ concentration) were added and the slope recorded. The $CaCl_2$ concentration were then increased to 20 mM (high $Ca^{2+}$ concentration), and the slope were recorded again. SERCA activity were expressed as the difference between the activity of the low and high $Ca^{2+}$ recordings[70].

Findings:

The RANK/RANKL/OPG triad is essential for bone remodelling. An increase in the RankL/OPG ratio leads to osteoporosis. Contractile property measurements and SERCA activity and Western blot analyses of protein involvement in $Ca^{2+}$ mobilization indicate that RANK deletion influences muscle function following denervation (see FIGS. 2,3,4 and 7). It was interesting to note that EDL muscles are mainly composed of fast twitch myofibres (IIa, IIb and IIx) and that these myofibres are significantly affected by myopathies, aging, sepsis, etc[71,72].

$Ca^{2+}$ and Cell Signaling

Figure 17A:
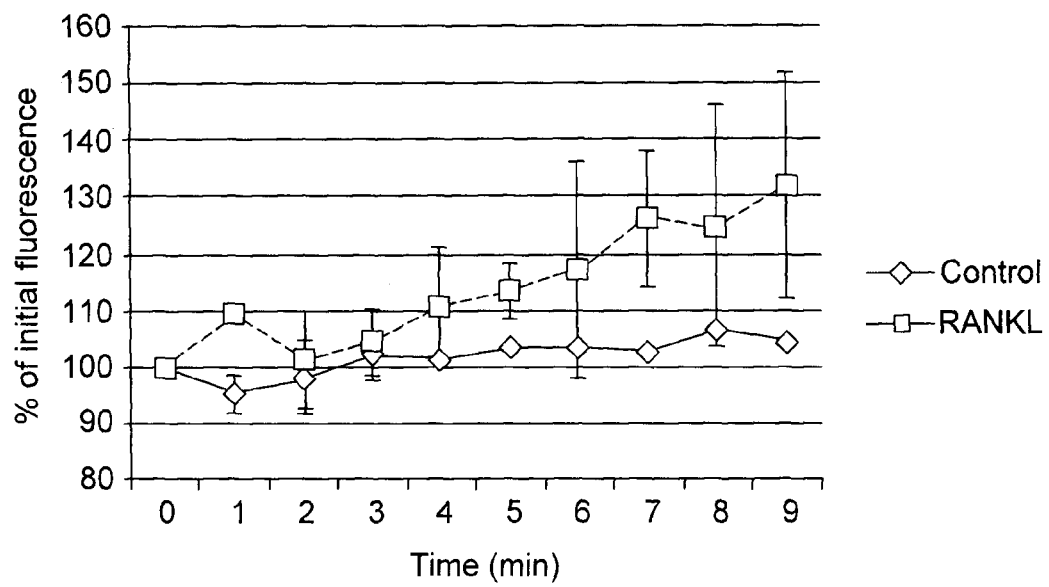
Figure 17B:
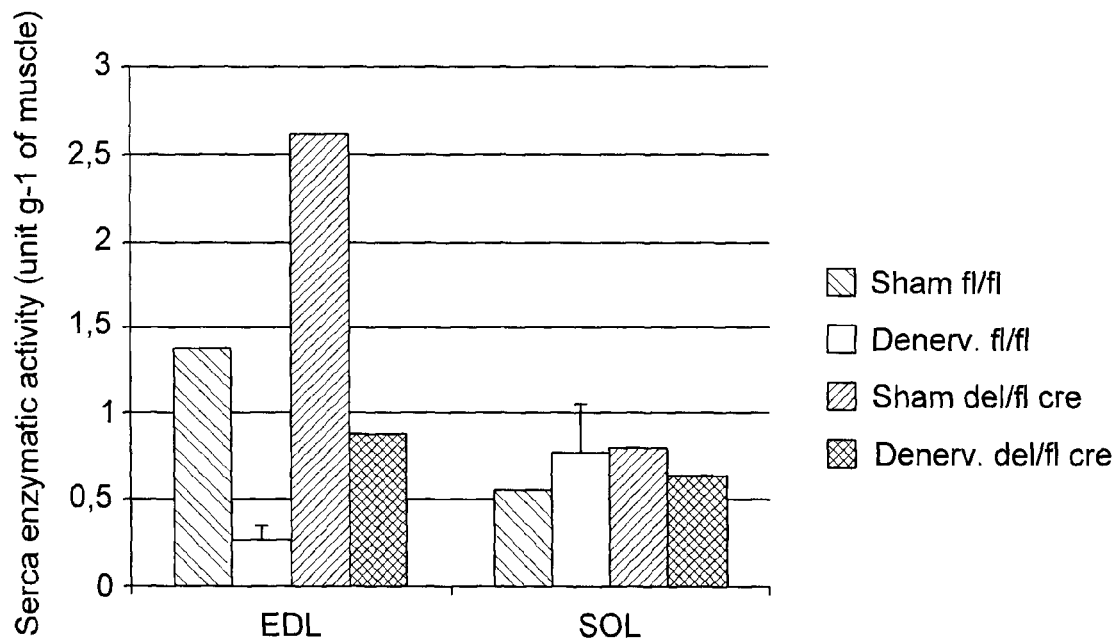
Figure 17E:
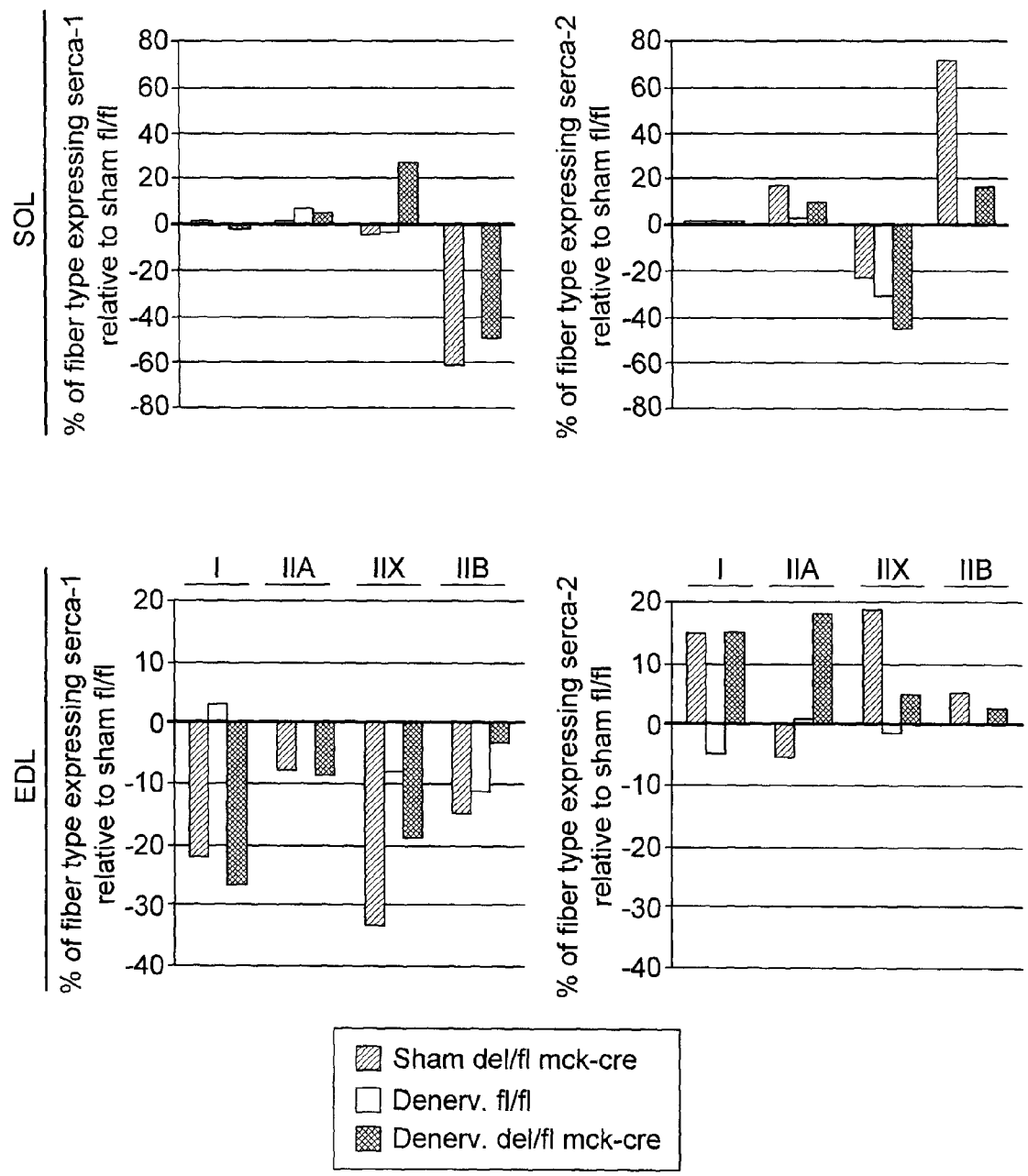
Figure 17F:
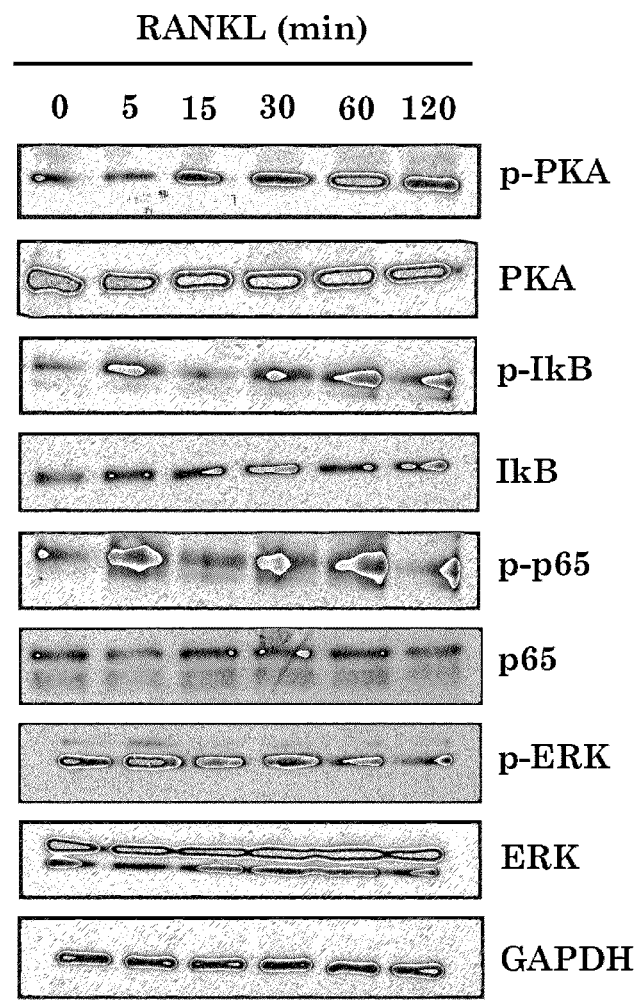
Figure 17G:
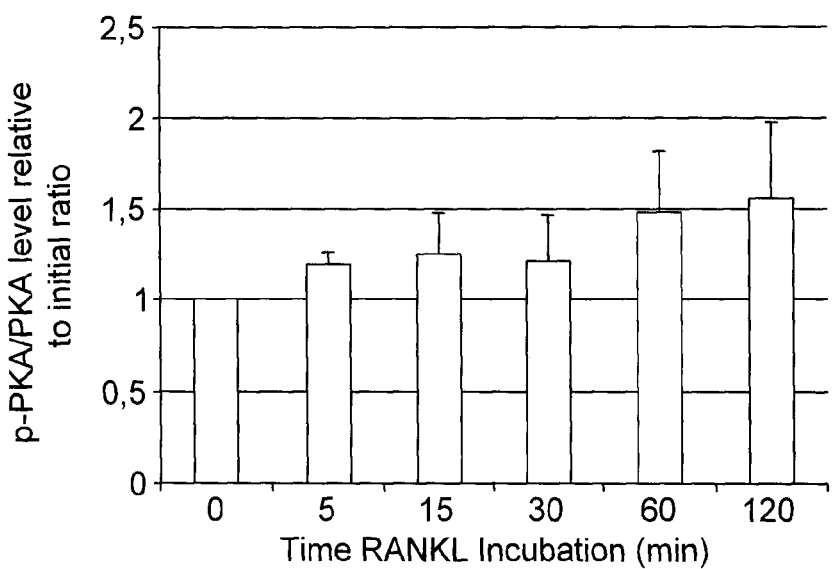
Figure 17H:
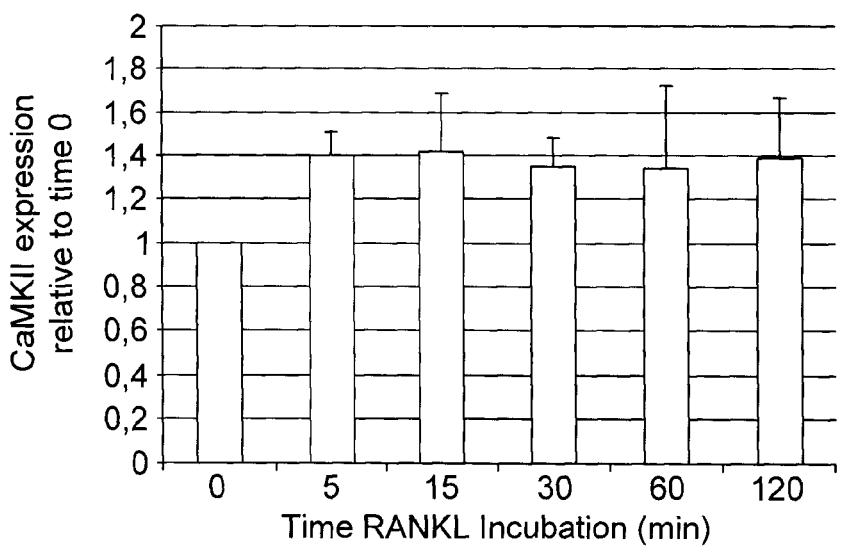
Figure 17I:
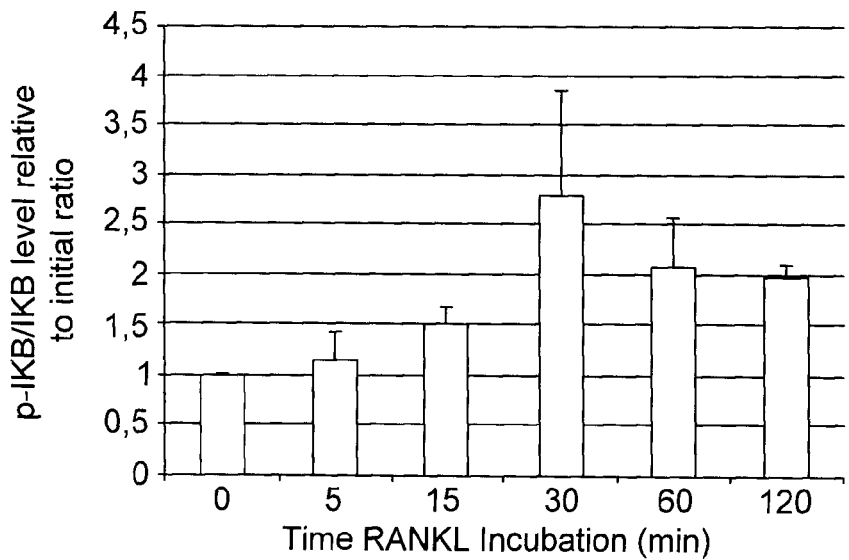
Figure 17J:
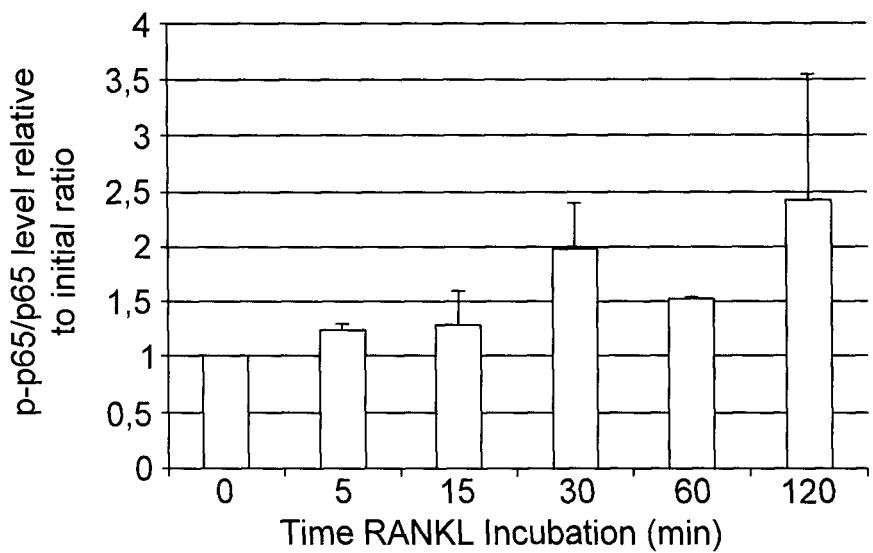
Figure 17K:
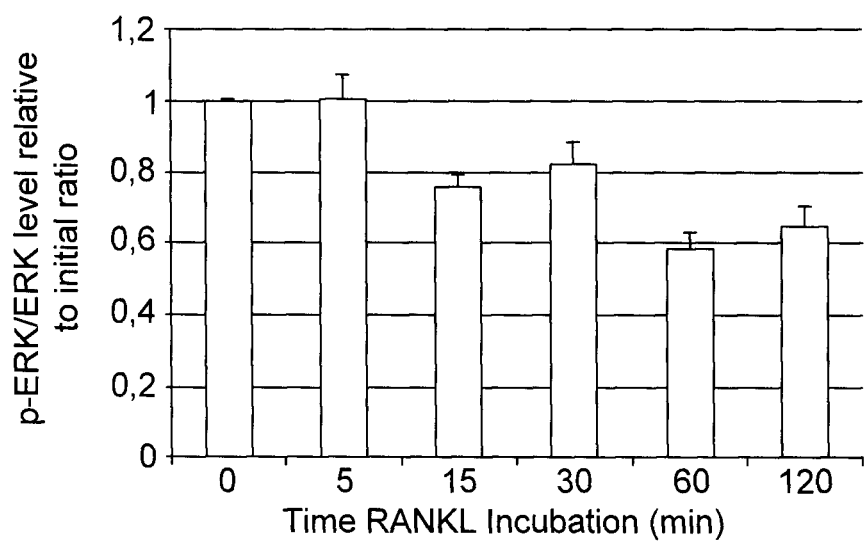

C2C12 myotubes fully differentiated were incubated with fluo-4 to measure $Ca^{2+}$ concentration. C2C12 Myotubes were then exposed to RANKL (100 ng/ml) for 10 min. The addition of RANKL increased the release of cytosolic $Ca^{2+}$ in myotubes. (FIG. 17A). Serca activity in sham and denervated RANK$^{del/fl}$ compared to sham and denervated RANK$^{fl/fl}$ EDL muscles were then measured by spectrofluorimetric analysis. SERCA activity increased by more than 2-fold in EDL muscles from sham and denervated RANK$^{del/fl}$ mice (FIG. 17B). SOL and EDL muscle were sectioned and immunolabeled with the MyHC isoforms (green) and SERCA isoforms (red) which demonstrated that RANK$^{del/fl}$ MyHC type IIB fibers express SERCA-1 and SERCA-2 (yellow) whereas RANK$^{fl/fl}$ MyHC IIB fibers were rigourously limited to SERCA-1 in SOL muscles (FIGS. 17C and D). Graph representing the difference in the expression of SERCA isoforms for each fiber type for SOL and EDL muscles compared to sham RANK$^{fl/fl}$ mice. (FIG. 17E). In another set of experiment, myotubes were stimulated with RANKL (100 ng/ml) and muscle cell extracts were loaded on SDS-PAGE, transferred on membrane and immunolabeled for PKA, IKB, p65, ERK1/2 and their phosphorylated form and CaMKII expression at different time points. * significantly different from RANK$^{fl/fl}$, # significantly different from denervated RANK$^{fl/fl}$, p<0.05 (ANOVA with a post-hoc Tukey test). Data are presented as mean+/−sem.

Protein Concentrations and Western Blotting

Figure 18A:
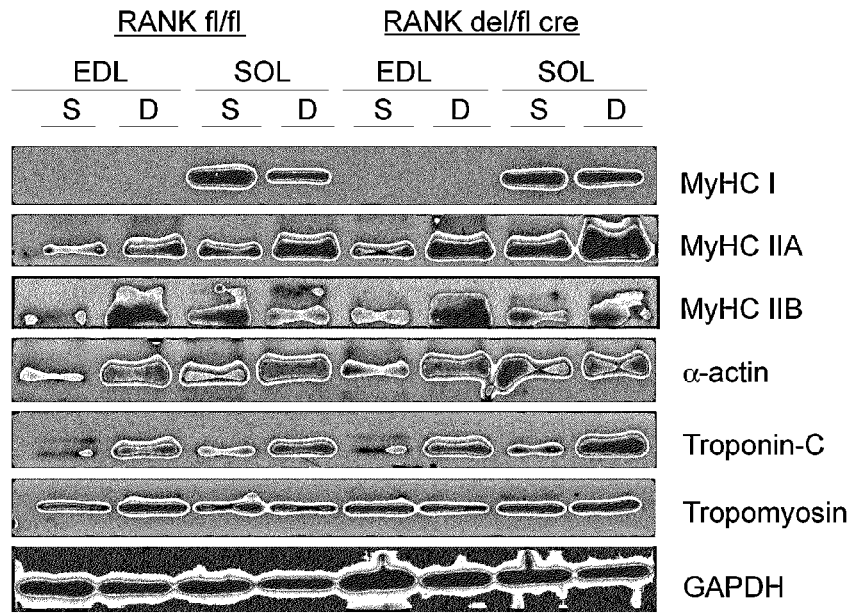
Figure 18B:
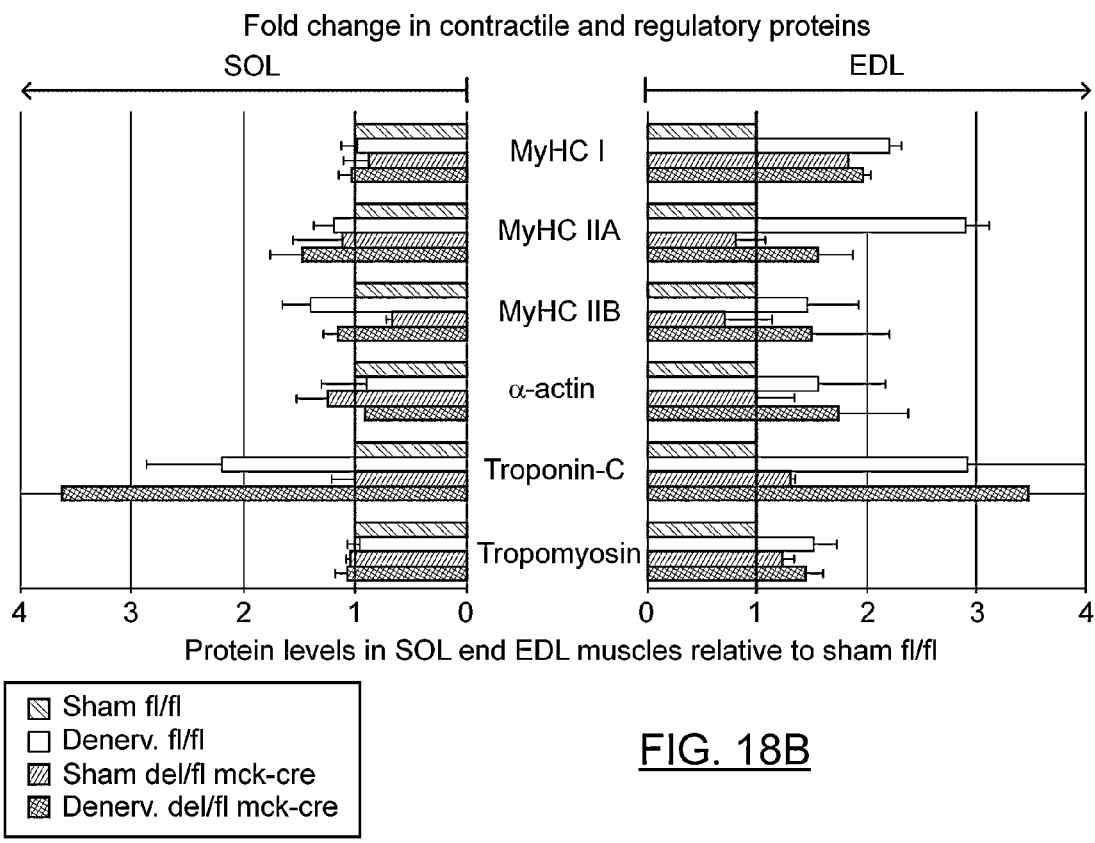
Figure 18C:
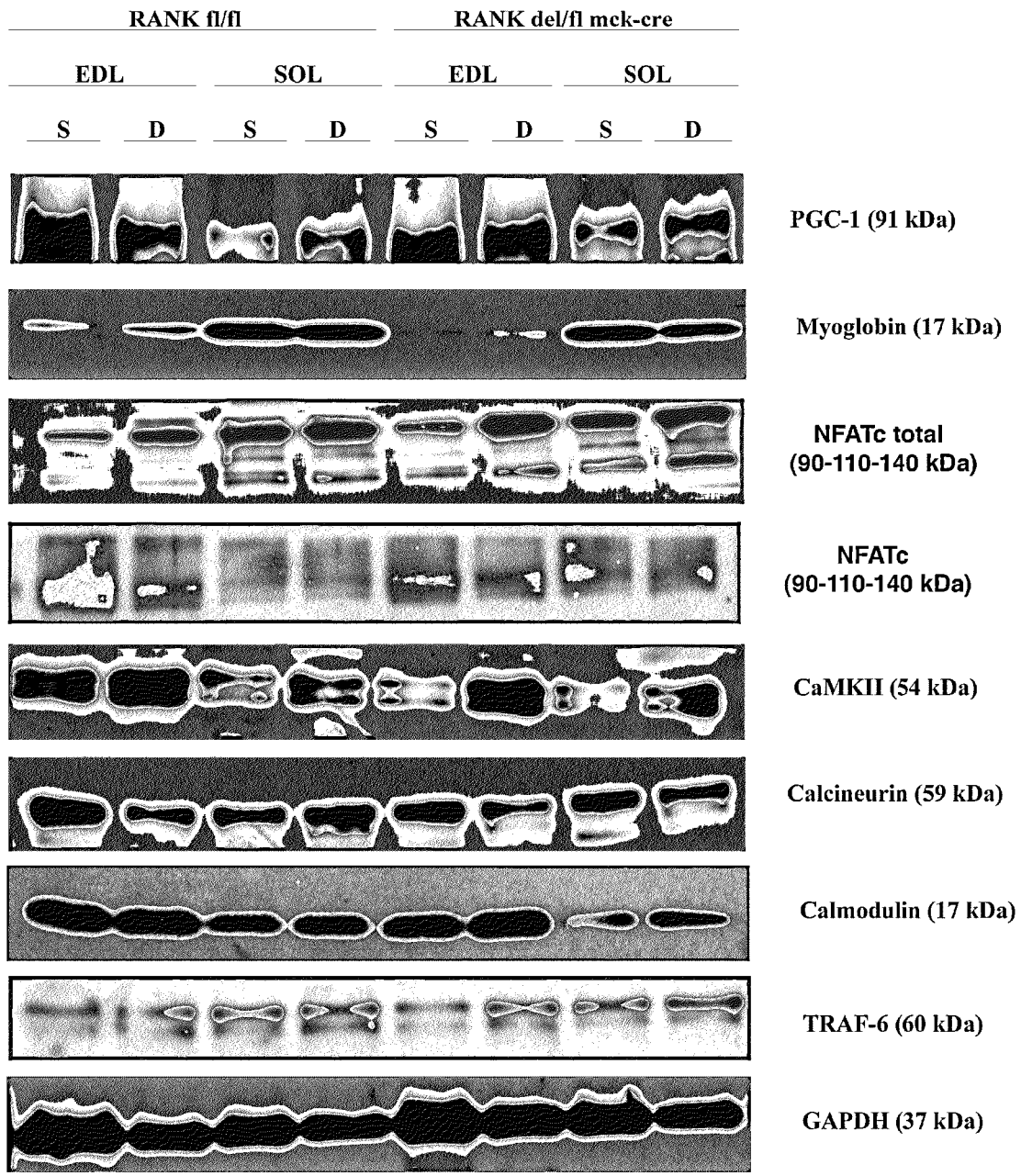
Figure 18D:
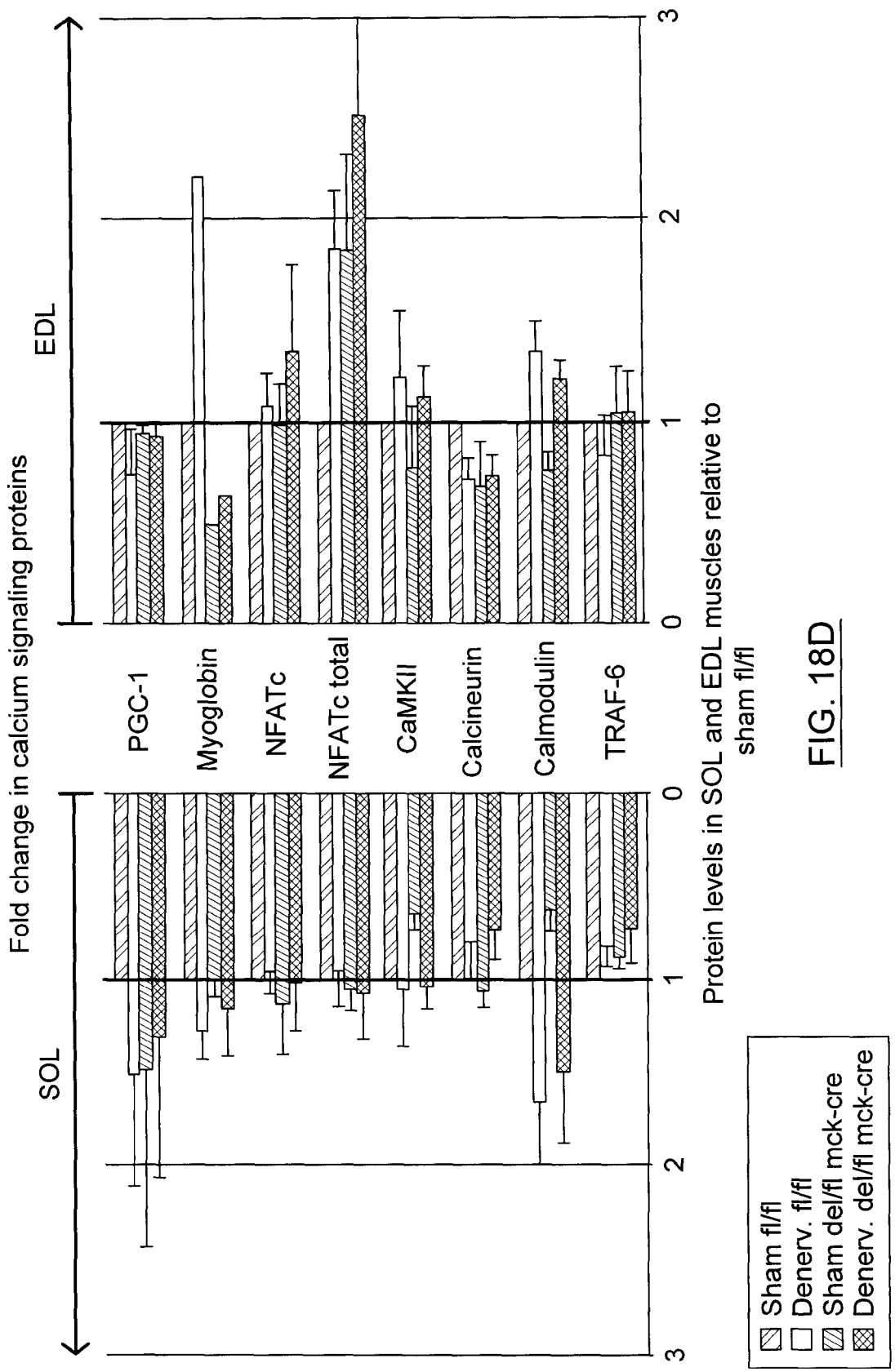
Figure 18E:
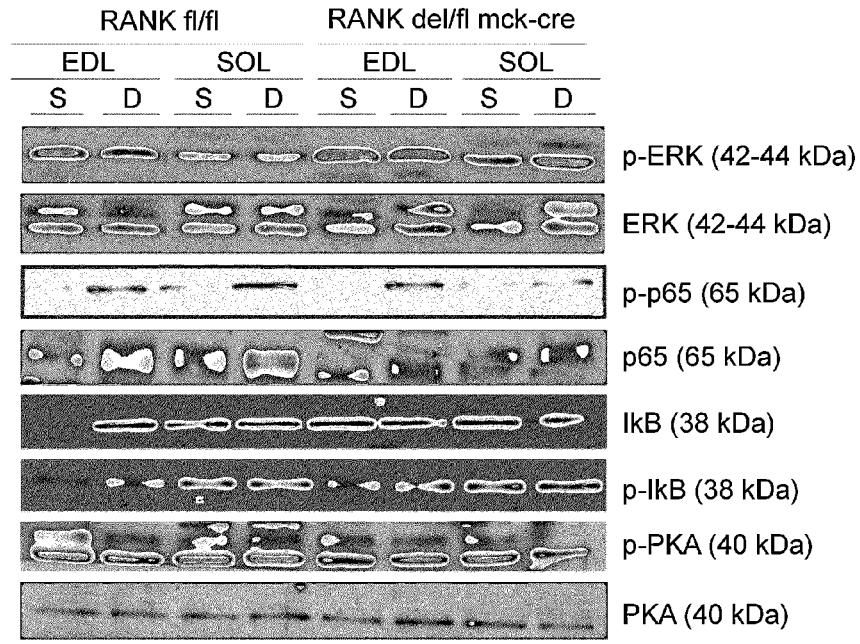
Figure 18F:
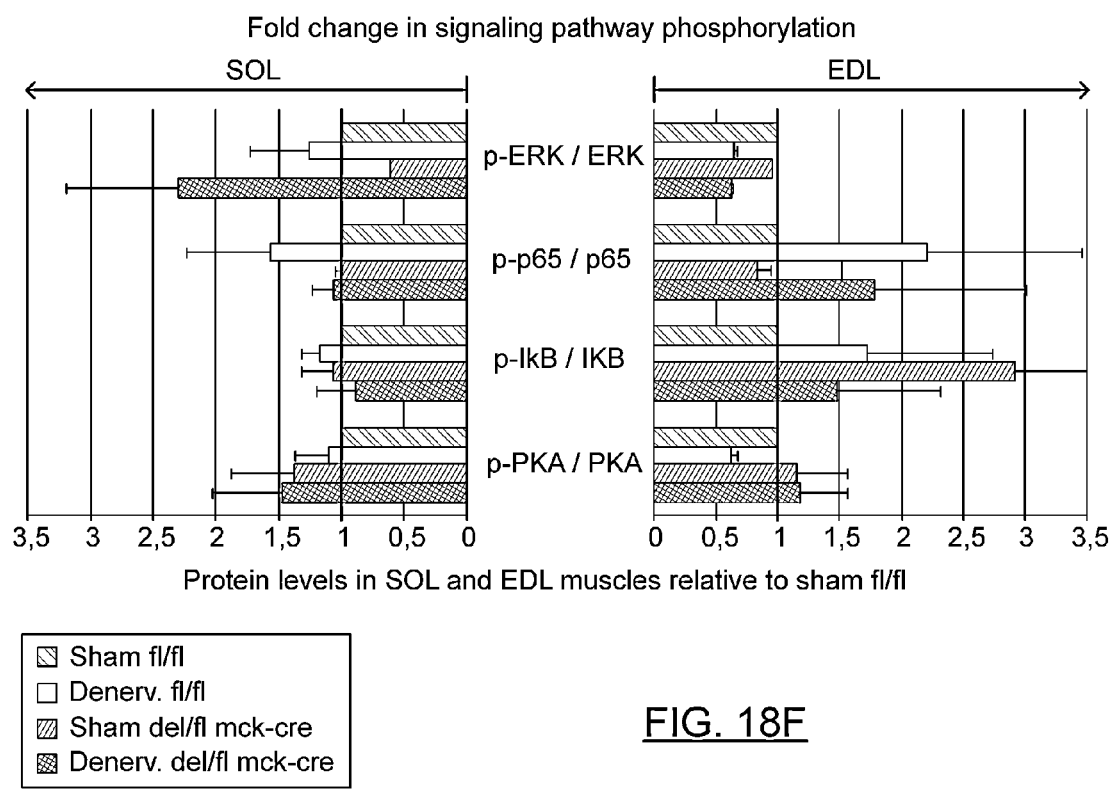
Figure 18G:
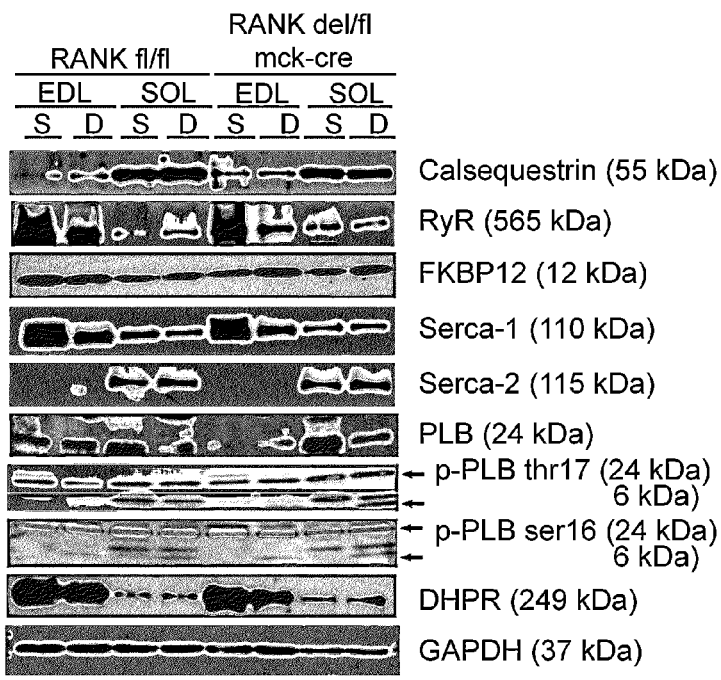
Figure 18H:
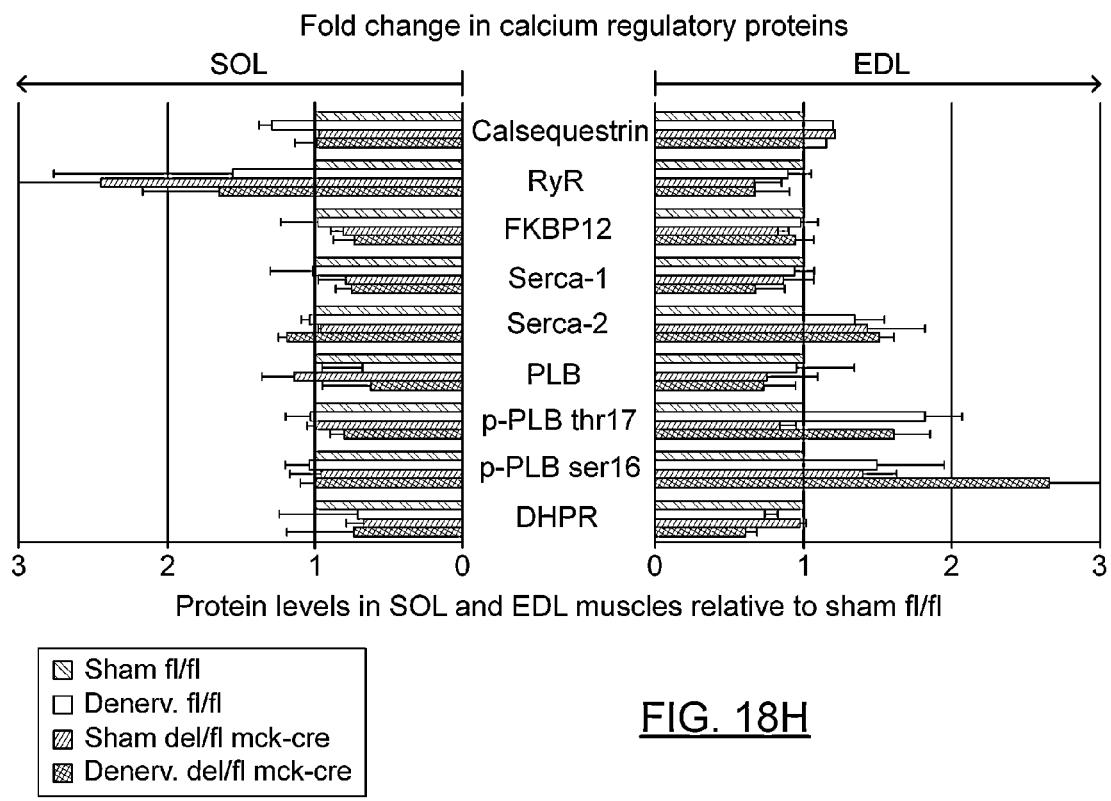
Figure 18I:
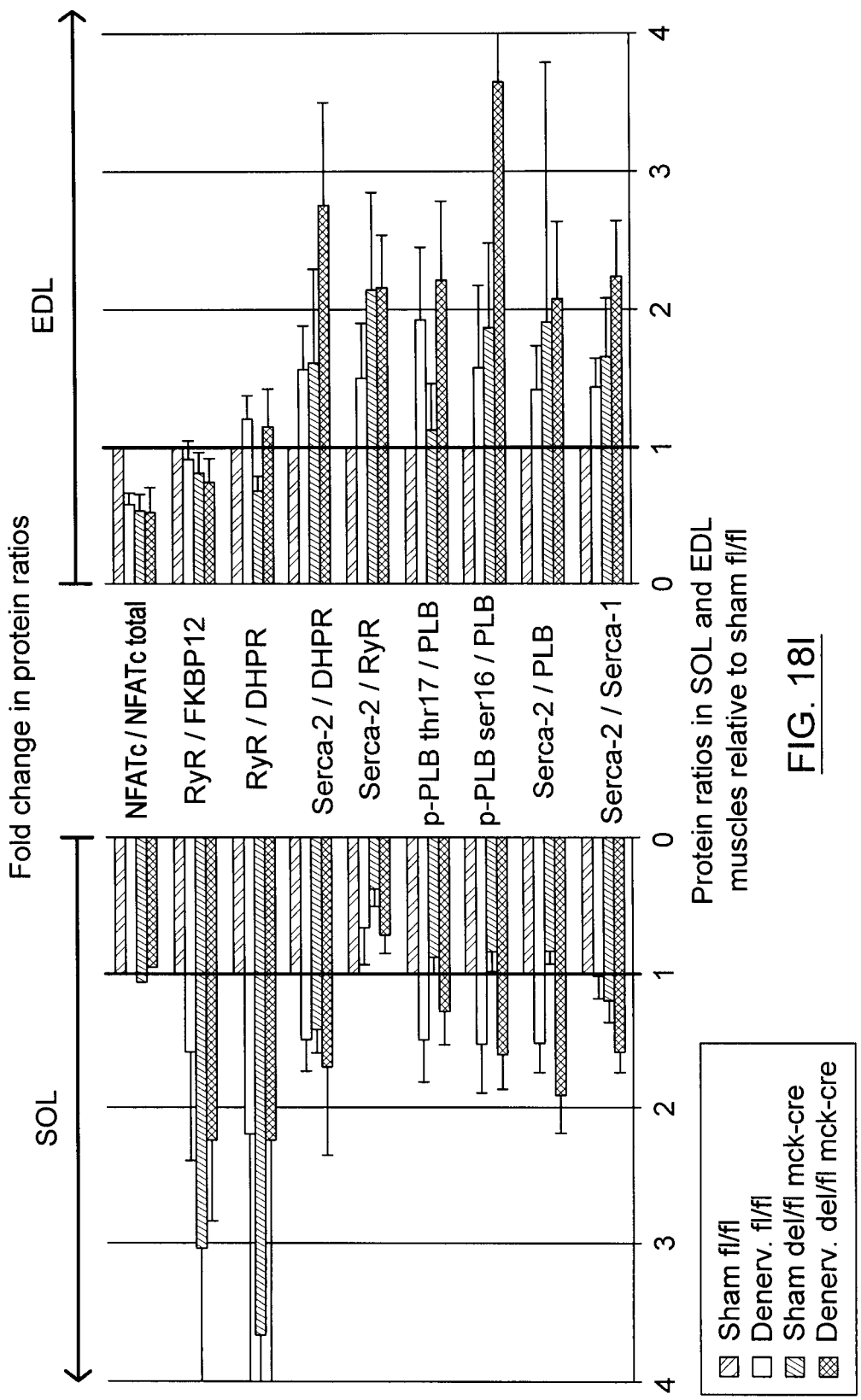

To determine how RANK influences muscle function, the present inventor(s) have studied proteins involved in muscle degradation, contraction, relaxation, and regulation. It is important to mention that all of these functions require $Ca^{2+}$. The present inventor(s) have first investigated by Western blotting the concentrations of MyHC I, MyHC IIA, MyHC IIB, α-actin, troponin C, PGC-1α, myoglobin, NFATc, CaMK, calcineurin, TRAF6, calsequestrin, RYR, FKB12, SERCA1, SERCA2, phospholamban, DHPR, ERK, P65, IkB, PKA following denervation in RANK$^{fl/fl}$ and RANK$^{del/fl}$ mice. To do so, 50 μg of SOL and EDL muscle extracts were separated on 6, 10, or 12% SDS-PAGE gels. The separated proteins were transferred to PVDF membranes (Bio-Rad) and incubated with various primary antibodies. Because band intensities for GAPDH or α-tubulin vary in sham and denervated muscles, the present inventor(s) normalized with the absolute quantification of proteins and expressed as fold increase or decrease relative to sham RANK$^{fl/fl}$ muscles. Representative images of immunoblots and mean fold change in contractile and regulatory protein expression in sham and denervated SOL (left) and EDL (right) muscles from RANK$^{fl/fl}$ and RANK$^{del/fl}$ mice (FIGS. 18A, 18B). Results indicate more important changes in protein expression in EDL than SOL muscles (FIG. 17B). Representative images of immunoblots and mean fold change in Ca$^{2+}$ signaling protein expression in sham and denervated SOL (left) and EDL (right) muscles from RANK$^{fl/fl}$ and RANK$^{del/fl}$ mice were then measured by spectrofluorimetric analysis (FIGS. 18C, 18D). Results indicate an activation of the NF-kB pathway following the denervation (FIGS. 18E, 18F) Data showed a decrease in Ca$^{2+}$ signaling pathways in sham RANK$^{del/fl}$ EDL muscle (FIGS. 18G, 18H). Representative images of immunoblots and mean fold change in the phosphorylation ratio of different signaling pathways in sham and denervated SOL (left) and EDL (right) muscles from RANK$^{fl/fl}$ and RANK$^{del/fl}$ mice (FIGS. 18E, 18F). Representative images of immunoblots and mean fold change in Ca$^{2+}$ regulatory protein expression in sham and denervated SOL (left) and EDL (right) muscles from RANK$^{fl/fl}$ and RANK$^{del/fl}$ mice (FIG. 18H). Graphic representing the mean fold change in Ca$^{2+}$ protein ratios in sham and denervated SOL (left) and EDL (right) muscles from RANK$^{fl/fl}$ and RANK$^{del/fl}$ mice. The present findings showed a decrease in Ca$^{2+}$ channel proteins that control the rise in [Ca$^{2+}$]$_i$ (RyR, DHPR) and an increase in Ca$^{2+}$ proteins that favour Ca$^{2+}$ reuptake (SERCA-2, p-PLB) in RANK$^{del/fl}$ EDL muscles. One interesting finding is the phosphorylation of p-PLB on serine16. This phosphorylation serine 16 by PKA disinhibits and improves SERCA function (FIG. 18I) Lastly, our results demonstrated an increase in protein ratios that favours Ca$^{2+}$ captation (SERCA-2/PLB, p-PLB/PLB, SERCA-2/DHPR, SERCA-2/RyR) and a switch from SERCA-1 to SERCA-2 isoform in RANK$^{del/fl}$ EDL muscles. Data are presented as mean+/−sem * significantly different from sham RANK$^{fl/fl}$, # significantly different from denervated RANK$^{fl/fl}$, $p<0.05$ (ANOVA with a post-hoc Tukey test).

Morphological, Functional, Histological and Chemical Analyses in Rank-Deficient Skeletal Muscles Contractile properties, fiber typing and SERCA activity were investigated in our models of hindlimb unloading and reloading, denervation and dystrophy. Contractile properties were quantified as described before and fiber typing were performed by immunolabeling cross sectional muscle with antibodies directed against MyHC type I, IIa, IIb, IIx. To assess SERCA activity sham and experimental SOL and EDL muscles were dissected, frozen in liquid nitrogen, and stored at −80° C. until processed. Frozen EDL and SOL muscles were homogenized in 5 volumes of 10 mM Tris/HCl (pH 8.4) supplemented with 0.3 M sucrose. SERCA activity were measured by following the oxidation of NADH at 340 nm in assay buffer containing 1 mM EGTA (pH 7.5), 10 mM phosphoenolpyruvate, 18 U/mL of pyruvate kinase and lactate dehydrogenase, 0.2 mM NADH, 20 mM Hepes, 200 mM KCl, 15 mM MgCl$_2$, 10 nM NaN$_3$, and 0.005% Triton X-100. The reaction started by the addition of 4 mM MgATP. CaCl$_2$ (0.5-0.8 mM) (low Ca$^{2+}$ concentration) were added and the slope recorded. The CaCl$_2$ concentration were then increased to 20 mM (high Ca$^{2+}$ concentration), and the slope were recorded again. SERCA activity were expressed as the difference between the activity of the low and high Ca$^{2+}$ recordings[70].

Findings:

Together, these results indicate that the activation of RANK/RANKL increase [Ca$^{2+}$]$_i$ in muscle cells, while the depletion of RANK favors the activity of SERCA and the mobilization and sequestration of Ca$^{2+}$ in the sarcoplasmic reticulum. Low resting cytoplasmic Ca$^{2+}$ is associated with a better muscle contraction and a fast-twitch fiber phenotype, all of which are deficient in muscle wasting conditions and pathologies such as cancer cachexia, muscular dystrophy, aging and other muscle diseases.

Example 3: Evaluation of the Involvement of the RANK/RANKL/OPG Pathway in Muscle Cell Atrophy Induced by Dexamethasone In Vitro and In Vivo Rationale:

Oral or inhaled glucocorticoids such as dexamethasone (DEX) are frequently used to suppress several types of allergic, inflammatory, and autoimmune disorders. Inhaled glucocorticoids are the second-line treatment for asthma. They are also administered to treat sepsis, cancer, acute transplant rejection, myopathies such as Duchenne muscular dystrophy, critical illness myopathy, and many other inflammatory and autoimmune diseases. However, if DEX is prescribed for more than a few days, side-effects common to systemic glucocorticoids may occur. One of the most noticeable side-effects of chronic DEX administration is a negative protein balance (catabolism) that eventually leads to muscle atrophy. This type of muscle atrophy/dysfunction is largely caused by the accelerated breakdown of muscle proteins via the ubiquitin-proteasome pathway, namely MAFbx/atrogin-1 and MuRF1. Deletion of the MuRF1 gene prevents DEX-induced degradation of myofibres[73]. In addition, DEX induces a reduction in Akt activity, preventing the inactivation of atrophic FOXO transcription factors. Interestingly, insulin growth factor-1 (IGF-1) antagonizes the catabolic action of DEX through the PI3-kinase/Akt/mTor pathway by inhibiting the activity of FOXO[74]. In bone, IGF-1, insulin, and insulin receptor substrates (IRS-1 and -2) are essential anabolic regulators of bone metabolism. In addition, RANKL expression is not induced by IGF-1 and vitamin D in osteoblasts deficient in IRS-1, which causes osteopenia with low bone turnover[75,76]. Consistent with this observation, patients with laron syndrome caused by IGF-1 deficiency or patients with insulin-dependent diabetes mellitus lose bone rapidly, while the loss is offset by IGF-1 and insulin replacement[77,78]. Preliminary results showed that 1 mM DEX induced myotube atrophy and favoured the expression of MyHC type I and IIa and that the addition of >100 ng/ml of OPG reversed the atrophic and phenotype change process in myotubes.

Experimental Design:

In Vitro Study

To further investigate how RANK/RANKL influences muscle function, the present inventor(s) have assessed the effect of DEX on C2C12 myoblasts grown in DMEM containing 10% FBS and 1% antibiotic-antimycotic in 96-well plates at a density of 3,000 myoblasts/well. The present inventor(s) used this mouse myoblast cell line because the present inventor(s) are very familiar with it and because it easily differentiates into myotubes and responds to RANKL stimulation. Confluent myoblasts on coverslips (approximately 300,000/well) were incubated in DMEM containing 2% horse serum for five days to allow them to differentiate into myotubes. The myotubes were then exposed to 1 mM DEX. This concentration was sufficient to induce a 15-20% decrease in myotube diameter relative to control myotubes after 48 h. Myotubes in other wells were treated or not with 1 mM DEX combined with 100 ng/ml of OPG. In the experiment proposed herein, myotube atrophy were determined by measuring the diameters of the myotubes at 100× magnification using a light microscope (Nikon). Three different sites in each well were blindly identified and observed throughout the experiment. The average were considered as a single value. Myotube diameters were quantified using the ImageJ digital imaging system (NIH). The diameters of 150 to 200 myotubes per well were measured after 24 and 48 h. Measurements were performed in triplicate for all the experimental conditions to enable statistical comparisons between groups.

In Vivo Study

To study the role of the RANK/RANKL/OPG pathway in DEX-induced muscle atrophy/dysfunction, Rank$^{fl/fl}$ experimental RANK$^{del/fl}$ mice were injected i.p. once a day for 7 consecutive days with 1 mg/kg of DEX. The mice were sacrificed on day 7 post-DEX treatment. The EDL and SOL muscles were dissected to measure SERCA activity as described in exemple#2.

Figure 9:
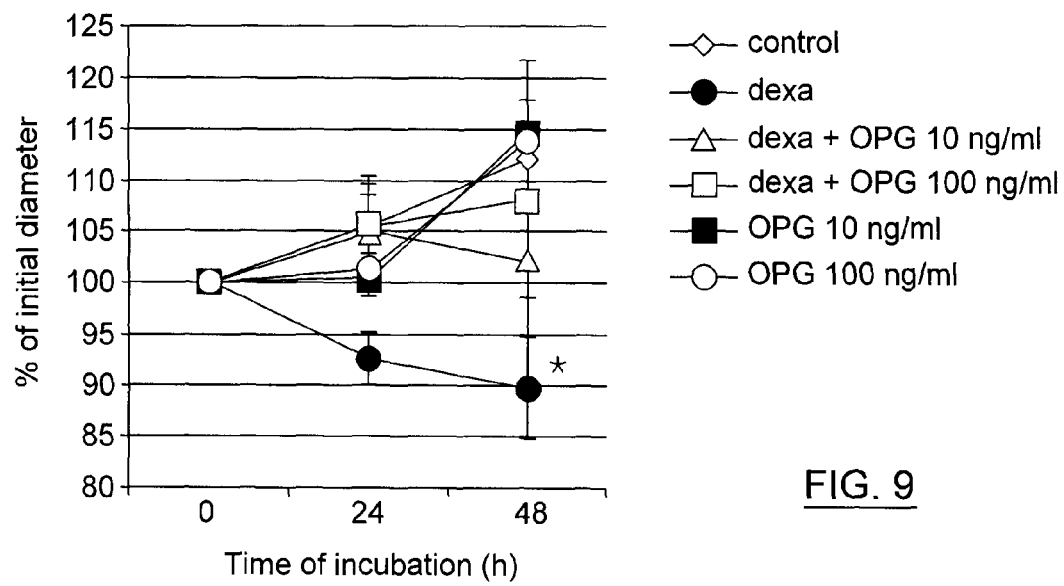
FIG. 9. Osteoprotegerin prevents dexamethasone-induced myotube atrophy. Myotubes were incubated with DEX (1,000 nM) and/or OPG at 10 ng/mL or 100 ng/mL. OPG used and tested in vivo and in vitro was bought from R&D systems (Catalog number:459-MO). The presence of DEX induced a significant diminution in myotube diameter (myotube atrophy) after 24 and 48 h of incubation while the addition of OPG (100 ng/ml) totally reversed the atrophic process at both time points (n=3, P≤0.05; ANOVA and a Tukey's a posteriori test).
Figure 10:
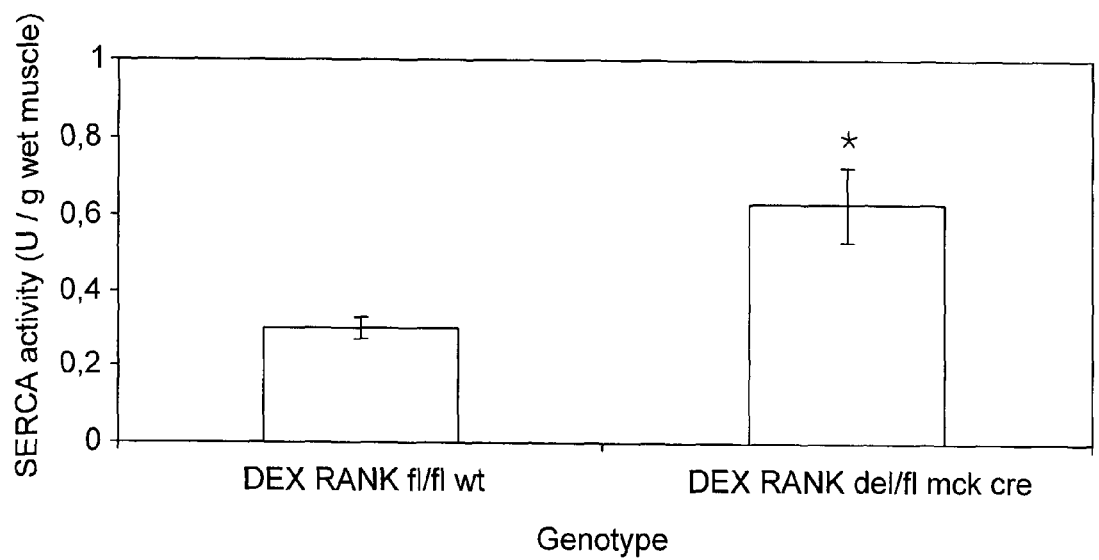
FIG. 10. The deletion of RANK (RANK del/fl mck cre genotype) increases sarcoplasmic Ca2+-ATPase (SERCA) activity. Male mice were treated during 7 days with dexamethasone (1 mg/kg) and EDL muscles were dissected and homogenized for measurement of SERCA activity. SERCA activity is increased by 2 fold in RANK ko relative to wild type mice. * Indicates a significant difference (n=2-3, P≤0.05; Student's t-test).

Findings:

Results showed that OPG protects against DEX-induced myotube atrophy in vitro (FIG. 9). In vivo results indicate that the deletion of RANK in skeletal muscle preserves muscle function and doubles SERCA activity 7 d post DEX injections (FIG. 10).

Example 4: Rank Deletion Improves Muscle Function in Critically Ill Myopathic Mice Rationale:

Myopathy and polyneuropathy occur in critically ill patients during ICU stays, causing generalized muscle weakness, failure of weaning, and prolonged rehabilitation[79]. This form of myopathy can affect up to 80% of patients with prolonged ventilator support secondary to diaphragm weakness[80]. Prolonged bed rest also increases the risk of secondary complications such as pneumonia, deep vein thrombosis, and pulmonary embolisms. Sepsis and the resulting systemic inflammation initiate the myopathic process during ICU hospitalization. However, several other ICU interventions may make a bad condition even worse[81]. For example, septic and non-septic patients may require mechanical ventilation (diaphragm unloading), daily injections of DEX (increases muscle catabolism; example #3 DEX project), and neuromuscular blocking and paralysing agents for tracheal intubations or suctions (muscle inactivity increases catabolism; example #1: denervation project). Little is known about the physiopathology of critical illness myopathies. However, the results of exposing skinned muscle fibres to sera from patients with critical illness myopathy show that muscle membrane excitability and related SR $Ca^{2+}$ release are affected[82]. The present inventor(s) believe that blocking RANK, which modulates $Ca^{2+}$ mobilization through SERCA, should preserve muscle integrity and function and reduce the duration of mechanical ventilation and hospitalization of ICU patients.

Experimental Design:

Mouse Model of Critical Illness Myopathy

While rodent models of critical illness myopathy did not involve intubation or long periods of critical illness, the pathologic and neurophysiologic changes in rodent muscles were identical to those observed in critical illness myopathy hospital patients[85]. The proposed model were still the most relevant and reliable for investigating the mechanisms underlying muscle atrophy in critically ill patients. The rodent model of critical illness myopathy usually combined a corticosteroid treatment and sciatic denervation. The denervation mimicks the use of neuromuscular blocking and paralyzing agents. Sciatic denervation and daily DEX injections were performed as described for examples 2 and 3. Since DEX and denervation are both potent inducers of muscle atrophy, seven days is sufficient to induce major skeletal muscle atrophy, especially of fast-twitch fibres (type IIb).

Contractile Property Measurements

Following the experimental procedures, the SOL and EDL muscles from experimental RANK$^{fl/fl}$ and RANK$^{del/fl}$ mice were sacrificed on day 7 post-surgery and the contractile properties measurements analyzed as described in example #2

Figure 11:
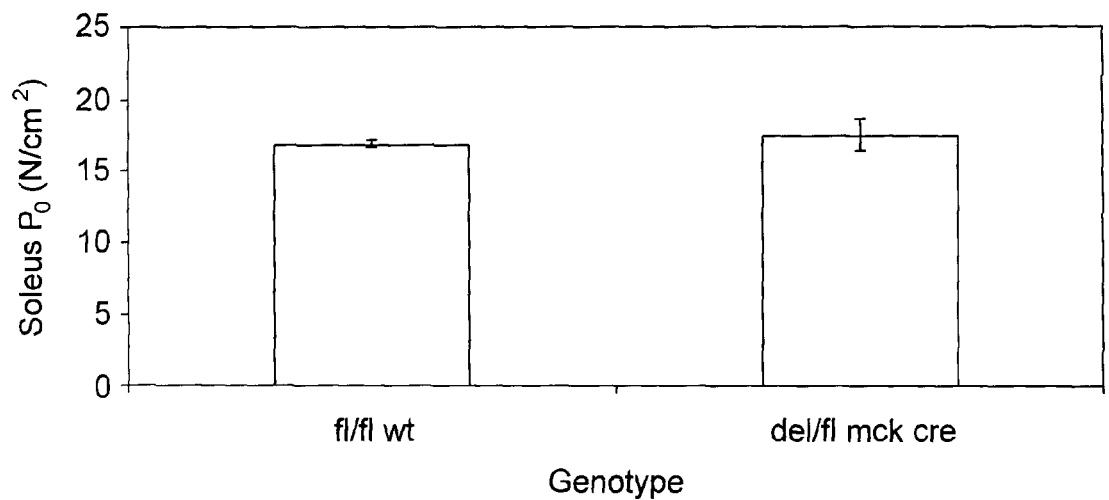
FIG. 11. RANK deletion (RANK del/fl mck cre) does not reduce the loss in specific force of SOL muscles in a model of critical illness myopathy. In a model of critical illness myopathy, male mice underwent sciatic denervation and dexamethasone treatment (1 mg/kg). SOL muscles were dissected and contractile properties recorded at 7 days post treatment (n=2).
Figure 12:
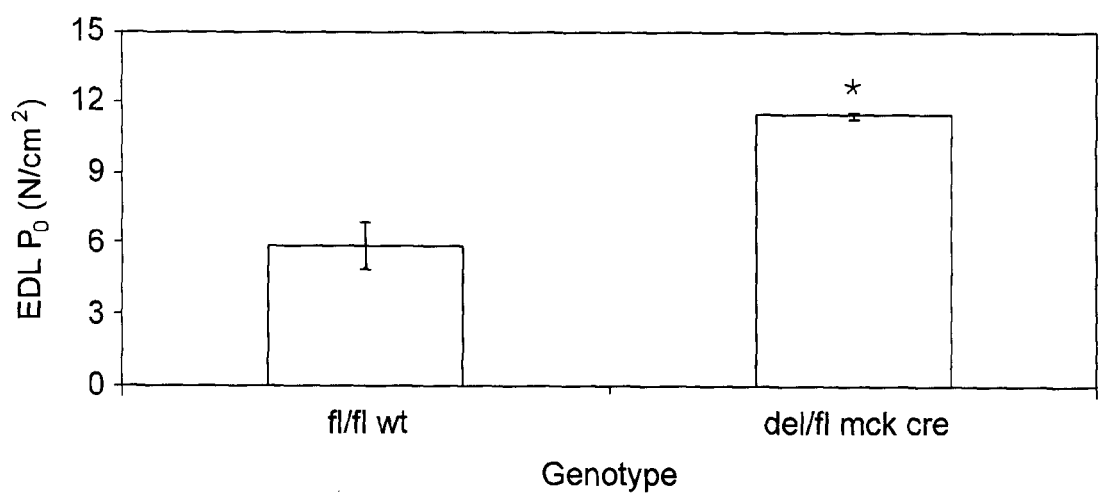
FIG. 12. RANK deletion (RANK del/fl mck cre) reduces significantly the loss of force in fully differentiated skeletal muscle and OPG treatment prevents myotube atrophy. In a model of critical illness myopathy, male mice underwent sciatic denervation and dexamethasone treatment (1 mg/kg). EDL muscles were dissected and contractile properties recorded at 7 days post treatment. Once again, the deletion of RANK (RANK del/fl mck cre genotype) protects remarkedly against the loss of specific force. * Indicates a significant difference (n=2, P≤0.05; Student's t-test).

Findings:

The main consequence of denervation and DEX injections is muscle atrophy, dysfunction and increased myofiber vulnerability to mechanical damage. Our results showed that SERCA activity is markedly superior in EDL muscles from RANK-deficient relative to wild type mice (FIG. 10). Finally, we found that the absence of RANK in skeletal muscle greatly improves force production in EDL but not SOL muscles (FIGS. 11,12).

Example 5 Modulation of RANK/RANKL/OPG Pathway Influences Muscle Integrity in Dystrophic Mdx Mice Rationale:

Duchenne muscular dystrophy (DMD) results from mutations in dystrophin, a cytoskeletal protein that participates in the linkage of actin filaments to the inner surface of the muscle cell membrane. Human patients with DMD and mdx mice lacking dystrophin experience progressive muscle cell death characterized by necrosis and regeneration. Furthermore, several studies have reported membrane leakage and elevated $Ca^{2+}$ content in dystrophic muscle[86,87]. The presence of elevated $Ca^{2+}$ in dystrophic muscle is associated with activation of calpains, a $Ca^{2+}$ dependent cysteine proteases[88]. The overexpression of calpastatin, a specific endogenous inhibitor of calpains, in mdx mice showed reductions in muscle necrosis suggesting that calpains play an active role in muscle degeneration in dystrophic mice[89]. More importantly, very recent works showed that SERCA overexpression in skeletal muscles mitigate muscular dystrophy in dystrophin (mdx) and sarcoglycan (Sgcd) null mice[90]. This important result indicates that efficient $Ca^{2+}$ reuptake by SERCA reestablishes intracellular $Ca^{2+}$ concentration, rescues muscle fiber integrity and function and reduces susceptibility to contraction-induced damage. Furthermore, intrinsic laryngeal muscles that are protected from myonecrosis in mdx mice overexpressed SERCA and calsequestrin[92]. Because the participation of $Ca^{2+}$ in the initial degradation of myofibrillar proteins in dystrophic mice has been established, it is tempting to speculate that RANK/RANKL/OPG pathways which modulate $Ca^{2+}$ reuptake would preserve muscle integrity in dystrophic mice.

Experimental Design:

Treatment of Mdx Mice with OPG and Contractile Properties of SOL and EDL Muscles Male mdx mice (C57BL/10ScSnJ) were purchased from Jackson Laboratories. Mdx mice were then injected i.p. with OPG (0.3 mg/kg/day) for 10 days during the 3rd and 4th week of life. Body weight were measured every 2 days and drug volume were adjusted accordingly. This concentration of OPG is selected because it is known to inhibit RANKL and bone resorption. Four weeks of age is also chosen since several histological observations showed that mdx mice experience the first and most pronounced cycle of degeneration/regeneration[93].

SOL and EDL muscles from male wild type and mdx mice were dissected and contractile properties analyzed at 4 weeks of age.

TABLE 3

Table 3: Contractile and physical properties of SOL and EDL muscles injected with OPG in mdx mice.

| | SOL | | | | EDL | | | |
|---|---|---|---|---|---|---|---|---|
| | C57BL/10J | | mdx | | C57BL/10J | | mdx | |
| | PBS | OPG | PBS | OPG | PBS | OPG | PBS | OPG |
| TPT (ms) | 56.5 ± 12.65 | 50.75 ± 3.83 | 49.75 ± 3.6 | 35.2 ± 2.43 | 24.7 ± 3.8 | 25.8 ± 2.6 | 18.67 ± 0.88 | 29.75 ±7.47 |
| ½ RT (ms) | 48 ± 4.1 | 46.8 ± 5.7 | 35.3 ± 13.5 | 38 ± 3.3 | 21.3 ± 2.7 | 20.3 ± 2.4 | 20.25 ± 1.8 | 20.67 ± 2.18 |
| Pt (g) | 1.44 ± 0.25 | 1.8 ± 0.06 | 0.81 ± 0.15 | 1.2 ± 0.18 | 2.36 ± 0.41 | 2.52 ± 0.26 | 1.4 ± 0.92 | 2.01 ± 0.2 |
| Po (g) | 10.13 ± 0.72 | 10.79 ± 0.27 | 4.65 ± 1.44* | 8.02 ± 2.99* | 18.56 ± 1.88 | 14.53 ± 3.44 | 5.27 ± 2.61* | 10.3 ± 1.3*# |
| Muscle weight (mg) | 4.50 ± 0.08 | 3.73 ± 0.20 | 3.77 ± 0.49 | 4.90 ± 0.72 | 5.57 ± 0.57 | 4.18 ± 0.25 | 4.84 ± 0.74 | 4.96 ± 0.93 |

Young mdx mice or C57BL/10j controls were subjected to OPG injection (0.3 mg/kg/day, i.p., R&D Systems) for 10 days and were sacrificed at 28 days of age. SOL and EDL muscles were incubated ex vivo and stimulated (1, 10, 50, 100 Hz at 35 V) to measure time to peak tension (TPT), half relaxation time ($^{+0} \frac{1}{2}$ RT), maximal twitch tension (Pt) and maximal absolute force (Po). Muscle weight was determined thereafter. Data revealed a strong increase in muscle maximal absolute force especially in EDL muscles and a better preservation in muscle mass. Data are presented as mean +/− sem.
*significantly different from C57BL/10j PBS-injected mice,
significantly different from mdx PBS-injected mice, p < 0.05 (ANOVA with a post-hoc Tukey test).

Figure 13:
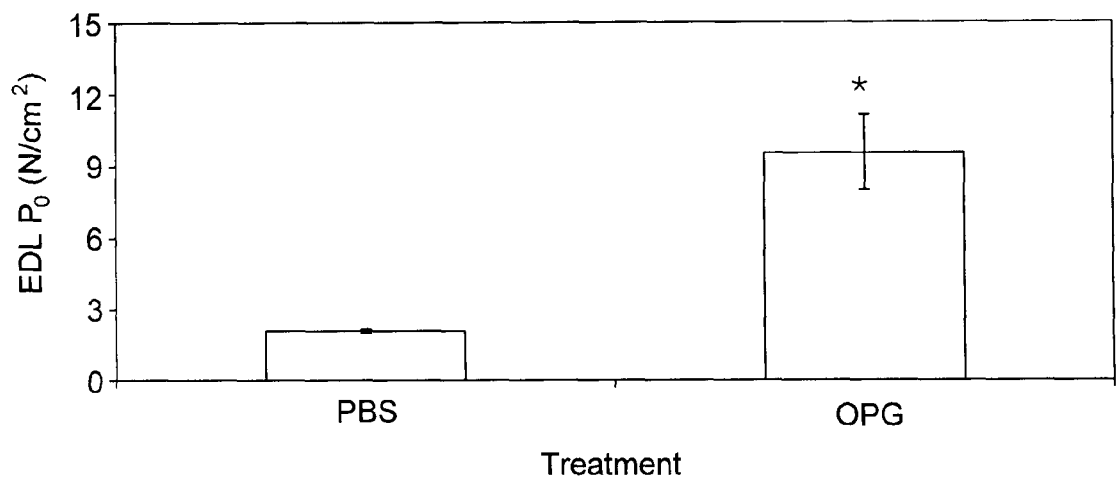
FIG. 13. The injection of OPG increased remarkedly by more than 200% the maximum force production of EDL muscles in mdx mice. Maximum specific tetanic force (N/cm$^2$) of EDL muscles from male mdx mice. Mdx mice were daily injected with 0.3 mg/kg OPG during 10 days. The same volume of PBS was injected in male mdx mice and used as controls. The injections start on day $18^{th}$ after birth. The injection of OPG increased remarkably by more than 200% the maximum force production of EDL muscles in mdx mice* Significant difference (P≤0.05; Student's t-test) (n=2-3).
Figure 14:
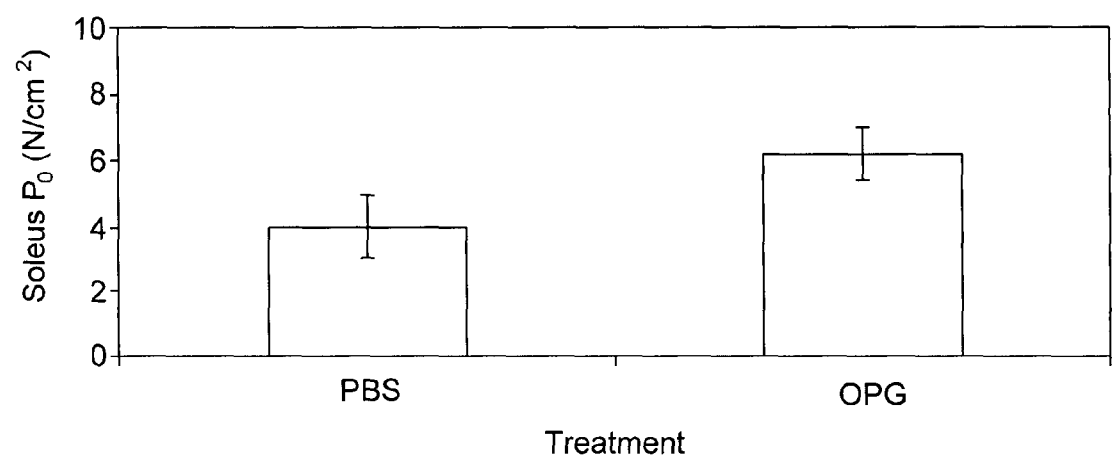
FIG. 14. The injection of OPG increased by more than 50% the maximum force production of SOL muscles in mdx mice. Maximum specific tetanic force (N/cm$^2$) of SOL muscles from male mdx mice. Mdx mice were daily injected with 0.3 mg/kg OPG during 10 days. The same volume of PBS was injected in male mdx mice and used as controls. The injections start on day $18^{th}$ after birth. The injection of OPG increased by more than 50% the maximum force production of SOL muscles in mdx mice * Significant difference (P≤0.05; Student's t-test) (n=2-3).

Findings:

Our data showed that daily OPG injection increased remarkedly by more than 200% and 50% the maximum force production of EDL and SOL muscles, respectively. The present inventor(s) believe that mdx mice treated with OPG will be able to mobilize intracellular $Ca^{2+}$ more efficiently thereby reducing $Ca^{2+}$ concentration and protease activities and protecting muscle function. (FIGS. 13,14)

REFERENCES

1. Woolf A D, Pfleger B. Burden of major musculoskeletal conditions. Bull World Health Organ. 2003, 81: 646-656.
2. Cunningham L S, Kelsey J L. Epidemiology of musculoskeletal impairments and associated disability. Am J Public Health. 1984, 74: 574-579.
3. National Cancer Institute of Canada. Canadian Cancer Statistics 1989. Toronto, Ontario, 1989.
4. Di Monaco M, Vallero F, Di Monaco R, Tappero R. Prevalence of sarcopenia and its association with osteoporosis in 313 older women following a hip fracture. Arch Gerontol Geriatr. 2011, 52: 71-74.
5. Berne R M. and Levy M N: *Physiology*, ed 4, St. Louis, 1998, Mosby.
6. Boss G R, Seegmiller J E. Age-related physiological changes and their clinical significance. West J Med. 1981, 135: 434-440.
7. Bloomfield S A. Changes in musculoskeletal structure and function with prolonged bed rest. Med Sci Sports Exerc. 1997, 29: 197-206.
8. Jost P D. Simulating human space physiology with bed rest. Hippokratia. 2008, 12 Suppl 1: 37-40.
9. Pang M Y, Eng J J, McKay H A, Dawson A S. Reduced hip bone mineral density is related to physical fitness and leg lean mass in ambulatory individuals with chronic stroke. Osteoporos Int. 2005, 16: 1769-1779.
10. Qin W, Bauman W A, Cardozo C. Bone and muscle loss after spinal cord injury: organ interactions. Ann NY Acad Sci. 2010, 1211: 66-84.
11. Odessey R, Allen E R, Newman W P. A model to study local effects of thermal trauma on muscle metabolism. Circ Shock. 1983, 11: 131-140.
12. Lunn M R, Wang C H. Spinal muscular atrophy. Lancet. 2008, 371: 2120-2133.
13. Ilyin E A, Oganov V S. Microgravity and musculoskeletal system of mammals. Adv Space Res. 1989, 9: 11-9.
14. Zarzhevsky N, Menashe O, Carmeli E, Stein H, Reznick A Z. Capacity for recovery and possible mechanisms in immobilization atrophy of young and old animals. Ann NY Acad Sci. 2001, 928:212-225.
15. Wroblewski R, Nordemar R. Ultrastructural and histochemical studies of muscle in rheumatoid arthritis. Scand J Rheumatol. 1975, 197-204.
16. Goldspink D F. The effects of denervation on protein turnover of the soleus and xtensor digitorum longus muscles of adult mice. Comp Biochem Physiol B. 1978, 61: 37-41.
17. Dore R K, Cohen S B, Lane N E, Palmer W, Shergy W, Zhou L, Wang H, Tsuji W, Newmark R; Denosumab R A Study Group. Effects of denosumab on bone mineral density and bone turnover in patients with rheumatoid arthritis receiving concurrent glucocorticoids or bisphosphonates. Ann Rheum Dis. 2010, 69: 872-875.
18. Perrini S, Laviola L, Carreira M C, Cignarelli A, Natalicchio A, Giorgino F. The GH/IGF1 axis and signaling pathways in the muscle and bone: mechanisms underlying age-related skeletal muscle wasting and osteoporosis. J Endocrinol. 2010, 205: 201-210.
19. Langen R C, Van Der Velden J. L, Schols A M, Kelders M C, Wouters E F, Janssen-Heininger Y M. Tumor necrosis factor-alpha inhibits myogenic differentiation through MyoD protein destabilization. FASEB J. 2004, 18: 227-237.
20. Eapen A S, Sundivakkam P, Song Y, Ravindran S, Ramachandran A, Tiruppathi C, George A. $Ca^{2+}$-mediated stress kinase activation by DMP1 promotes osteoblast differentiation. J Biol Chem. 2010, 285: 36339-36351.
21. Naya F J, Mercer B, Shelton J, Richardson J A, Williams R S, Olson E N. Stimulation of slow skeletal muscle fiber gene expression by calcineurin in vivo. J Biol Chem. 2000, 275: 4545-4548.

22. Gonyea W J, Ericson G C. An experimental model for the study of exercise-induced skeletal muscle hypertrophy. J Appl Physiol. 1976, 40: 630-633.
23. Smith E L, Gilligan C. Physical activity effects on bone metabolism. Calcif Tissue Int. 1991, 49 Suppl: S50-54.
24. Papadopouli A E, Klonaris C N, Theocharis S E. Role of OPG/RANKL/RANK axis on the vasculature. Histol Histopathol. 2008, 23: 497-506.
25. Simonet W S, Lacey D L, Dunstan C R, Kelley M, Chang M S, Lüthy R, Nguyen H Q, Wooden S, Bennett L, Boone T, Shimamoto G, DeRose M, Elliott R, Colombero A, Tan H L, Trail G, Sullivan J, Davy E, Bucay N, Renshaw-Gegg L, Hughes T M, Hill D, Pattison W, Campbell P, Sander S, Van G, Tarpley J, Derby P, Lee R, Boyle W J. Osteoprotegerin: a novel secreted protein involved in the regulation of bone density. Cell. 1997, 89: 309-319.
26. Bucay N, Sarosi I, Dunstan C R, Morony S, Tarpley J, Capparelli C, Scully S, Tan H L, Xu W, Lacey D L, Boyle W J, Simonet W S. osteoprotegerin-deficient mice develop early onset osteoporosis and arterial calcification. Genes Dev. 1998, 12: 1260-1268.
27. Mizuno A, Amizuka N, Irie K, Murakami A, Fujise N, Kanno T, Sato Y, Nakagawa N, Yasuda H, Mochizuki S, Gomibuchi T, Yano K, Shima N, Washida N, Tsuda E, Morinaga T, Higashio K, Ozawa H. Severe osteoporosis in mice lacking osteoclastogenesis inhibitory factor/osteoprotegerin. Biochem Biophys Res Commun. 1998, 247: 610-615.
28. Dougall W C, Glaccum M, Charrier K, Rohrbach K, Brasel K, De Smedt T, Daro E, Smith J, Tometsko M E, Maliszewski C R, Armstrong A, Shen V, Bain S, Cosman D, Anderson D, Morrissey P J, Peschon J J, Schuh J. RANK is essential for osteoclast and lymph node development. Genes Dev. 1999, 13: 2412-2424.
29. Hofbauer L C, Khosla S, Dunstan C R, Lacey D L, Boyle W J, Riggs B L. The roles of osteoprotegerin and osteoprotegerin ligand in the paracrine regulation of bone resorption. J Bone Miner Res. 2000, 15: 2-12.
30. Wouters E F. Muscle Wasting in Chronic Obstructive Pulmonary Disease Am J Respir Crit Care Med. 2006, 173: 4-5.
31. Herndon D N, Ramzy P I, DebRoy M A, Zheng M, Ferrando A A, Chinkes D L, Barret J P, Wolfe R R, Wolf S E. Muscle protein catabolism after severe burn: effects of IGF-1/IGFBP-3 treatment. Ann Surg. 1999, 229: 713-722.
32. Tisdale M J. Cancer cachexia. Langenbecks Arch Surg. 2004, 389: 299-305.
33. Ventadour S, Attaix D. Mechanisms of skeletal muscle atrophy. Curr Opin Rheumatol. 2006, 18: 631-635.
34. Li H, Malhotra S, Kumar A. Nuclear factor-kappa B signaling in skeletal muscle atrophy. J Mol Med. 2008, 86: 1113-1126.
35. Rock K L, Gramm C, Rothstein L, Clark K, Stein R, Dick L, Hwang D, Goldberg A L. Inhibitors of the proteasome block the degradation of most cell proteins and the generation of peptides presented on MHC class I molecules. Cell. 1994, 78: 761-771.
36. Bodine S C, Latres E, Baumhueter S, Lai V K, Nunez L, Clarke B A, Poueymirou W T, Panaro F J, Na E, Dharmarajan K, Pan Z Q, Valenzuela D M, DeChiara T M, Stitt T N, Yancopoulos G D, Glass D J. Identification of ubiquitin ligases required for skeletal muscle atrophy. Science. 2001, 294: 1704-1708.
37. Murton A J, Constantin D, Greenhaff P L. The involvement of the ubiquitin proteasome system in human skeletal muscle remodelling and atrophy. Biochim Biophys Acta. 2008, 1782: 730-743.
38. DeVol D L, Rotwein P, Sadow J L, Novakofski J, Bechtel P J. Activation of insulin-like growth factor gene expression during work-induced skeletal muscle growth. Am J Physiol. 1990, 259: E89-95.
39. Musarò A, McCullagh K, Paul A, Houghton L, Dobrowolny G, Molinaro M, Barton E R, Sweeney H L, Rosenthal N. Localized Igf-1 transgene expression sustains hypertrophy and regeneration in senescent skeletal muscle. Nat Genet. 2001, 27: 195-200
40. Musarò A, Giacinti C, Borsellino G, Dobrowolny G, Pelosi L, Cairns L, Ottolenghi S, Cossu G, Bernardi G, Battistini L, Molinaro M, Rosenthal N. Stem cell-mediated muscle regeneration is enhanced by local isoform of insulin-like growth factor 1. Proc Natl Acad Sci USA. 2004, 101: 1206-1210.
41. Glass D J. Skeletal muscle hypertrophy and atrophy signaling pathways. Int J Biochem Cell Biol. 2005, 37: 1974-1984.
42. Sandri M, Sandri C, Gilbert A, Skurk C, Calabria E, Picard A, Walsh K, Schiaffino S, Lecker S H, Goldberg A L. Foxo transcription factors induce the atrophy-related ubiquitin ligase atrogin-1 and cause skeletal muscle atrophy. Cell. 2004, 117:399-412.
43. Caffrey J M, Farach-Carson M C. Vitamin D3 metabolites modulate dihydropyridinesensitive $Ca^{2+}$ currents in clonal rat osteosarcoma cells. J Biol Chem. 1989, 264: 20265-20274.
44. Vazquez G, de Boland A R, Boland R L. 1alpha,25-dihydroxy-vitamin-D3-induced storeoperated Ca2+ influx in skeletal muscle cells. Modulation by phospholipase C, protein kinase C, and tyrosine kinases. J Biol Chem. 1998, 273: 33954-33960.
45. Dzhura I, Wu Y, Colbran R J, Balser J R, Anderson M E. Calmodulin kinase determines $Ca^{2+}$-dependent facilitation of L-type $Ca^{2+}$ channels. Nat Cell Biol. 2000, 2: 173-177.
46. Crabtree G R. $Ca^{2+}$, calcineurin, and the control of transcription. J Biol Chem. 2001, 276: 2313-2316.
47. Catterall W A. Structure and regulation of voltage-gated $Ca^{2+}$ channels. Annu Rev Cell Dev Biol. 2000, 16: 521-555.
48. Bergh J J, Xu Y, Farach-Carson M C. Osteoprotegerin expression and secretion are regulated by $Ca^{2+}$ influx through the L-type voltage-sensitive $Ca^{2+}$ channel. Endocrinology. 2004, 145: 426-436.
49. Ridings J E, Palmer A K, Davidson E J, Baldwin J A. Prenatal toxicity studies in rats and rabbits with the $Ca^{2+}$ channel blocker diproteverine. Reprod Toxicol. 1996, 10: 43-49.
50. Melzer W, Herrmann-Frank A, Lüttgau H C. The role of Ca2+ ions in excitation-contraction coupling of skeletal muscle fibres. Biochim Biophys Acta. 1995, 1241: 59-116.
51. Reiken S, Lacampagne A, Zhou H, Kherani A, Lehnart S E, Ward C, Huang F, Gaburjakova M, Gaburjakova J, Rosemblit N, Warren M S, He K L, Yi G H, Wang J, Burkhoff D, Vassort G, Marks A R. PKA phosphorylation activates the $Ca^{2+}$ release channel (ryanodine receptor) in skeletal muscle: defective regulation in heart failure. J Cell Biol. 2003, 160: 919-928.
52. Marx S O, Ondrias K, Marks A R. Coupled gating between individual skeletal muscle Ca2+ release channels (ryanodine receptors). Science. 1998, 281: 818-821.

53. Talmadge R J. Myosin heavy chain isoform expression following reduced neuromuscular activity: potential regulatory mechanisms. Muscle Nerve. 2000, 23: 661-679.

54. Sugiura T, Miyata H, Kawai Y, Matoba H, Murakami N. Changes in myosin heavy chain isoform expression of overloaded rat skeletal muscles. Int J Biochem. 1993, 25: 1609-1613.

55. Acharyya S, Guttridge D C. Cancer cachexia signaling pathways continue to emerge yet much still points to the proteasome. Clin Cancer Res. 2007, 13: 1356-1361.

56. Penner C G, Gang G, Wray C, Fischer J E, Hasselgren P O. The transcription factors NF-Ib and AP-1 are differentially regulated in skeletal muscle during sepsis. Biochem Biophys Res Commun. 2001, 281: 1331-1336.

57. Penner G, Gang G, Sun X, Wray C, Hasselgren P O. C/EBP DNA-binding activity is upregulated by a glucocorticoid-dependent mechanism in septic muscle. Am J Physiol Regul Integr Comp Physiol. 2002, 282: R439-R444.

58. Yang H, Mammen J, Wei W, Menconi M, Evenson A, Fareed M, Petkova V, Hasselgren P O. Expression and activity of C/EBP® and delta are upregulated by dexamethasone in skeletal muscle. J Cell Physiol. 2005, 204: 219-226.

59. Williams A B, Decourten-Myers G M, Fischer J E, Luo G, Sun X, Hasselgren P O. Sepsis stimulates release of myofilaments in skeletal muscle by a $Ca^{2+}$-dependent mechanism. FASEB J. 1999, 13: 1435-1443.

60. Ferrand-Drake M, Zhu C, Gido G, Hansen A J, Karlsson J O, Bahr B A, Zamzami N, Kroemer G, Chan P H, Wieloch T, Blomgren K. Cyclosporin A prevents calpain activation despite increased intracellular $Ca^{2+}$ concentrations, as well as translocation of apoptosisinducing factor, cytochrome c and caspase-3 activation in neurons exposed to transient hypoglycemia. J Neurochem. 2003, 85: 1431-1442.

61. Menconi M J, Wei W, Yang H, Wray C J, Hasselgren P O. Treatment of cultured myotubes with the $Ca^{2+}$ ionophore A23187 increases proteasome activity via a CaMK II-caspasecalpain-dependent mechanism. Surgery 2004, 136: 135-142.

62. Kubis H P, Haller E A, Wetzel P, Gros G. *Adult fast myosin pattern and Ca2+-induced slow pattern in primary skeletal muscle culture.* Proc Natl Acad Sci USA. 1997, 94: 4205-10.

63. Morey-Holton E R, Globus R K. *Hindlimb unloading rodent model: technical aspects.* J Appl Physiol. 2002, 92: 1367-77.

64. Frenette J, St-Pierre M, Côté CH, Mylona E, Pizza F X. *Muscle impairment occurs rapidly and precedes inflammatory cell accumulation after mechanical loading.* Am J Physiol Regul Integr Comp Physiol. 2002, 282: R351-7.

65. Chakkalakal J V, Harrison M A, Carbonetto S, Chin E, Michel R N, Jasmin B J. *Stimulation of calcineurin signaling attenuates the dystrophic pathology in mdx mice.* Hum Mol Genet. 2004, 13: 379-88.

66. Ryder J W, Bassel-Duby R, Olson E N, Zierath J R. *Skeletal muscle reprogramming by activation of calcineurin improves insulin action on metabolic pathways.* J Biol Chem. 2003, 278: 44298-304.67. Brüning J C, Michael M D, Winnay J N, Hayashi T, Hörsch D, Accili D, Goodyear L J, Kahn C R. A muscle-specific insulin receptor knockout exhibits features of the metabolic syndrome of NIDDM without altering glucose tolerance. Mol Cell. 1998, 2: 559-569.

68. Brooks S V, Faulkner J A. Contractile properties of skeletal muscles from young, adult and aged mice. J Physiol. 1988, 404: 71-82.

69. Frenette J, St-Pierre M, Côté CH, Mylona E, Pizza F X. Muscle impairment occurs rapidly and precedes inflammatory cell accumulation after mechanical loading. Am J Physiol Regul Integr Comp Physiol. 2002, 282: R351-357.

70. Simonides W S, van Hardeveld C. An assay for sarcoplasmic reticulum $Ca_{2(+)}$-ATPase activity in muscle homogenates. Anal Biochem. 1990, 191: 321-331.

71. Chan S, Head S I. Age- and gender-related changes in contractile properties of nonatrophied EDL muscle. PLoS One. 2010, 5: e12345.

72. Tiao G, Lieberman M, Fischer J E, Hasselgren P O. Intracellular regulation of protein degradation during sepsis is different in fast- and slow-twitch muscle. Am J Physiol. 1997, 272: R849-R856.

73. Clarke B A, Drujan D, Willis M S, Murphy L O, Corpina R A, Burova E, Rakhilin S V, Stitt T N, Patterson C, Latres E, Glass D J. The E3 Ligase MuRF1 degrades myosin heavy chain protein in dexamethasone-treated skeletal muscle. Cell Metab. 2007, 6: 376-385.

74. Schakman O, Gilson H, Thissen J P. Mechanisms of glucocorticoid-induced myopathy. J Endocrinol. 2008, 197: 1-10.75. Ogata N, Chikazu D, Kubota N, Terauchi Y, Tobe K, Azuma Y, Ohta T, Kadowaki T, Nakamura K, Kawaguchi H. Insulin receptor substrate-1 in osteoblast is indispensable for maintaining bone turnover. J Clin Invest. 2000, 105: 935-943.

76. Bu Y H, He Y L, Zhou H D, Liu W, Peng D, Tang A G, Tang L L, Xie H, Huang Q X, Luo X H, Liao E Y. Insulin receptor substrate 1 regulates the cellular differentiation and the matrix metallopeptidase expression of preosteoblastic cells. J Endocrinol. 2010, 206: 271-277.

77. Krakauer J C, McKenna M J, Rao D S, Whitehouse F W. Bone mineral density in diabetes. Diabetes Care. 1997, 20: 1339-1340.

78. Laron Z, Klinger B, Silbergeld A. Patients with Laron syndrome have Osteopenia/Osteoporosis. J Bone Miner Res. 1999, 14: 156-157.

79. de Letter M A, Schmitz P I, Visser L H, Verheul F A, Schellens R L, Op de Coul D A, van der Meché F G. Risk factors for the development of polyneuropathy and myopathy in critically ill patients. Crit Care Med. 2001, 29: 2281-2286.

80. Lacomis D, Petrella J T, Giuliani M J. Causes of neuromuscular weakness in the intensive care unit: a study of ninety-two patients. Muscle Nerve. 1998, 21: 610-617.

81. Hund E. Myopathy in critically ill patients. Crit Care Med. 1999, 27: 2544-2547.

82. Friedrich O, Hund E, Weber C, Hacke W, Fink R H. Critical illness myopathy serum fractions affect membrane excitability and intracellular $Ca^{2+}$ release in mammalian skeletal muscle. J Neurol. 2004, 251: 53-65.

83. Lacomis D. Critical illness myopathy. Curr Rheumatol Rep. 2002, 403-408.

84. Friedrich O, Hund E, von Wegner F. Enhanced muscle shortening and impaired Ca2+ channel function in an acute septic myopathy model. J Neurol. 2010, 257: 546-555.

85. Mozaffar T, Haddad F, Zeng M, Zhang L Y, Adams G R, Baldwin K M. Molecular and cellular defects of skeletal muscle in an animal model of acute quadriplegic myopathy. Muscle Nerve. 2007, 35: 55-65.

86. Straub V, Rafael J A, Chamberlain J S, Campbell K P. Animal models for muscular dystrophy show different patterns of sarcolemmal disruption. J Cell Biol. 1997 Oct. 20; 139(2):375-85.
87. Bodensteiner J B, Engel A G. Intracellular $Ca^{2+}$ accumulation in Duchenne dystrophy and other myopathies: a study of 567,000 muscle fibers in 114 biopsies. Neurology. 1978, 5: 439-46.
88. Sorimachi H, Imajoh-Ohmi S, Emori Y, Kawasaki H, Ohno S, Minami Y, Suzuki K. Molecular cloning of a novel mammalian $Ca^{2+}$-dependent protease distinct from both m- and mu-types. Specific expression of the mRNA in skeletal muscle. J Biol Chem. 1989, 264: 20106-11.
89. Spencer M J, Mellgren R L. Overexpression of a calpastatin transgene in mdx muscle reduces dystrophic pathology. Hum Mol Genet. 2002 Oct. 1; 11(21):2645-55.
90. Goonasekera S A, Lam C K, Millay D P, Sargent M A, Hajjar R J, Kranias E G, Molkentin J D. Mitigation of muscular dystrophy in mice by SERCA overexpression in skeletal muscle. J Clin Invest. 2011 Mar. 1; 121(3):1044-52.
91. Morine K J, Sleeper M M, Barton E R, Sweeney H L. Overexpression of SERCA1a in the mdx diaphragm reduces susceptibility to contraction-induced damage. Hum Gene Ther. 2010 December; 21(12):1735-9.
92. Ferretti R, Marques M J, Pertille A, Santo Neto H. Sarcoplasmic-endoplasmic-reticulum Ca2+-ATPase and calsequestrin are overexpressed in spared intrinsic laryngeal muscles of dystrophin-deficient mdx mice. Muscle Nerve. 2009, 39: 609-15.
93. Pastoret C, Sebille A. mdx mice show progressive weakness and muscle deterioration with age. J Neurol Sci. 1995, 129: 97-105.

---

The invention claimed is:

1. A method for the therapeutic treatment of a muscular dystrophy, the method comprising administering a therapeutically effective amount of one or more receptor activator of nuclear factor kappa-B ligand (RANKL) antagonists or a pharmaceutical composition comprising a therapeutically effective amount of one or more RANKL antagonists and a pharmaceutically acceptable carrier to a patient in need of treatment for a muscular dystrophy, wherein the RANKL antagonists are OPG (osteoprotegerin), a truncated OPG polypeptide, which binds to RANKL, or an anti-RANKL antibody, wherein the antagonists inhibit RANKL activity in the patient, and wherein RANKL is a polypeptide consisting of the amino acid sequence set forth in SEQ ID NO: 1.

2. The method according to claim 1, wherein the muscular dystrophy is Duchenne muscular dystrophy or Berker muscular dystrophy.

3. The method according to claim 1, wherein the one or more RANKL antagonists are OPG or a monoclonal anti-RANKL antibody.

4. The method according to claim 1, wherein the one or more RANKL antagonists is a humanized monoclonal anti-RANKL antibody.

5. The method according to claim 1, wherein the one or more RANKL antagonists is Denosumab.

6. The method according to claim 1, wherein the one or more RANKL antagonists is OPG.

7. The method according to claim 1, further comprising administering one or more further therapeutic agents indicated for the treatment of muscular dystrophy.

8. The method according to claim 7 wherein the one or more further therapeutic agents are selected from the group consisting of:
an angiotensin converting enzyme (ACE) inhibitor, and
a β2 agonist.

9. The method of claim 7, wherein said one or more RANKL antagonists or said pharmaceutical composition and said one or more further therapeutic agents are administered simultaneous.

10. The method of claim 7, wherein said one or more RANKL antagonists or said pharmaceutical composition and said one or more further therapeutic agents are administered consecutively.

11. The method according to claim 1, wherein the pharmaceutical composition comprises one or more further therapeutic agents indicated for the treatment of muscular dystrophy.

12. The method according to claim 11 wherein the one or more further therapeutic agents are one or more of:
an angiotensin converting enzyme (ACE) inhibitor, and
a β2 agonist.

13. The method of claim 8, wherein the ACE inhibitor is captopril or zofenopril.

14. The method of claim 8, wherein the ACE inhibitor is selected from the group consisting of enalapril, ramipril, quinapril, perindopril, lisinopril, benazepril, imidapril, zofenopril and trandolapril.

15. The method of claim 8, wherein the ACE inhibitor is fosinopril.

16. The method of claim 8, wherein the β2 agonist is clenbuterol or formoterol.

17. The method of claim 12, wherein the ACE inhibitor is captopril or zofenopril.

18. The method of claim 12, wherein the ACE inhibitor is selected from the group consisting of enalapril, ramipril, quinapril, perindopril, lisinopril, benazepril, imidapril, zofenopril and trandolapril.

19. The method of claim 12, wherein the ACE inhibitor is fosinopril.

20. The method of claim 12, wherein the β2 agonist is clenbuterol or formoterol.

* * * * *

UNITED STATES PATENT AND TRADEMARK OFFICE
CERTIFICATE OF CORRECTION

PATENT NO. : 9,757,451 B2  Page 1 of 3
APPLICATION NO. : 14/356579
DATED : September 12, 2017
INVENTOR(S) : Frenette et al.

It is certified that error appears in the above-identified patent and that said Letters Patent is hereby corrected as shown below:

On the Title Page

In Column 2 (page 2, item (56)) at Line 31, Change ""Ostoprotegerin" to --"Osteoprotegerin--

In the Specification

In Column 2 at Line 33, Change "aging$^{31,32,33,34}$." to --aging$^{30,31,32,33,34}$.--.

In Column 9 at Line 67, Change "rigourously" to --rigorously--.

In Column 10 at Line 22, Change "Ca$^2$+" to --Ca$^{2+}$--.

In Column 10 at Line 35, Change "[Ca$^{2+}$ ]$_i$" to --[Ca$^{2+}$]$_i$--.

In Column 12 at Line 14, Change "ore" to --or--.

In Column 12 at Line 25, Change "ore" to --or--.

In Column 12 at Line 28, Change "ore" to --or--.

In Column 13 at Line 11, Change "prologed" to --prolonged--.

In Column 13 at Line 24, Change "[Ca$^{2+}$ ]i;" to --[Ca$^{2+}$]$_{i;}$--.

In Column 13 at Line 37, Change "non genetic" to --non-genetic--.

In Column 13 at Line 49, Change "and or" to --and/or--.

In Column 13 at Line 57, Change "and or" to --and/or--.

Signed and Sealed this
Fourth Day of June, 2019

Andrei Iancu
*Director of the United States Patent and Trademark Office*

CERTIFICATE OF CORRECTION (continued)
U.S. Pat. No. 9,757,451 B2

In Column 13 at Line 64, Change "and or" to --and/or--.

In Column 14 at Line 4, Change "and or" to --and/or--.

In Column 14 at Line 17, Change "prednosol," to --prednesol,--.

In Column 14 at Lines 27-28, Change "and or" to --and/or--.

In Column 17 at Line 14, Change "5λSSC" to --5XSSC--.

In Column 18 at Line 16, Change "pharmalogical" to --pharmacological--.

In Column 18 at Line 18, Change "Pharmalogy" to --Pharmacology--.

In Column 18 at Line 42, Change "construed ?as" to --construed as--.

In Column 20 at Line 29, Change "Rosenburg" to --Rosenberg--.

In Column 21 at Line 62, Change "and or" to --and/or--.

In Column 23 at Line 59, Change "formulatory" to --formulary--.

In Column 26 at Line 16 (approx.), Change "$[Ca^{2+}]_i$" to --$[Ca^{2+}]_i$--.

In Column 26 at Line 37, Change "myofibres[67]." to --myofibers[67].--.

In Column 27 at Line 58 (approx.), Change "myofibres[67]." to --myofibers[67].--.

In Column 30 at Line 23, Change "myofibres" to --myofibers--.

In Column 30 at Line 24, Change "myofibres" to --myofibers--.

In Column 30 at Line 41, Change "rigourously" to --rigorously--.

In Column 31 at Line 32 (approx.), Change "$[Ca^{2+}]_i$" to --$[Ca^{2+}]_i$--.

In Column 32 at Line 6, Change "$[Ca^{2+}]_i$" to --$[Ca^{2+}]_i$--.

In Column 32 at Line 37, Change "myofibres[73]." to --myofibers[73].--.

In Column 33 at Line 25, Change "exemple#2." to --example#2.--.

In Column 34 at Line 7, Change "mimicks" to --mimics--.

In Column 34 at Line 19, Change "#2" to --#2.--.

CERTIFICATE OF CORRECTION (continued)
U.S. Pat. No. 9,757,451 B2

In Column 34 at Line 55, Change "damage." to --damage$^{91}$.--.

In Columns 35-36 at Line 27 (approx.), Change "mice," to --mice.--.

In Column 36 at Line 41 (approx.), Change "xtensor" to --extensor--.

In Column 38 at Line 13, Change "195-200" to --195-200.--.

In Column 39 at Lines 62-67, Delete "67. Bruning J C, Michael M D, Winnay J N, Hayashi T, Horsch D, Accili D, Goodyear L J, Kahn C R. A muscle-specific insulin receptor knockout exhibits features of the metabolic syndrome of NIDDM without altering glucose tolerance. Mol Cell. 1998, 2: 559-569." and insert the same on Column 39, Line 63 as a new paragraph.

In Column 40 at Lines 27-31, Delete "75. Ogata N, Chikazu D, Kubota N, Terauchi Y, Tobe K, Azuma Y, Ohta T, Kadowaki T, Nakamura K, Kawaguchi H. Insulin receptor substrate-1 in osteoblast is indispensable for maintaining bone turnover. J Clin Invest. 2000, 105: 935-943." and insert the same on Column 40, Line 28 as a new paragraph.

In the Claims

In Column 43 at Line 25 (approx.), In Claim 1, change "polypeptide," to --polypeptide--.